(12) United States Patent  (10) Patent No.: US 8,697,874 B2
Okaniwa  (45) Date of Patent: Apr. 15, 2014

(54) HETEROCYCLIC COMPOUND AND USE THEREOF

(75) Inventor: Masanori Okaniwa, Fujisawa (JP)

(73) Assignee: Takeda Pharmaceutical Company Limited, Osaka (JP)

(*) Notice: Subject to any disclaimer, the term of this patent is extended or adjusted under 35 U.S.C. 154(b) by 174 days.

(21) Appl. No.: 13/132,253

(22) PCT Filed: Nov. 30, 2009

(86) PCT No.: PCT/JP2009/070131
§ 371 (c)(1),
(2), (4) Date: Jun. 1, 2011

(87) PCT Pub. No.: WO2010/064611
PCT Pub. Date: Jun. 10, 2010

(65) Prior Publication Data
US 2011/0237620 A1  Sep. 29, 2011

(30) Foreign Application Priority Data

Dec. 1, 2008  (JP) ................................. 2008-306614

(51) Int. Cl.
C07D 513/04  (2006.01)
A61K 31/4365  (2006.01)

(52) U.S. Cl.
USPC ......................................... 546/114; 514/301

(58) Field of Classification Search
USPC ......................................... 546/114; 514/301
See application file for complete search history.

(56) References Cited

U.S. PATENT DOCUMENTS

| | | | |
|---|---|---|---|
| 2,399,026 A | 4/1946 | Henzi et al. | |
| 4,096,264 A | 6/1978 | Bochis et al. | |
| 4,177,274 A | 12/1979 | Bochis et al. | |
| 4,237,300 A | 12/1980 | Bochis et al. | |
| 6,797,823 B1 | 9/2004 | Kubo et al. | |
| 7,071,216 B2 | 7/2006 | Renhowe et al. | |
| 7,238,813 B2 | 7/2007 | Cheung et al. | |
| 7,728,010 B2 | 6/2010 | Amiri et al. | |
| 2002/0133005 A1 | 9/2002 | Iino et al. | |
| 2004/0122237 A1 | 6/2004 | Amiri et al. | |
| 2006/0160832 A1 | 7/2006 | Funahashi et al. | |
| 2006/0241301 A1 | 10/2006 | Hoelzemann et al. | |
| 2007/0021456 A1 | 1/2007 | Mitjans et al. | |
| 2007/0249600 A1 | 10/2007 | Cheung et al. | |
| 2008/0021048 A1 | 1/2008 | Bennett et al. | |
| 2009/0163488 A1 | 6/2009 | Oguro et al. | |
| 2010/0029619 A1 | 2/2010 | Uchikawa et al. | |
| 2010/0196368 A1 | 8/2010 | Amiri et al. | |
| 2010/0249119 A1 | 9/2010 | Hirose et al. | |

FOREIGN PATENT DOCUMENTS

| | | |
|---|---|---|
| EP | 2 181 987 | 5/2010 |
| JP | 52-73896 | 6/1977 |
| JP | 2004-517080 | 6/2004 |
| JP | 2007-507428 | 3/2007 |
| JP | 2010-077109 | 4/2010 |
| WO | 98/35958 | 8/1998 |
| WO | 99/10325 | 3/1999 |
| WO | 99/16438 | 4/1999 |
| WO | 00/41698 | 7/2000 |
| WO | 00/42012 | 7/2000 |
| WO | 01/02359 | 1/2001 |
| WO | 01/32651 | 5/2001 |
| WO | 01/57008 | 8/2001 |
| WO | 01/60814 | 8/2001 |
| WO | 01/66539 | 9/2001 |
| WO | 01/66540 | 9/2001 |
| WO | 02/24680 | 3/2002 |

(Continued)

OTHER PUBLICATIONS

Lu et. al. "Solution phase parallel synthesis and evaluation of MAPK inhibitory activities of close structural analogues of a Ras pathway modulator" Bioorganic & Medicinal Chemistry Letters 14 (2004) 3957-3962.*

(Continued)

*Primary Examiner* — David K O Dell
(74) *Attorney, Agent, or Firm* — Hamre, Schumann, Mueller & Larson, P.C.

(57) ABSTRACT

A compound represented by formula (I) or a salt thereof, which has a potent Raf inhibitory activity.

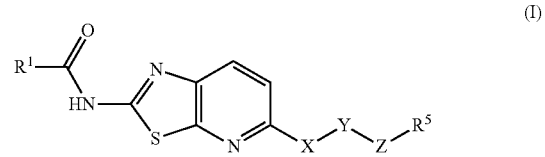

In formula (I), $R^1$ represents an optionally substituted $C_{1-6}$ alkyl, etc.; X represents —O— or —$NR^2$— (wherein $R^2$ represents a hydrogen atom or a $C_{1-6}$ alkyl); Y represents a group represented by formula 2 (2i or 2ii)

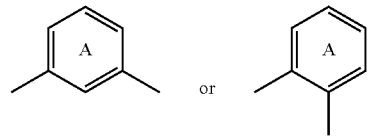

(wherein ring A represents an optionally substituted benzene ring; Z represents a group represented by (1) —$NR^3CO$—$W^1$—, (2) —$NR^3CO$—$W^1$—O—, (3) —$NR^3CO$—$W^1$—O—$W^2$—, (4) —$NR^3CO$—$W^1$—S—, (5) —$NR^3CO$—$W^1$—$NR^4$—, (6) —$NR^3COO$—, (7) —$NR^3COO$—$W^1$—, (8) —$NR^3CO$—CO—, or (9) —$NR^3CONR^4$— (wherein $R^3$ and $R^4$ each represents a hydrogen atom, etc., and $W^1$ and $W^2$ each represents an optionally substituted $C_{1-6}$ alkylene, etc.); and $R^5$ represents an optionally substituted five- or six-membered ring group.

7 Claims, No Drawings

(56) References Cited

FOREIGN PATENT DOCUMENTS

| | | |
|---|---|---|
| WO | 02/44156 | 6/2002 |
| WO | 02/062763 | 8/2002 |
| WO | 02/094808 | 11/2002 |
| WO | 03/022833 | 3/2003 |
| WO | 03/022836 | 3/2003 |
| WO | 03/022837 | 3/2003 |
| WO | 03/022838 | 3/2003 |
| WO | 03/074515 | 9/2003 |
| WO | 03/082272 | 10/2003 |
| WO | 2004/087153 | 10/2004 |
| WO | 2005/019192 | 3/2005 |
| WO | 2005/019216 | 3/2005 |
| WO | 2005/032548 | 4/2005 |
| WO | 2005/037273 | 4/2005 |
| WO | 2005/112932 | 12/2005 |
| WO | 2006/030031 | 3/2006 |
| WO | 2006/071035 | 7/2006 |
| WO | 2006/076376 | 7/2006 |
| WO | 2007/007886 | 1/2007 |
| WO | 2007/030377 | 3/2007 |
| WO | 2007/041365 | 4/2007 |
| WO | 2007/058482 | 5/2007 |
| WO | 2007/121484 | 10/2007 |
| WO | 2008/016131 | 2/2008 |
| WO | 2008/016192 | 2/2008 |
| WO | 2008/150015 | 12/2008 |
| WO | 2009/025358 | 2/2009 |
| WO | 2009/02829 | 3/2009 |
| WO | 2009/028655 | 3/2009 |
| WO | 2009/136663 | 11/2009 |
| WO | 2010/064722 | 6/2010 |

OTHER PUBLICATIONS

Banker (Modern Pharmaceutics) Banker, G.S. et al, Modern Pharmaceutics, 3ed., Marcel Dekker, New York, 1996, pp. 451 and 596.*

Wolff, Manfred E. "Burger's Medicinal Chemistry, 5ed, Part I", John Wiley & Sons, 1995, pp. 975-977.*

Johnson, et. al. "Relationships between drug activity in NCI preclinical in vitro and in vivo models and early clinical trials." British Journal of Cancer 2001, 84, 1424-1431.*

Roberts et. al. "Targeting the Raf-MEK-ERK mitogen-activated protein kinase cascade for the treatment of cancer." Oncogene (2007) 26, 3291-3310.*

Simone, Oncology: Introduction, Cecil Textbook of Medicine, 20th Edition, 1996 vol. 1, pp. 1004-1010.*

Hasegawa, et al., "Discovery of Novel Benzimidazoles as Potent Inhibitors of TIE-2 and VEGFR-2 Tyrosine Kinase Receptors", J. Med. Chem., vol. 50, No. 18, Apr. 2007, pp. 4453-4470.

Stella, et al., "Prodrug strategies to overcome poor water solubility", Advanced Drug Delivery Reviews, vol. 59, 2007, pp. 677-694.

Patani, et al., "Bioisosteris: A Rational Approach in Drug Design", Chem. Rev., vol. 96, 1996, pp. 3147-3176.

Lowinger, et al., "Design and Discovery of Small Molecules Targeting Raf-1 Kinase", Current Pharmaceutical Design, vol. 8, 2002, pp. 2269-2278.

Aly, et al., "New polymer syntheses IV. Synthesis and characterization of new polyamides containing bis-benzthiazolyl sulphone units in the main chain" High Perform. Polym., vol. 8, No. 2, 1996, pp. 307-314.

Takubo, et al., "Syntheses of Diaryl Sulfone. IV.", Yakugaku Zasshi, vol. 78, 1958, pp. 482-485.

Srivastava, et al., "Studies in antiparasitic agents: Part 20—Synthesis of probenzimidazoles, benzimidazoles and pyrimido[1,2-α]benzimidazoles as possible anthelmintics", Indian Journal of Chemistry, Section B: Organic Chemistry including Medicinal Chemistry, vol. 32B, No. 10, Oct. 1993, pp. 1035-1044.

Singh, et al., "Chemotherapy of Filariasis—On the Search of New Agents Effective on the Reproductive System of Female Adult Worms", Zeitschrift fuer Naturforschung, C: Journal of Biosciences, vol. 45, No. 11-12, 1990, pp. 1210-1214.

Naim, et al., "Studies in antiparasitic agents: Part 11—Synthesis of 5-substituted 2-aklyl/aryl-carbonylaminobenzimidazoles as orally effective anthelmintics", Indian Journal of Chemistry, Section B: Organic Chemistry including Medicinal Chemistry, vol. 29B, No. 5, 1990, pp. 464-470.

Naim, et al., "Studies in antiparasitic agents: Part 17,—Synthesis of 2-acylamino-6-substituted-benzthiazoles as potential anthelmintic agents", Indian Journal of Chemistry, vol. 30B, May 1991, pp. 494-498.

Folkman, Judah, "Tumor Angiogenesis: Therapeutic Implications", The New England Journal of Medicine, vol. 285, No. 21, Nov. 18, 1971, 1182-1186.

Ferrara, et al., "The Biology of Vascular Endothelial Growth Factor", Endocrine Reviews, vol. 18, No. 1, Feb., 1997, 4-25.

Matter, Alex, "Tumor angiogenesis as a therapeutic target", Drug Discovery Today, vol. 6, No. 19, Oct. 2001, 1005-1024.

Cannon, "Analog Design" in Burger's Medicinal Chemistry and Drug discovery, 6$^{th}$ ed. 2003, Wiley, pp. 687-714.

Das, et al., "Dithiocarbamate and CuO promoted one-pot synthesis of 2-(N-substituted)-aminobenzimidazoles and related heterocycles" Tetrahedron Letters, vol. 49, No. 6, 2008, pp. 992-995.

STN Search Result by Applicants—466 pages, Nov. 2006.

* cited by examiner

SEQUENCE LISTING

```
<160> NUMBER OF SEQ ID NOS: 10

<210> SEQ ID NO 1
<211> LENGTH: 64
<212> TYPE: DNA
<213> ORGANISM: Artificial Sequence
<220> FEATURE:
<223> OTHER INFORMATION: primer for cloning human BRAF gene

<400> SEQUENCE: 1
aaagaattca ccatggacta caaggacgac gatgacaaga ccccccctgc ctcattacct    60
ggct                                                                 64

<210> SEQ ID NO 2
```

```
<211> LENGTH: 35
<212> TYPE: DNA
<213> ORGANISM: Artificial Sequence
<220> FEATURE:
<223> OTHER INFORMATION: primer for cloning human BRAF gene

<400> SEQUENCE: 2
aaaagtcgac tcagtggaca ggaaacgcac catat                              35

<210> SEQ ID NO 3
<211> LENGTH: 29
<212> TYPE: DNA
<213> ORGANISM: Artificial Sequence
<220> FEATURE:
<223> OTHER INFORMATION: primer for cloning human BRAF gene

<400> SEQUENCE: 3
ggtctagcta cagagaaatc tcgatggag                                    29

<210> SEQ ID NO 4
<211> LENGTH: 29
<212> TYPE: DNA
<213> ORGANISM: Artificial Sequence
<220> FEATURE:
<223> OTHER INFORMATION: primer for cloning human BRAF gene

<400> SEQUENCE: 4
ctccatcgag atttctctgt agctagacc                                    29

<210> SEQ ID NO 5
<211> LENGTH: 31
<212> TYPE: DNA
<213> ORGANISM: Artificial Sequence
<220> FEATURE:
<223> OTHER INFORMATION: primer for cloning human GSTP1 gene

<400> SEQUENCE: 5
atatgctagc accatgccgc cctacaccgt g                                 31

<210> SEQ ID NO 6
<211> LENGTH: 32
<212> TYPE: DNA
<213> ORGANISM: Artificial Sequence
<220> FEATURE:
<223> OTHER INFORMATION: primer for cloning human GSTP1 gene

<400> SEQUENCE: 6
tataaagctt ctgtttcccg ttgccattga tg                                32

<210> SEQ ID NO 7
<211> LENGTH: 42
<212> TYPE: DNA
<213> ORGANISM: Artificial Sequence
<220> FEATURE:
<223> OTHER INFORMATION: synthetic DNA for PreScission protease
      recognition site

<400> SEQUENCE: 7
agcttggagg tggactggaa gttctgttcc aggggcccct gg                     42

<210> SEQ ID NO 8
<211> LENGTH: 42
<212> TYPE: DNA
<213> ORGANISM: Artificial Sequence
<220> FEATURE:
<223> OTHER INFORMATION: synthetic DNA for PreScission protease
      recognition site
```

```
<400> SEQUENCE: 8
gatcccaggg gcccctggaa cagaacttcc agtccacctc ca                  42

<210> SEQ ID NO 9
<211> LENGTH: 38
<212> TYPE: DNA
<213> ORGANISM: Artificial Sequence
<220> FEATURE:
<223> OTHER INFORMATION: primer for cloning human MEK1 gene

<400> SEQUENCE: 9
aaaagtcgac atgcccaaga agaagccgac gcccatcc                       38

<210> SEQ ID NO 10
<211> LENGTH: 37
<212> TYPE: DNA
<213> ORGANISM: Artificial Sequence
<220> FEATURE:
<223> OTHER INFORMATION: primer for cloning human MEK1 gene

<400> SEQUENCE: 10
ttttgcggcc gcaggggact cgctctttgt tgcttcc                        37
```

HETEROCYCLIC COMPOUND AND USE THEREOF

TECHNICAL FIELD

The present invention relates to a heterocyclic compound and use thereof, and in detail, relates to a heterocyclic compound having strong Raf inhibitory activity and useful for the prophylaxis or treatment and the like of cancer, and use thereof.

BACKGROUND OF THE INVENTION

Many activities of cancer cells such as growth, metastasis, invasion and the like are caused via intracellular signal transduction from RTK: receptor tyrosine kinases (EGFR, HER2 etc.), which is activated by stimulation by growth factors and mutation, and the activation signal thereof is transmitted downstream via RAS protein. As the intracellular signal transduction pathway via Ras, Ras/Raf/MEK/ERK pathway is best known, which is deeply involved in the control of various cell functions such as cell proliferation, cellular motility, transformation, apoptosis (cell death) resistance and the like.

To block the pathway, inhibitors of growth factor receptors, for example, epithelial growth factor receptor (EGFR) inhibitors gefinitib (trade name: Iressa), and erlotinib (trade name: Tarceva), and human epithelial growth factor receptor type 2 (HER2) inhibitory antibody trastuzumab (trade name: Herceptin) are placed on the market in recent years. They have been reported to be effective for the treatment of some cancer types in clinical practices, such as lung cancer, breast cancer and the like. In addition, it has been shown that inhibitory antibody bevacizumab (trade name: Avastin) against vascular endothelial growth factor (VEGF) inhibits activation of VEGFR in the intratumoral neovascular endothelial cells and shows an antitumor activity. These medicaments suppress signal transduction system at the downstream when showing a tumor growth inhibitory activity in cancer to be the target cells and vascular endothelial cells, through inhibition of receptor enzyme activity and inhibition of receptor activation.

On the other hand, the Ras/Raf/MEK/ERK pathway is well known to cause highly frequent mutations in cancer. Ras gene is reported to undergo an activation type mutation at codon 12, 13 or 61 of various carcinomas, for example, about 90% of the total of pancreatic cancer, about 35% of non-small cell lung cancer, about 30% of liver cancer and the like, and there are many reports on the correlation between Ras mutation and developing malignant tumor.

With regard to Raf gene, activation mutation in kinase domain of B-Raf in cancer has been reported. It is known that B-Raf mutation, particularly V600E, occurs in various carcinomas, for example, about 60% of the total of malignant melanoma, about 30% of thyroid cancer, about 15% of colorectal cancer and the like. Particularly, B-Raf (V600E) kinase has about 13-fold MEK phosphorylation activity as compared to wild-type B-Raf kinase, and the activity of B-Raf is deeply involved in the growth of cancer having a mutation in B-Raf.

In these cancers, inhibitions of the upstream growth factor receptor activity and Ras cannot suppress signal transduction system downstream of Raf kinase, which is constantly activated. In this case, since suppression of the downstream signal (Raf/MEK/ERK signal transduction system) cannot be expected, a tumor growth suppressive activity cannot be expected, either. For example, melanoma showing highly frequent B-Raf mutation is highly metastatic and the 5 year survival rate is about 6%, for which no promising therapeutic drug exists at present.

In the Ras/Raf/MEK/ERK pathway, Raf kinase is the most downstream molecule to be activated by mutation. A compound inhibiting Raf activity is considered to be effective as a therapeutic drug for any cancer caused by mutation of growth factor receptor or excessive activation by ligand stimulation, or cancer caused by activation type mutation of Ras.

Raf is a serine/threonine kinase, and is known to include three isoforms of A-Raf, B-Raf and c-Raf. Raf is activated by Ras and phosphorylates the downstream molecule MEK. The activated MEK further phosphorylates ERK to transmit the signal further downstream. Of three isoforms, B-Raf kinase shows an extreme strong activity of phosphorylating MEK in the basal state, which is about 15- to 20-fold that of A-Raf, c-Raf kinase activity. To undergo process of activation, moreover, c-Raf requires phosphorylation of the 338th serine in the activation loop to obtain the maximum activity (same for A-Raf). However, B-Raf is known to be easily activated as compared to A-Raf and c-Raf, since the corresponding sequence is always phosphorylated.

A compound that inhibits B-Raf kinase activity and mutant B-Raf kinase is considered to suppress cell proliferation particularly in cancer with poor prognosis. Accordingly, such compound becomes an effective therapeutic drug for cancer for which a growth factor receptor enzyme activity inhibitor is ineffective.

As Raf inhibitors, sorafenib-related derivatives (patent documents 1-3, non-patent document 1), benzylidene derivative (patent document 4), imidazole derivatives (patent documents 5-8), pyridylfuran derivatives (patent documents 9-12), benzazole derivatives (patent documents 13-15), thiazolopyridine derivatives (patent documents 16 and 17) and the like are known.

DOCUMENT LIST

Patent Documents patent document 1: WO2000/42012
patent document 2: WO2000/41698
patent document 3: WO2002/62763
patent document 4: WO99/10325
patent document 5: WO2002/94808
patent document 6: WO2002/24680
patent document 7: WO2001/66540
patent document 8: WO2001/66539
patent document 9: WO2003/22838
patent document 10: WO2003/22837
patent document 11: WO2003/22836
patent document 12: WO2003/22833
patent document 13: WO2003/082272
patent document 14: WO2005/032548
patent document 15: WO2007/030377
patent document 16: WO2006/071035
patent document 17: WO2007/058482

Non-Patent Document non-patent document 1: Current Pharmaceutical Design, 2000, 8, 2269-2278

SUMMARY OF THE INVENTION

Problems to be Solved by the Invention

A Raf inhibitor superior in the efficacy expression, pharmacokinetics, solubility, interaction with other pharmaceutical products, safety (low toxicity) and stability is expected to show a therapeutically superior effect. At present, however, no substance has been found that sufficiently satisfies the above requirements. Accordingly, it is an object of the present invention to provide a compound superior in the above-mentioned points and sufficiently satisfactory as a pharmaceutical product.

Means of Solving the Problems

The present inventors have conducted intensive studies in an attempt to solve the above-mentioned problems and found that a compound represented by the following formula has a superior Raf inhibitory activity, which resulted in the completion of the present invention.

Accordingly, the present invention provides the following.

[1] A compound represented by the formula

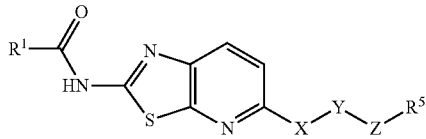

(I)

wherein
$R^1$ is a $C_{1-6}$ alkyl group optionally having substituent (s), a $C_{3-8}$ cycloalkyl group optionally having substituent(s), or a heterocyclic group optionally having substituent(s);
X is —O— or —$NR^2$— wherein $R^2$ is a hydrogen atom or a $C_{1-6}$ alkyl group;
Y is

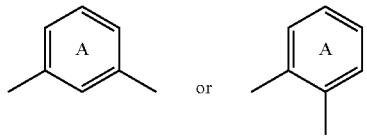

wherein ring A is a benzene ring which is optionally further substituted;
Z is
(1) —$NR^3CO$—$W^1$—,
(2) —$NR^3CO$—$W^1$—O—,
(3) —$NR^3CO$—$W^1$—O—$W^2$—,
(4) —$NR^3CO$—$W^1$—S—,
(5) —$NR^3CO$—$W^1$—$NR^4$—,
(6) —$NR^3COO$—,
(7) —$NR^3COO$—$W^1$—,
(8) —$NR^3CO$—CO—,
(9) —$NR^3CONR^4$—,
(10) —$NR^3CONR^4$—$W^1$—, or
(11) —$NR^3CONR^4$—$W^1$—O—
wherein $R^3$ and $R^4$ are each independently a hydrogen atom or a $C_{1-6}$ alkyl group,
$W^1$ and $W^2$ are each independently a $C_{1-6}$ alkylene group optionally having substituent(s), a $C_{2-6}$ alkenylene group optionally having substituent(s), a $C_{2-6}$ alkynylene group optionally having substituent(s), or a $C_{3-6}$ cycloalkylene group optionally having substituent(s); and $R^5$ is a 5- or 6-membered ring group optionally having substituent(s),
or a salt thereof (to be sometimes abbreviated as "compound (1)" in the present specification);
[2] the compound of the above-mentioned [1], wherein $R^1$ is cyclopropyl;
[3] the compound of the above-mentioned [1] or [2], wherein X is —O—, —NH— or —$N(CH_3)$—;
[4] the compound of any of the above-mentioned [1] to [3], wherein Y is

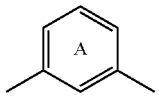

wherein ring A is a benzene ring optionally having 1 to 3 substituents selected from
(1) $C_{1-6}$ alkyl, and
(2) a halogen atom;
[5] the compound of any of the above-mentioned [1] to [4], wherein Z is
(1) —NHCO—$W^{1a}$—
  wherein $W^{1a}$ is
   (i) a $C_{1-6}$ alkylene group optionally having 1 to 3 substituents selected from
      (a) amino and
      (b) $C_{1-6}$ alkoxy,
   (ii) a $C_{2-6}$ alkenylene group,
   (iii) a $C_{2-6}$ alkynylene group or
   (iv) a $C_{3-6}$ cycloalkylene group,
(2) —NHCO—$W^{1b}$—O—
  wherein $W^{1b}$ is a $C_{1-6}$ alkylene group,
(3) —NHCO—$W^{1c}$—O—$W^{2c}$—
  wherein $W^{1c}$ is a $C_{1-6}$ alkylene group,
  $W^{2c}$ is a $C_{1-6}$ alkylene group,
(4) —NHCO—$W^{1d}$—S—
  wherein $W^{1d}$ is a $C_{1-6}$ alkylene group,
(5) —NHCO—$W^{1e}$—NH—
  wherein $W^{1e}$ is a $C_{1-6}$ alkylene group,
(6) —NHCOO—$W^{1g}$—
  wherein $W^{1g}$ is a $C_{1-6}$ alkylene group,
(7) —NHCO—CO—,
(8) —NHCONH—,
(9) —NHCONH—$W^{1j}$—
  wherein $W^{1j}$ is
   (i) a $C_{1-6}$ alkylene group or
   (ii) a $C_{3-6}$ cycloalkylene group, or
(10) —NHCONH—$W^{1k}$—O—
  wherein $W^{1k}$ is a $C_{1-6}$ alkylene group;
[6] the compound of any of the above-mentioned [1] to [5], wherein $R^5$ is
(1) cyclohexyl,
(2) phenyl optionally having 1 to 3 substituents selected from
   (a) a halogen atom,
   (b) $C_{1-6}$ alkyl optionally having 1 to 3 halogen atoms, and
   (c) $C_{1-6}$ alkoxy optionally having 1 to 3 halogen atoms,
(3) a 5- or 6-membered monocyclic aromatic heterocyclic group optionally having 1 to 3 substituents selected from
   (a) $C_{1-6}$ alkyl optionally having 1 to 3 halogen atoms and
   (b) phenyl, or
(4) a 5- or 6-membered monocyclic nonaromatic heterocyclic group;
[7] N-{5-[4-fluoro-3-({[2-(trifluoromethyl)phenyl]acetyl}amino)phenoxy][1,3]thiazolo-[5,4-b]pyridin-2-yl}cyclopropanecarboxamide, or a salt thereof;

[8] N-{5-[4-fluoro-3-({[4-(trifluoromethyl)phenyl]acetyl}amino)phenoxy][1,3]thiazolo-[5,4-b]pyridin-2-yl}cyclopropanecarboxamide, or a salt thereof;
[9] N-{5-[4-fluoro-3-({[3-(trifluoromethyl)phenyl]acetyl}amino)phenoxy][1,3]thiazolo-[5,4-b]pyridin-2-yl}cyclopropanecarboxamide, or a salt thereof;
[10] N-{5-[4-fluoro-3-({[3-(trifluoromethyl)phenyl]carbamoyl}amino)phenoxy][1,3]thiazolo-[5,4-b]pyridin-2-yl}cyclopropanecarboxamide, or a salt thereof;
[11] N-{5-[4-fluoro-3-({[6-(trifluoromethyl)pyridin-3-yl]carbamoyl}amino)phenoxy][1,3]thiazolo[5,4-b]pyridin-2-yl}cyclopropanecarboxamide, or a salt thereof;
[12] a prodrug of the compound of the above-mentioned [1];
[13] a medicament comprising the compound according to any of the above-mentioned [1] to [6] or a prodrug thereof;
[14] the medicament of the above-mentioned [13], which is a Raf inhibitor;
[15] the medicament of the above-mentioned [13], which is a prophylactic or therapeutic drug for cancer;
[16] a method of inhibiting Raf, comprising administering an effective amount of the compound of any of the above-mentioned [1] to [6] or a prodrug thereof to a mammal;
[17] a method of preventing or treating cancer, comprising administering an effective amount of the compound of any of the above-mentioned [1] to [6] or a prodrug thereof to a mammal;
[18] use of the compound of any of the above-mentioned [1] to [6] or a prodrug thereof for the production of a Raf inhibitor; and
[19] use of the compound of any of the above-mentioned [1] to [6] or a prodrug thereof for the production of a prophylactic or therapeutic drug for cancer.

Effect of the Invention

The compound of the present invention has a strong Raf inhibitory activity (particularly, B-Raf inhibitory activity) and can provide a clinically useful drug for the prophylaxis or treatment of cancer, a cancer growth inhibitor and a cancer metastasis suppressive agent.

DETAILED DESCRIPTION OF THE INVENTION

In the present specification, the "halogen atom" is a fluorine atom, a chlorine atom, a bromine atom or an iodine atom.

In the present specification, the "$C_{1-6}$ alkyl (group)" includes, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

In the present specification, the "$C_{2-6}$ alkenyl (group)" includes, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like.

In the present specification, the "$C_{2-6}$ alkynyl (group)" includes, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

In the present specification, the "$C_{1-6}$ alkoxy (group)" includes, for example, methoxy, ethoxy, propoxy, isopropoxy, butoxy, isobutoxy, sec-butoxy, tert-butoxy, pentoxy, isopentoxy, hexoxy and the like.

In the present specification, the "$C_{3-8}$ cycloalkyl (group)" includes, for example, cyclopropyl, cyclobutyl, cyclopentyl, cyclohexyl, cycloheptyl, cyclooctyl and the like.

In the present specification, the "$C_{3-8}$ cycloalkenyl (group)" includes, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) and the like.

In the present specification, the "$C_{6-10}$ aryl (group)" includes, for example, phenyl, 1-naphthyl, 2-naphthyl and the like.

In the present specification, the "heterocyclic group" includes an aromatic heterocyclic group and a nonaromatic heterocyclic group.

In the present specification, the "aromatic heterocyclic group" includes a monocyclic aromatic heterocyclic group and a condensed aromatic heterocyclic group.

Examples of the "monocyclic aromatic heterocyclic group" include a 5- to 7-membered (preferably, 5- or 6-membered) monocyclic aromatic heterocyclic group containing, as a ring-constituting atom besides carbon atom, 1 to 4 hetero atoms selected from oxygen atom, sulfur atom (optionally oxidized) and nitrogen atom (optionally oxidized), such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

Examples of the "condensed aromatic heterocyclic group" include 8- to 12-membered condensed aromatic heterocyclic group, specifically, a group wherein the above-mentioned 5- to 7-membered monocyclic aromatic heterocyclic group and $C_{6-10}$ aryl are condensed; and a group wherein the above-mentioned 5- to 7-membered monocyclic aromatic heterocyclic groups are condensed, such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

In the present specification, the "nonaromatic heterocyclic group" includes a monocyclic nonaromatic heterocyclic group and a condensed nonaromatic heterocyclic group.

Examples of the "monocyclic nonaromatic heterocyclic group" include a 3- to 8-membered (preferably, 5- or 6-membered) monocyclic nonaromatic heterocyclic group containing, as a ring-constituting atom besides carbon atom, 1 to 4 hetero atoms selected from oxygen atom, sulfur atom (optionally oxidized) and nitrogen atom, such as azetidinyl (e.g., 1-azetidinyl, 2-azetidinyl), pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., tetrahydropyridin-1-yl, tetrahydropyridin-2-yl, tetrahydropyridin-3-yl, tetrahydropyridin-4-yl) and the like.

Examples of the "condensed nonaromatic heterocyclic group" include a 8- to 12-membered condensed nonaromatic heterocyclic group, specifically, a group wherein the above-mentioned 3- to 8-membered monocyclic nonaromatic heterocyclic group and $C_{6-10}$ aryl are condensed; a group wherein the above-mentioned 3- to 8-membered monocyclic nonaromatic heterocyclic groups are condensed; a group wherein the above-mentioned 3- to 8-membered monocyclic nonaromatic heterocyclic group and the above-mentioned 5- to 7-membered monocyclic aromatic heterocyclic group are condensed; a group obtained by partial saturation of these groups, such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like.

In the present specification, the "$C_{1-6}$ alkylene group" includes, for example, —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(C$_2$H$_5$)—, —CH(C$_3$H$_7$)—, —CH(CH(CH$_3$)$_2$)—, —(CH(CH$_3$))$_2$—, —CH$_2$—CH(CH$_3$)—, —CH(CH$_3$)—CH$_2$—, —CH$_2$—CH$_2$—C(CH$_3$)$_2$—, —C(CH$_3$)$_2$—CH$_2$—CH$_2$—, —CH$_2$—CH$_2$—C(CH$_3$)$_2$—, —C(CH$_3$)$_2$—CH$_2$—CH$_2$—CH$_2$— and the like.

In the present specification, the "$C_{2-6}$ alkenylene group" includes, for example, —CH=CH—, —CH$_2$—CH=CH—, —CH=CH—CH$_2$—, —C(CH$_3$)$_2$—CH=CH—, —CH=CH—C(CH$_3$)$_2$—, —CH$_2$—CH=CH—CH$_2$—, —CH$_2$—CH$_2$—CH=CH—, —CH=CH—CH$_2$—CH$_2$—, —CH=CH—CH=CH—, —CH=CH—CH$_2$—CH$_2$—CH$_2$—, —CH$_2$—CH$_2$—CH$_2$—CH=CH— and the like.

In the present specification, the "$C_{2-6}$ alkynylene group" includes, for example, —C≡C—, —CH$_2$—C≡C—, —C≡C—CH$_2$—, —C(CH$_3$)$_2$—, —C≡C—, —C≡C—C(CH$_3$)$_2$—, —CH$_2$—C≡C—CH$_2$—, —C≡C—CH$_2$—CH$_2$—, —C≡C—C≡C—, —C≡C—CH$_2$—CH$_2$—CH$_2$—, —CH$_2$—CH$_2$—CH$_2$—C≡C— and the like.

In the present specification, the "$C_{3-6}$ cycloalkylene group" includes, for example, cyclopropylene, cyclobutylene (e.g., 1,2-cyclobutylene, 1,3-cyclobutylene), cyclopentylene (e.g., 1,2-cyclopentylene, 1,3-cyclopentylene), cyclohexylene (e.g., 1,2-cyclohexylene, 1,3-cyclohexylene, 1,4-cyclohexylene) and the like.

Each substituent of the formula (I) is explained in the following.

In the formula (I), $R^1$ is a $C_{1-6}$ alkyl group optionally having substituent(s), a $C_{3-8}$ cycloalkyl group optionally having substituent(s), or a heterocyclic group optionally having substituent(s).

The "$C_{1-6}$ alkyl group" of the "$C_{1-6}$ alkyl group optionally having substituent(s)" for $R^1$ optionally has 1 to 5 (preferably 1 to 3) substituents at substitutable positions. Examples of the substituent include substituents selected from the following substituent group A. When plural substituents are present, respective substituents may be the same or different.

Substituent group A:
(1) a halogen atom;
(2) cyano;
(3) nitro;
(4) hydroxy;
(5) $C_{3-8}$ cycloalkyl optionally having 1 to 3 substituents selected from
    (a) a halogen atom and
    (b) cyano;
(6) $C_{6-10}$ aryl (e.g., phenyl) optionally having 1 to 3 substituents selected from
    (a) a halogen atom and
    (b) cyano;
(7) $C_{1-6}$ alkoxy optionally having 1 to 4 (e.g., 1 to 3) substituents selected from
    (a) a halogen atom,
    (b) cyano,
    (c) $C_{3-8}$ cycloalkyl optionally having 1 to 3 halogen atoms,
    (d) $C_{3-8}$ cycloalkenyl optionally having 1 to 3 halogen atoms and
    (e) $C_{6-10}$ aryl optionally having 1 to 3 halogen atoms;
(8) $C_{2-6}$ alkenyloxy (e.g., ethenyloxy, propenyloxy, butenyloxy, pentenyloxy, hexenyloxy) optionally having 1 to 3 halogen atoms;

(9) C$_{2-6}$ alkynyloxy (e.g., ethynyloxy, propynyloxy, butynyloxy, pentynyloxy, hexynyloxy) optionally having 1 to 3 halogen atoms;
(10) C$_{3-8}$ cycloalkyloxy (e.g., cyclopropyloxy, cyclobutyloxy, cyclopentyloxy, cyclohexyloxy) optionally having 1 to 3 halogen atoms;
(11) C$_{3-8}$ cycloalkenyloxy (e.g., cyclopropenyloxy, cyclobutenyloxy, cyclopentenyloxy, cyclohexenyloxy) optionally having 1 to 3 halogen atoms;
(12) C$_{6-10}$ aryloxy (e.g., phenyloxy, 1-naphthyloxy, 2-naphthyloxy) optionally having 1 to 3 halogen atoms;
(13) C$_{1-6}$ alkylaminosulfonyl (e.g., methylaminosulfonyl, ethylaminosulfonyl, propylaminosulfonyl);
(14) di C$_{1-6}$ alkylaminosulfonyl (e.g., dimethylaminosulfonyl, diethylaminosulfonyl, dipropylaminosulfonyl);
(15) carbamoyl;
(16) C$_{1-6}$ alkylamino-carbonyl (e.g., methylaminocarbonyl, ethylaminocarbonyl, propylaminocarbonyl);
(17) di C$_{1-6}$ alkylamino-carbonyl (e.g., dimethylaminocarbonyl, diethylaminocarbonyl, dipropylaminocarbonyl);
(18) formyl;
(19) C$_{1-6}$ alkyl-carbonyl (e.g., acetyl, ethylcarbonyl, propylcarbonyl, isopropylcarbonyl);
(20) C$_{2-6}$ alkenyl-carbonyl (e.g., ethenylcarbonyl, propenylcarbonyl, butenylcarbonyl, pentenylcarbonyl, hexenylcarbonyl);
(21) C$_{2-6}$ alkynyl-carbonyl (e.g., ethynylcarbonyl, propynylcarbonyl, butynylcarbonyl, pentynylcarbonyl, hexynylcarbonyl);
(22) C$_{3-8}$ cycloalkyl-carbonyl (e.g., cyclopropylcarbonyl, cyclobutylcarbonyl, cyclopentylcarbonyl, cyclohexylcarbonyl);
(23) C$_{3-8}$ cycloalkenyl-carbonyl (e.g., cyclopropenylcarbonyl, cyclobutenylcarbonyl, cyclopentenylcarbonyl, cyclohexenylcarbonyl);
(24) C$_{6-10}$ aryl-carbonyl (e.g., benzoyl, 1-naphthylcarbonyl, 2-naphthylcarbonyl);
(25) C$_{3-8}$ cycloalkyl-C$_{1-6}$ alkyl-carbonyl (e.g., cyclopropylmethylcarbonyl, cyclopropylethylcarbonyl, cyclobutylmethylcarbonyl, cyclopentylmethylcarbonyl, cyclohexylmethylcarbonyl, cyclohexylethylcarbonyl);
(26) C$_{3-8}$ cycloalkenyl-C$_{1-6}$ alkyl-carbonyl (e.g., cyclopentenylmethylcarbonyl, cyclohexenylmethylcarbonyl, cyclohexenylethylcarbonyl, cyclohexenylpropylcarbonyl);
(27) C$_{6-10}$ aryl-C$_{1-6}$ alkyl-carbonyl (e.g., benzylcarbonyl, phenylethylcarbonyl);
(28) 5- or 6-membered monocyclic aromatic heterocyclylcarbonyl (e.g., furylcarbonyl, thienylcarbonyl, pyrrolylcarbonyl, oxazolylcarbonyl, isooxazolylcarbonyl, thiazolylcarbonyl, isothiazolylcarbonyl, imidazolylcarbonyl, pyridylcarbonyl, pyrazolylcarbonyl);
(29) 8- to 12-membered condensed aromatic heterocyclylcarbonyl (e.g., benzofurylcarbonyl, isobenzofurylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(30) 3- to 8-membered monocyclic non-aromatic heterocyclylcarbonyl (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidinylcarbonyl);
(31) C$_{1-6}$ alkylsulfonyl (e.g., methylsulfonyl, ethylsulfonyl);
(32) C$_{2-6}$ alkenylsulfonyl (e.g., ethenylsulfonyl, propenylsulfonyl);
(33) C$_{2-6}$ alkynylsulfonyl (e.g., ethynylsulfonyl, propynylsulfonyl);
(34) C$_{3-8}$ cycloalkylsulfonyl (e.g., cyclopropylsulfonyl, cyclobutylsulfonyl);
(35) C$_{3-8}$ cycloalkenylsulfonyl (e.g., cyclopropenylsulfonyl, cyclobutenylsulfonyl);
(36) C$_{8-10}$ arylsulfonyl (e.g., phenylsulfonyl);
(37) C$_{3-8}$ cycloalkyl-C$_{1-6}$ alkylsulfonyl (e.g., cyclopropylmethylsulfonyl);
(38) C$_{3-8}$ cycloalkenyl-C$_{1-6}$ alkylsulfonyl (e.g., cyclopentenylmethylsulfonyl);
(39) C$_{6-10}$ aryl-C$_{1-6}$ alkylsulfonyl (e.g., benzylsulfonyl);
(40) 5- or 6-membered monocyclic aromatic heterocyclylsulfonyl (e.g., furylsulfonyl, thienylsulfonyl, pyridylsulfonyl);
(41) 8- to 12-membered condensed aromatic heterocyclylsulfonyl (e.g., benzofurylsulfonyl, isobenzofurylsulfonyl);
(42) 3- to 8-membered monocyclic non-aromatic heterocyclylsulfonyl (e.g. oxiranylsulfonyl, azetidinylsulfonyl);
(43) amino;
(44) mono-C$_{1-6}$ alkylamino (e.g., methylamino, ethylamino, propylamino, isopropylamino, butylamino, isobutylamino, tert-butylamino);
(45) di-C$_{1-6}$ alkylamino (e.g., dimethylamino, diethylamino, dipropylamino, diisopropylamino, dibutylamino, diisobutylamino, di-tert-butylamino);
(46) mono(C$_{1-6}$ alkyl-carbonyl)amino (e.g., acetylamino, ethylcarbonylamino, propylcarbonylamino, tert-butylcarbonylamino) optionally having 1 to 3 halogen atoms;
(47) mono(C$_{3-8}$ cycloalkyl-carbonyl)amino (e.g., cyclopropylcarbonylamino, cyclobutylcarbonylamino, cyclopentylcarbonylamino, cyclohexylcarbonylamino);
(48) mono(C$_{6-10}$ aryl-carbonyl)amino (e.g., benzoylamino) optionally having 1 to 3 halogen atoms;
(49) mono(5- or 6-membered monocyclic aromatic heterocyclylcarbonyl)amino (e.g., furylcarbonylamino, thienylcarbonylamino, pyrrolylcarbonylamino, oxazolylcarbonylamino, isooxazolylcarbonylamino, thiazolylcarbonylamino, isothiazolylcarbonylamino, imidazolylcarbonylamino, pyridylcarbonylamino, pyrazolylcarbonylamino);
(50) mono(8- to 12-membered condensed aromatic heterocyclylcarbonyl)amino (e.g., benzofurylcarbonylamino, isobenzofurylcarbonylamino, benzothienylcarbonylamino, isobenzothienylcarbonylamino);
(51) mono(3- to 8-membered monocyclic non-aromatic heterocyclyl-carbonyl)amino (e.g., oxetanylcarbonylamino, azetidinylcarbonylamino, oxetanylcarbonylamino);
(52) thiol;
(53) C$_{1-6}$ alkylsulfanyl (e.g., methylsulfanyl, ethylsulfanyl);
(54) C$_{2-6}$ alkenylsulfanyl (e.g., ethenylsulfanyl, propenylsulfanyl);
(55) C$_{2-6}$ alkynylsulfanyl (e.g., ethynylsulfanyl, propynylsulfanyl);
(56) C$_{3-8}$ cycloalkylsulfanyl (e.g., cyclopropylsulfanyl, cyclobutylsulfanyl);
(57) C$_{3-8}$ cycloalkenylsulfanyl (e.g., cyclopropenylsulfanyl, cyclobutenylsulfanyl);
(58) C$_{6-10}$ arylsulfanyl (e.g., phenylsulfanyl);
(59) C$_{3-8}$ cycloalkyl-C$_{1-6}$ alkylsulfanyl (e.g., cyclopropylmethylsulfanyl);
(60) C$_{3-8}$ cycloalkenyl-C$_{1-6}$ alkylsulfanyl (e.g., cyclopentenylmethylsulfanyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl);
(62) a 8- to 12-membered condensed aromatic heterocyclic group (e.g., benzofuryl, isobenzofuryl, benzothienyl, isobenzothienyl, indolyl, isoindolyl, indazolyl, benzimidazolyl, benzoxazolyl);

(63) a 3- to 8-membered monocyclic nonaromatic heterocyclic group (e.g., oxiranyl, azetidinyl, oxetanyl, thietanyl, pyrrolidinyl, tetrahydrofuryl, thiolanyl, piperidinyl);
(64) 5- or 6-membered monocyclic aromatic heterocyclyloxy (e.g., furyloxy, thienyloxy, pyrrolyloxy, oxazolyloxy, isooxazolyloxy, thiazolyloxy, isothiazolyloxy, imidazolyloxy, pyridyloxy, pyrazolyloxy);
(65) 8- to 12-membered condensed aromatic heterocyclyloxy (e.g., benzofuryloxy, isobenzofuryloxy, benzothienyloxy, isobenzothienyloxy, indolyloxy, isoindolyloxy, indazolyloxy, benzimidazolyloxy, benzoxazolyloxy);
(66) 3- to 8-membered monocyclic non-aromatic heterocyclyloxy (e.g., oxetanyloxy, azetidinyloxy, oxetanyloxy, thietanyloxy, pyrrolidinyloxy, tetrahydrofuryloxy, thiolanyloxy, piperidinyloxy);
(67) $C_{1-6}$ alkylsulfinyl (e.g., methylsulfinyl, ethylsulfinyl);
(68) $C_{2-6}$ alkenylsulfinyl (e.g., ethenylsulfinyl, propenylsulfinyl);
(69) $C_{2-6}$ alkynylsulfinyl (e.g., ethynylsulfinyl, propynylsulfinyl);
(70) $C_{3-8}$ cycloalkylsulfinyl (e.g., cyclopropylsulfinyl, cyclobutylsulfinyl);
(71) $C_{3-8}$ cycloalkenylsulfinyl (e.g., cyclopropenylsulfinyl, cyclobutenylsulfinyl);
(72) $C_{6-10}$ arylsulfinyl (e.g., phenylsulfinyl);
(73) $C_{3-8}$ cycloalkyl-$C_{1-6}$ alkylsulfinyl (e.g., cyclopropylmethylsulfinyl);
(74) $C_{3-8}$ cycloalkenyl-$C_{1-6}$ alkylsulfinyl (e.g., cyclopentenylmethylsulfinyl);
(75) $C_{1-6}$ alkylamino-thiocarbonyl (e.g., methylaminothiocarbonyl, ethylaminothiocarbonyl, propylaminothiocarbonyl);
(76) di $C_{1-6}$ alkylamino-thiocarbonyl (e.g., dimethylaminothiocarbonyl, diethylaminothiocarbonyl, dipropylaminothiocarbonyl);
(77) carboxy;
(78) $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, tert-butoxycarbonyl);
(79) $C_{2-6}$ alkenyloxy-carbonyl (e.g., ethenyloxycarbonyl, propenyloxycarbonyl, butenyloxycarbonyl, pentenyloxycarbonyl, hexenyloxycarbonyl);
(80) $C_{2-6}$ alkynyloxy-carbonyl (e.g., ethynyloxycarbonyl, propynyloxycarbonyl, but ynyloxycarbonyl, pent ynyloxycarbonyl, hexynyloxycarbonyl);
(81) $C_{3-8}$ cycloalkyloxy-carbonyl (e.g., cyclopropyloxycarbonyl, cyclobutyloxycarbonyl, cyclopentyloxycarbonyl, cyclohexyloxycarbonyl);
(82) $C_{3-8}$ cycloalkenyloxy-carbonyl (e.g., cyclopropenyloxycarbonyl, cyclobutenyloxycarbonyl, cyclopentenyloxycarbonyl, cyclohexenyloxycarbonyl);
(83) $C_{6-10}$ aryloxy-carbonyl (e.g., phenyloxycarbonyl, 1-naphthyloxycarbonyl, 2-naphthyloxycarbonyl);
(84) $C_{3-8}$ cycloalkyl-$C_{1-6}$ alkoxy-carbonyl (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl);
(85) $C_{3-8}$ cycloalkenyl-$C_{1-6}$ alkoxy-carbonyl (e.g., cyclopentenylmethyloxycarbonyl, cyclohexenylmethyloxycarbonyl, cyclohexenylethyloxycarbonyl, cyclohexenylpropyloxycarbonyl); and
(86) $C_{6-10}$ aryl-$C_{1-6}$ alkoxy-carbonyl (e.g., phenylmethyloxycarbonyl, phenylethyloxycarbonyl).

The "$C_{3-8}$ cycloalkyl group" of the "$C_{3-8}$ cycloalkyl group optionally having substituent(s)" for $R^1$ optionally has 1 to 5 (preferably 1 to 3) substituents at substitutable positions. Examples of such substituent include substituents selected from
(1) $C_{1-6}$ alkyl optionally having 1 to 3 substituents selected from a halogen atom and cyano;
(2) oxo; and
(3) the aforementioned substituent group A. When plural substituents are present, respective substituents may be the same or different.

Examples of the "heterocyclic group" of the "heterocyclic group optionally having substituent(s)" for $R^1$ include an aromatic heterocyclic group (e.g., 5- to 7-membered (preferably 5- or 6-membered) monocyclic aromatic heterocyclic group, 8- to 12-membered condensed aromatic heterocyclic group), and a nonaromatic heterocyclic group (e.g., a 3- to 8-membered (preferably 5- or 6-membered) monocyclic non-aromatic heterocyclic group, a 8- to 12-membered condensed nonaromatic heterocyclic group).

The "heterocyclic group" of the "heterocyclic group optionally having substituent(s)" for $R^1$ optionally has 1 to 5 (preferably 1 to 3) substituents at substitutable positions.

When the "heterocyclic group" is an aromatic heterocyclic group, examples of such substituent include substituents selected from
(1) $C_{1-8}$ alkyl optionally having 1 to 3 substituents selected from a halogen atom and cyano; and
(2) the aforementioned substituent group A. When plural substituents are present, respective substituents may be the same or different.

When the "heterocyclic group" is a nonaromatic heterocyclic group, examples of such substituent include substituents selected from
(1) $C_{1-8}$ alkyl optionally having 1 to 3 substituents selected from a halogen atom and cyano;
(2) oxo; and
(3) the aforementioned substituent group A. When plural substituents are present, respective substituents may be the same or different.

$R^1$ is preferably a $C_{3-8}$ cycloalkyl group optionally having substituent(s), more preferably, cyclopropyl optionally having substituent(s), further preferably cyclopropyl.

In the formula (I), X is —O— or —$NR^2$— wherein $R^2$ is a hydrogen atom or a $C_{1-6}$ alkyl group.

When X is —$NR^2$—, $R^2$ is preferably a hydrogen atom or methyl.

X is preferably —O—, —NH— or —N(CH$_3$)—.

X is further preferably —O—.

A compound wherein X is —O— has a high B-Raf inhibitory activity (intratumor pMEK suppressive activity, pERK suppressive activity etc.), and is particularly effective against colorectal cancer with increased malignancy due to B-Raf mutation.

In the formula (I), Y is

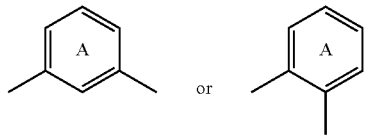

wherein ring A is a benzene ring optionally further substituted.

The benzene ring of the "optionally further substituted benzene ring" for ring A may further have, besides —X— group and —Z— group, 1 to 4 (preferably 1 to 3, more preferably 1) substituents at substitutable position(s). Examples of such substituent include those selected from
(1) $C_{1-6}$ alkyl optionally having 1 to 3 substituents selected from a halogen atom and cyano; and
(2) the aforementioned substituent group A. When plural substituents are present, they may be the same or different.

Ring A is preferably a benzene ring optionally having 1 to 3 (preferably 1) substituents selected from
(1) $C_{1-6}$ alkyl (particularly, methyl), and
(2) a halogen atom (particularly, fluorine atom, chlorine atom).

Y is preferably

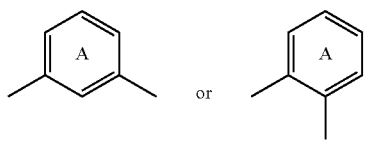

wherein ring A is a benzene ring optionally having 1 to 3 (preferably 1) substituents selected from
(1) $C_{1-6}$ alkyl (particularly, methyl), and
(2) a halogen atom (particularly, a fluorine atom, a chlorine atom), more preferably,

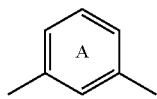

wherein ring A is a benzene ring optionally having 1 to 3 (preferably 1) substituents selected from
(1) $C_{1-6}$ alkyl (particularly, methyl), and
(2) a halogen atom (particularly, a fluorine atom, a chlorine atom), further preferably

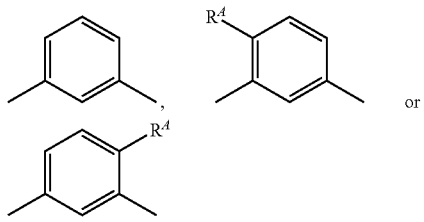

wherein $R^A$ is $C_{1-6}$ alkyl (particularly, methyl) or a halogen atom (particularly, a fluorine atom, a chlorine atom).

A compound wherein ring A is represented by

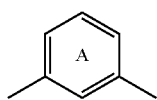

wherein ring A is a benzene ring optionally having 1 to 3 (preferably 1) substituents selected from
(1) $C_{1-6}$ alkyl (particularly, methyl), and
(2) a halogen atom (particularly, a fluorine atom, a chlorine atom)
has a high B-Raf inhibitory activity (intratumor pMEK suppressive activity, pERK suppressive activity etc.), and is particularly effective against colorectal cancer with increased malignancy due to B-Raf mutation.

In the formula (I), Z is
(1) —$NR^3CO$—$W^1$—,
(2) —$NR^3CO$—$W^1$—O—,
(3) —$NR^3CO$—$W^1$—O—$W^2$—,
(4) —$NR^3CO$—$W^1$—S—,
(5) —$NR^3CO$—$W^1$—$NR^4$—,
(6) —$NR^3COO$—,
(7) —$NR^3COO$—$W^1$—,
(8) —$NR^3CO$—CO—,
(9) —$NR^3CONR^4$—,
(10) —$NR^3CONR^4$—$W^1$—, or
(11) —$NR^3CONR^4$—$W^1$—O—
wherein $R^3$ and $R^4$ are each independently a hydrogen atom or a $C_{1-6}$ alkyl group, $W^1$ and $W^2$ are each independently a $C_{1-6}$ alkylene group optionally having substituent(s), a $C_{2-6}$ alkenylene group optionally having substituent(s), a $C_{2-6}$ alkynylene group optionally having substituent(s), or a $C_{3-6}$ cycloalkylene group optionally having substituent(s).

The "$C_{1-6}$ alkylene group" of the "$C_{1-6}$ alkylene group optionally having substituent(s)" for $W^1$ or $W^2$ optionally has 1 to 5 (preferably 1 to 3) substituents at substitutable positions. Examples of such substituent include substituents selected from the aforementioned substituent group A. When plural substituents are present, respective substituents may be the same or different.

The "$C_{2-6}$ alkenylene group" of the "$C_{2-6}$ alkenylene group optionally having substituent(s)" for $W^1$ or $W^2$ optionally has 1 to 5 (preferably 1 to 3) substituents at substitutable positions. Examples of such substituent include substituents selected from the aforementioned substituent group A. When plural substituents are present, respective substituents may be the same or different.

The "$C_{2-6}$ alkynylene group" of the "$C_{2-6}$ alkynylene group optionally having substituent(s)" for $W^1$ or $W^2$ optionally has 1 to 5 (preferably 1 to 3) substituents at substitutable positions. Examples of such substituent include substituents selected from the aforementioned substituent group A. When plural substituents are present, respective substituents may be the same or different.

The "$C_{3-6}$ cycloalkylene group" of the "$C_{3-6}$ cycloalkylene group optionally having substituent(s)" for $W^1$ or $W^2$ optionally has 1 to 5 (preferably 1 to 3) substituents at substitutable positions. Examples of such substituent include substituents selected from
(1) $C_{1-6}$ alkyl optionally having 1 to 3 substituents selected from a halogen atom and cyano;
(2) oxo; and
(3) the aforementioned substituent group A. When plural substituents are present, respective substituents may be the same or different.

Z is preferably
(1) —$NR^3CO$—$W^1$—,
(2) —$NR^3CO$—$W^1$—O—,
(3) —$NR^3CO$—$W^1$—O—$W^2$—,
(4) —$NR^3CO$—$W^1$—S—,
(5) —$NR^3CO$—$W^1$—$NR^4$—,
(6) —$NR^3COO$—$W^1$—,
(7) —$NR^3CO$—CO—,
(8) —$NR^3CONR^4$—,
(9) —$NR^3CONR^4$—$W^1$—, or
(10) —$NR^3CONR^4$—$W^1$—O— wherein each symbol is as defined above, and specific examples thereof include (1) —NHCO—$W^{1a}$—
  wherein $W^{1a}$ is a $C_{1-6}$ alkylene group optionally having 1 to 3 (preferably 1) substituents selected from
    (1) (a) amino, and
      (b) $C_{1-6}$ alkoxy (particularly, methoxy)
    (particularly, —$CH_2$—, —$(CH_2)_2$—)
    (ii) a $C_{2-6}$ alkenylene group (particularly, —CH=CH—),
    (iii) a $C_{2-6}$ alkynylene group (particularly, —C≡C—), or
    (iv) a $C_{3-6}$ cycloalkylene group (particularly, cyclopropylene);
(2) —NHCO—$W^{1b}$—O—
  wherein $W^{1b}$ is a $C_{1-6}$ alkylene group (particularly, —$CH_2$—, —$(CH_2)_2$—);
(3) —NHCO—$W^{1c}$—O—$W^{2c}$—
  wherein $W^{1c}$ is a $C_{1-6}$ alkylene group (particularly, —$CH_2$—, —$(CH_2)_2$—),
  $W^2$ is a $C_{1-6}$ alkylene group (particularly, —$CH_2$—, —$(CH_2)_2$—);
(4) —NHCO—$W^{1d}$—S—
  wherein $W^{1d}$ is a $C_{1-6}$ alkylene group (particularly, —$CH_2$—, —$(CH_2)_2$—);
(5) —NHCO—$W^{1e}$—NH—
  wherein $W^{1e}$ is a $C_{1-6}$ alkylene group (particularly, —$CH_2$—, —$(CH_2)_2$—);
(6) —NHCOO—$W^{1g}$—
  wherein $W^{1g}$ is a $C_{1-6}$ alkylene group (particularly, —$CH_2$—, —$(CH_2)_2$—);
(7) —NHCO—CO—;
(8) —NHCONH—;
(9) —NHCONH—$W^{1j}$—
  wherein $W^{1j}$ is
    (i) a $C_{1-6}$ alkylene group (particularly, —$CH_2$—, —$(CH_2)_2$—), or
    (ii) a $C_{3-6}$ cycloalkylene group (particularly, cyclopropylene); or
(10) —NHCONH—$W^{1k}$—O—
  wherein $W^{1k}$ is a $C_{1-6}$ alkylene group (particularly, —$CH_2$—, —$(CH_2)_2$—)—.

Z is more preferably
(1) —$NR^3CO$—$W^1$—, or
(2) —$NR^3CONR^4$
wherein each symbol is as defined above.

Z is more preferably —$NR^3CO$—$W^1$— wherein each symbol is as defined above, and —$NHCOCH_2$— is particularly preferable.

A compound wherein Z is —$NR^3CO$—$W^1$— wherein each symbol is as defined above (particularly a compound wherein Z is —$NHCOCH_2$—) has a superior property (particularly solubility).

In the formula (I), $R^5$ is a 5- or 6-membered ring group optionally having substituent(s).

Examples of the "5- or 6-membered ring group" of the "5- or 6-membered ring group optionally having substituent(s)" for $R^5$ include
(1) cyclopentyl,
(2) cyclohexyl,
(3) cyclopentenyl (e.g., 2-cyclopenten-1-yl, 3-cyclopenten-1-yl),
(4) cyclohexenyl (e.g., 2-cyclohexen-1-yl, 3-cyclohexen-1-yl),
(5) phenyl,
(6) a 5- or 6-membered monocyclic aromatic heterocyclic group (e.g., furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl, triazinyl),
(7) a 5- or 6-membered monocyclic nonaromatic heterocyclic group (e.g., pyrrolidinyl, piperidinyl, morpholinyl, thiomorpholinyl, piperazinyl, oxazolidinyl, thiazolidinyl, dihydrothiopyranyl, imidazolidinyl, oxazolinyl, thiazolinyl, imidazolinyl, dioxolyl, dioxolanyl, dihydrooxadiazolyl, pyranyl, tetrahydropyranyl, thiopyranyl, tetrahydrothiopyranyl, 1-oxidotetrahydrothiopyranyl, 1,1-dioxidotetrahydrothiopyranyl, tetrahydrofuryl, pyrazolidinyl, pyrazolinyl, tetrahydropyrimidinyl, dihydrotriazolyl, tetrahydrotriazolyl, dihydropyridyl, tetrahydropyridyl) and the like.

The "5- or 6-membered ring group" of the "5- or 6-membered ring group optionally having substituent(s)" for $R^5$ optionally has 1 to 5 (preferably 1 to 3) substituents at substitutable positions.

When the "5- or 6-membered ring group" is cyclopentenyl, cyclohexenyl, phenyl, or a 5- or 6-membered monocyclic aromatic heterocyclic group, examples of such substituent include substituents selected from
(1) $C_{1-6}$ alkyl optionally having 1 to 3 substituents selected from a halogen atom and cyano; and
(2) the aforementioned substituent group A. When plural substituents are present, respective substituents may be the same or different.

When the "5- or 6-membered ring group" is cyclopentyl, cyclohexyl or 5- or 6-membered monocyclic nonaromatic heterocyclic group, examples of such substituent include substituents selected from
(1) $C_{1-6}$ alkyl optionally having 1 to 3 substituents selected from a halogen atom and cyano;
(2) oxo; and
(3) the aforementioned substituent group A. When plural substituents are present, respective substituents may be the same or different.

$R^5$ is preferably
(1) cyclohexyl optionally having substituent(s),
(2) phenyl optionally having substituent(s),
(3) a 5- or 6-membered monocyclic aromatic heterocyclic group (particularly, thienyl, pyridyl, pyrazolyl) optionally having substituent(s), or
(4) a 5- or 6-membered monocyclic nonaromatic heterocyclic group (particularly, piperidinyl) optionally having substituent(s), more preferably,
(1) cyclohexyl;
(2) phenyl optionally having 1 to 3 (particularly, 1 or 2) substituents selected from
  (a) a halogen atom (particularly, a fluorine atom, a chlorine atom),
  (b) $C_{1-6}$ alkyl (particularly, methyl, tert-butyl) optionally having 1 to 3 halogen atoms (particularly, a fluorine atom), and
  (c) $C_{1-6}$ alkoxy (particularly, methoxy) optionally having 1 to 3 halogen atoms (particularly, a fluorine atom); PS (3) a 5- or 6-membered monocyclic aromatic heterocyclic group (particularly, thienyl, pyridyl, pyrazolyl) optionally having 1 to 3 (particularly 1) substituents selected from
  (a) $C_{1-6}$ alkyl (particularly, methyl, tert-butyl) optionally having 1 to 3 halogen atoms (particularly, a fluorine atom), and
  (b) phenyl; or
(4) a 5- or 6-membered monocyclic nonaromatic heterocyclic group (particularly, piperidinyl).

$R^5$ is more preferably phenyl optionally having a $C_{1-6}$ alkyl group (particularly, methyl, tert-butyl) optionally having 1 to 3 halogen atoms (particularly, a fluorine atom).

Specific preferable examples of compound (I) include the following.

Compound (A):

A compound of the formula (I), wherein
$R^1$ is $C_{3-8}$ cycloalkyl group optionally having substituent(s) (particularly, cyclopropyl optionally having substituent(s));
X is —O—, —NH— or —N(CH$_3$)—;
Y is

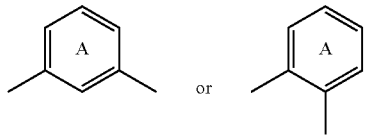

wherein ring A is a benzene ring optionally further substituted;
Z is
(1) —NR$^3$CO—W$^1$—,
(2) —NR$^3$CO—W$^1$—O—,
(3) —NR$^3$CO—W$^1$—O—W$^2$—,
(4) —NR$^3$CO—W$^1$—S—,
(5) —NR$^3$CO—W—NR$^4$—,
(6) —NR$^3$COO—W$^1$—,
(7) —NR$^3$CO—CO—,
(8) —NR$^3$CONR$^4$—,
(9) —NR$^3$CONR$^4$—W$^1$—, or
(10) —NR$^3$CONR$^4$—W$^1$—O—
wherein each symbol is as defined above; and
$R^5$ is
(1) cyclohexyl optionally having substituent(s),
(2) phenyl optionally having substituent(s),
(3) a 5- or 6-membered monocyclic aromatic heterocyclic group (particularly, thienyl, pyridyl, pyrazolyl) optionally having substituent(s), or
(4) a 5- or 6-membered monocyclic nonaromatic heterocyclic group (particularly, piperidinyl) optionally having substituent(s), or a salt thereof.

Compound (B):

A compound of the formula (I), wherein
$R^1$ is cyclopropyl;
X is —O—, —NH— or —N(CH$_3$)—;
Y is

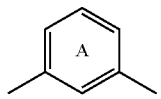

wherein ring A is a benzene ring optionally having 1 to 3 (preferably 1) substituents selected from
(1) $C_{1-6}$ alkyl (particularly, methyl), and
(2) halogen atom (particularly, a fluorine atom, a chlorine atom)
[preferably,
Y is

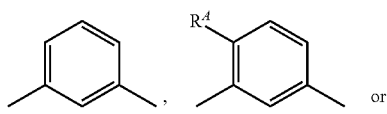

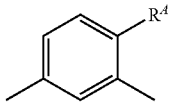

is wherein $R^A$ is $C_{1-6}$ alkyl (particularly, methyl) or a halogen atom (particularly, a fluorine atom, a chlorine atom)];
Z is
(1) —NHCO—W$^{1a}$—
(W$^{1a}$ is
(i) a $C_{1-6}$ alkylene group (particularly, —CH$_2$—, —(CH$_2$)$_2$—) optionally having 1 to 3 (preferably 1) substituents selected from
(a) amino, and
(b) $C_{1-6}$ alkoxy (particularly, methoxy),
(ii) a $C_{2-6}$ alkenylene group (particularly, —CH=CH—),
(iii) a $C_{2-6}$ alkynylene group (particularly, —C≡C—), or
(iv) a $C_{3-6}$ cycloalkylene group (particularly, cyclopropylene),
(2) —NHCO—W$^{1b}$—O—
wherein W$^{1b}$ is a $C_{1-6}$ alkylene group (particularly, —CH$_2$—, —(CH$_2$)$_2$—).
(3) —NHCO—W$^{1c}$—O—W$^{2c}$—
wherein W$^{1c}$ is a $C_{1-6}$ alkylene group (particularly, —CH$_2$—, —(CH$_2$)$_2$—)
W$^{2c}$ is a $C_{1-6}$ alkylene group (particularly, —CH$_2$—, —(CH$_2$)$_2$—),
(4) —NHCO—W$^{1d}$—S—
wherein W$^{1d}$ is a $C_{1-6}$ alkylene group (particularly, —CH$_2$—, —(CH$_2$)$_2$—)
(5) —NHCO—W$^{1e}$—NH—
wherein W$^{1e}$ is a $C_{1-6}$ alkylene group (particularly, —CH$_2$—, —(CH$_2$)$_2$—)
(6) —NHCOO—W$^{1g}$—
wherein W$^{1g}$ is a $C_{1-6}$ alkylene group (particularly, —CH$_2$—, —(CH$_2$)$_2$—)
(7) —NHCO—CO—,
(8) —NHCONH—,
(9) —NHCONH—W$^{1j}$—
wherein W$^{1j}$ is
(i) a $C_{1-6}$ alkylene group (particularly, —CH$_2$—, —(CH$_2$)$_2$—), or
(ii) a $C_{3-6}$ cycloalkylene group (particularly, cyclopropylene), or
(10) —NHCONH—W$^{1k}$—O—
wherein W$^{1k}$ is a $C_{1-6}$ alkylene group (particularly, —CH$_2$—, —(CH$_2$)$_2$—); and
$R^5$ is
(1) cyclohexyl,
(2) phenyl optionally having 1 to 3 substituents selected from
(a) a halogen atom (particularly, a fluorine atom, a chlorine atom),
(b) $C_{1-6}$ alkyl (particularly, methyl, tert-butyl) optionally having 1 to 3 halogen atoms (particularly, a fluorine atom), and
(c) $C_{1-6}$ alkoxy (particularly, methoxy) optionally having 1 to 3 halogen atoms (particularly, a fluorine atom),
(3) a 5- or 6-membered monocyclic aromatic heterocyclic group (particularly, thienyl, pyridyl, pyrazolyl) optionally having 1 to 3 substituents selected from (a) alkyl (particularly, methyl, tert-butyl) optionally having 1 to 3 halogen atoms (particularly, a fluorine atom), and
(b) phenyl, or
(4) a 5- or 6-membered monocyclic nonaromatic heterocyclic group (particularly, piperidinyl), or a salt thereof.
Compound (C):
N-{5-[4-fluoro-3-({[2-(trifluoromethyl)phenyl]acetyl}amino)-phenoxy][1,3]thiazolo[5,4-b]pyridin-2-yl}cyclopropanecarboxamide (Example 19),
N-{5-[4-fluoro-3-({[4-(trifluoromethyl)phenyl]acetyl}amino)-phenoxy][1,3]thiazolo[5,4-b]pyridin-2-yl}cyclopropanecarboxamide (Example 21),
N-{5-[4-fluoro-3-({[3-(trifluoromethyl)phenyl]acetyl}amino)-phenoxy][1,3]thiazolo[5,4-b]pyridin-2-yl}cyclopropanecarboxamide (Example 22),
N-{5-[4-fluoro-3-({[3-(trifluoromethyl)phenyl]carbamoyl}-amino)phenoxy][1,3]thiazolo[5,4-b]pyridin-2-yl}cyclopropanecarboxamide (Example 23),
N-{5-[4-fluoro-3-({[6-(trifluoromethyl)pyridin-3-yl]carbamoyl}amino)phenoxy][1,3]thiazolo[5,4-b]pyridin-2-yl}cyclopropanecarboxamide (Example 29),
or a salt thereof.

When compound (I) is a salt, examples of such salt include metal salt, ammonium salt, a salt with organic base, a salt with inorganic acid, a salt with organic acid, a salt with basic or acidic amino acid and the like. Preferable examples of the metal salt include alkali metal salt such as sodium salt, potassium salt and the like; alkaline earth metal salt such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with m formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysine, ornithine and the like, and preferable examples of the salt with acidic amino acid include a salt with aspartic acid, glutamic acid and the like.

Of these, a pharmaceutically acceptable salt is preferable. For example, when a compound has an acidic functional group, an inorganic salt such as alkali metal salt (e.g., sodium salt, potassium salt etc.), alkaline earth metal salt (e.g., calcium salt, magnesium salt etc.) and the like, ammonium salt etc., and when a compound has a basic functional group, for example, a salt with inorganic acid such as hydrochloric acid, hydrobromic acid, nitric acid, sulfuric acid, phosphoric acid and the like, or a salt with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like can be mentioned.

The production methods of compound (I) are described in the following.

In the following reactions, each of the compounds to be used as starting materials may be used as a salt. Examples of such salt include those exemplified as the salts for compound (1).

In the following reactions, the resultant product may be used as a reaction mixture or a crude product for the next reaction. Alternatively, it may be isolated from a reaction mixture by a separation means known per se (e.g., recrystallization, distillation, chromatography), and used for the next reaction.

In the following reactions, unless otherwise specified, alkylation reaction, hydrolysis, amination reaction, amidation reaction, esterification reaction, etherification reaction, oxidation reaction, reduction reaction, acylation reaction, urea formation reaction, aryl coupling reaction and the like are performed according to methods known per se (e.g., the method described in ORGANIC FUNCTIONAL GROUP PREPARATIONS, 2nd edition, ACADEMIC PRESS, INC., 1989; the method described in Comprehensive Organic Transformations, VCH Publishers Inc., 1989) and the like.

In the following reactions, an intramolecular functional group of the obtained compound can also be converted to an object functional group by combining chemical reactions known per se. Examples of such chemical reaction include alkylation reaction, hydrolysis, amination reaction, amidation reaction, esterification reaction, etherification reaction, oxidation reaction, reduction reaction, acylation reaction, urea formation reaction, aryl coupling reaction, deprotection and the like.

In the following reactions, when the starting compound has an amino group, a carboxyl group, a hydroxy group, a carbonyl group or a mercapto group as a substituent, a protecting group generally used in the peptide chemistry and the like may be introduced into these groups, and the object compound can be obtained by removing the protecting group as necessary after the reaction.

Examples of amino-protecting groups include formyl group, $C_{1-6}$ alkyl-carbonyl group, $C_{1-6}$ alkoxy-carbonyl group, benzoyl group, $C_{7-10}$ aralkyl-carbonyl group (e.g., benzylcarbonyl), $C_{7-14}$ aralkyloxy-carbonyl group (e.g., benzyloxycarbonyl, 9-fluorenylmethoxycarbonyl), trityl group, phthaloyl group, N,N-dimethylaminomethylene group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups optionally have 1 to 3 substituents selected from a halogen atom, a $C_{1-6}$ alkoxy group and a nitro group.

Examples of carboxyl-protecting groups include $C_{1-6}$ alkyl group, $C_{7-10}$ aralkyl group (e.g., benzyl), phenyl group, trityl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups optionally have 1 to 3 substituents selected from a halogen atom, a $C_{1-6}$ alkoxy group and a nitro group.

Examples of hydroxy-protecting groups include $C_{1-6}$ alkyl group, phenyl group, trityl group, $C_{7-10}$ aralkyl group (e.g., benzyl), formyl group, $C_{1-6}$ alkyl-carbonyl group, benzoyl group, $C_{7-10}$ aralkyl-carbonyl group (e.g., benzylcarbonyl), 2-tetrahydropyranyl group, 2-tetrahydrofuranyl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like can be mentioned. These groups optionally have 1 to 3 substituents selected from a halogen atom, a $C_{1-6}$ alkyl group, a $C_{1-6}$ alkoxy group and a nitro group.

Examples of carbonyl-protecting groups include cyclic acetal (e.g., 1,3-dioxane), non-cyclic acetal (e.g., di-$C_{1-6}$ alkylacetal) and the like.

Examples of mercapto-protecting groups include $C_{1-6}$ alkyl group, phenyl group, trityl group, $C_{7-10}$ aralkyl group (e.g., benzyl), $C_{1-6}$ alkyl-carbonyl group, benzoyl group, $C_{7-10}$ aralkyl-carbonyl group (e.g., benzylcarbonyl), $C_{1-6}$ alkoxy-carbonyl group, $C_{6-14}$ aryloxy-carbonyl group (e.g., phenyloxycarbonyl), $C_{7-14}$ aralkyloxy-carbonyl group (e.g., benzyloxycarbonyl, 9-fluorenylmethoxycarbonyl), 2-tetrahydropyranyl group, mono $C_{1-6}$ alkylamino-carbonyl group (e.g., methylaminocarbonyl, ethylaminocarbonyl) and the like. These groups optionally have 1 to 3 substituents selected from a halogen atom, a $C_{1-6}$ alkyl group, a $C_{1-6}$ alkoxy group and a nitro group.

The above-mentioned protecting groups can be removed by a deprotection method known per se (e.g., the method described in Protective Groups in Organic Synthesis, John Wiley and Sons (1980)).

The abbreviations used in the following reactions are explained.

Examples of the "halogenated hydrocarbons" as a solvent include dichloromethane, chloroform, carbon tetrachloride, 1,2-dichloroethane and the like.

Examples of the "aromatic hydrocarbons" as a solvent include benzene, toluene, xylene and the like.

Examples of the "alcohols" as a solvent include methanol, ethanol, isopropanol, t-butanol, phenol and the like.

Examples of the "ethers" as a solvent include diethyl ether, tetrahydrofuran, dioxane and the like.

In the following reactions, base means an inorganic base or an organic base. Examples of such base include sodium hydroxide, potassium hydroxide, sodium carbonate, potassium carbonate, sodium hydrogen carbonate, potassium hydrogen carbonate, cesium carbonate, triethylamine, N-ethyldiisopropylamine, pyridine, N,N-dimethylaminopyridine, sodium methoxide, sodium ethoxide, potassium t-butoxide, sodium hydride, sodium amide, diazabicycloundecene (DBU) and the like.

In the following reactions, examples of the ammonium salt include pyridine hydrochloride, pyridine hydrobromide, pyridine p-toluenesulfonate, quinoline hydrochloride, isoquinoline hydrochloride, pyrimidine hydrochloride, pyrazine hydrochloride, triazine hydrochloride, trimethylamine hydrochloride, triethylamine hydrochloride, N-ethyldiisopropylamine hydrochloride and the like.

In the following reactions, examples of the palladium complex include palladium acetate, palladium chloride, tris(dibenzylideneacetone)dipalladium (0) and the like.

In the following reactions, examples of the phosphine ligand include triphenylphosphine, 2,2'-bis(diphenylphosphino)-1,1'-binaphthyl (BINAP), dicyclohexyl(2',4',6'-triisopropylbiphenyl-2-yl)phosphine (X-phos) and the like.

(Production Method 1)

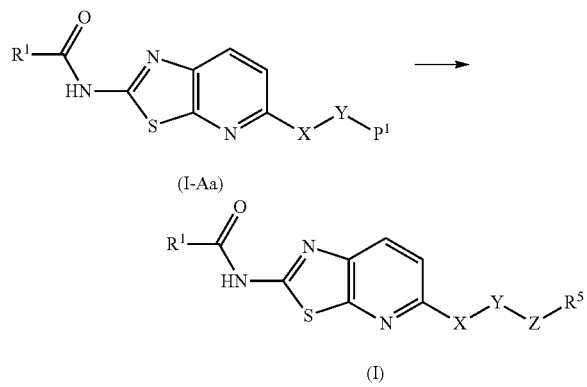

wherein $P^1$ is a functional group convertible to —Z—$R^5$ such as —$NHR^3$ and the like, and other symbols are each as defined above.

Compound (I) wherein Z is a group selected from
(1) —$NR^3$CO—$W^1$—,
(2) —$NR^3$CO—$W^1$—O—,
(3) —$NR^3$CO—$W^1$—O—$W^2$—,
(4) —$NR^3$CO—$W^1$—S—,
(5) —$NR^3$CO—$W^1$—$NR^4$—,
(6) —$NR^3$COO—,
(7) —$NR^3$COO—$W^1$—, and
(8) —$NR^3$CO—CO—, wherein each symbol is as defined above can be produced by subjecting, for example, compound (I-Aa) wherein $P^1$ is —$NHR^3$ to a conversion reaction such as acylation known per se and the like.

The acylation reaction can be performed by reacting compound (I-Aa) with carboxylic acid, ester or reactive derivative (e.g., acid halide, acid anhydride, active ester, acid imidazolide and the like) corresponding to the —Z—$R^5$ moiety of compound (I).

The amount of carboxylic acid, ester or reactive derivative to be used is generally 1-10 equivalents relative to 1 equivalent of compound (I-Aa).

This reaction can be performed in the presence of a base as necessary.

The amount of the base to be used is generally 1-10 equivalents relative to 1 equivalent of compound (I-Aa).

In addition, this reaction may be performed in the presence of a condensing agent as necessary. Examples of such condensing agent include carbodiimide condensation reagent (e.g., dicyclohexylcarbodiimide, diisopropylcarbodiimide, 1-ethyl-3-dimethylaminopropylcarbodiimide and hydrochloride thereof), phosphoric acid condensation reagent (e.g., diethyl cyanophosphate, diphenylphosphorylazide), N,N'-carbonyldiimidazole, 2-chloro-1,3-dimethylimidazolium tetrafluoroborate, O-(7-azabenzotriazol-1-yl)-N,N,N',N'-tetramethyluronium hexafluorophosphate and the like.

The amount of the condensing agent to be used is generally 0.1-10 equivalents relative to 1 equivalent of compound (I-Aa).

For this reaction, a condensation promoter (e.g., 1-hydroxy-7-azabenzotriazole, 1-hydroxybenzotriazole, N-hydroxysuccinimide, N-hydroxyphthalimide) may be used as necessary.

The amount of the condensation promoter to be used is generally 0.1-10 equivalents relative to 1 equivalent of compound (I-Aa).

In addition, this reaction can be performed in a solvent as necessary. Examples of such solvent include halogenated hydrocarbons, aromatic hydrocarbons, ethers, acetonitrile, ethyl acetate, N,N-dimethylformamide, N,N-dimethylacetamide, 1-methyl-2-pyrrolidone, pyridine, dimethyl sulfoxide, hexamethylphosphoramide and the like.

The reaction temperature is generally-30-120° C., preferably 0-100° C.

The reaction time is generally 0.1-30 hr.

Compound (I-Aa) to be used as a starting material can be produced by the below-mentioned method.

The carboxylic acid, ester or reactive derivative corresponding to the —Z—$R^5$ moiety of compound (I) may be commercially available, or can be produced by a method known is per se.

Compound (I) wherein Z is a group selected from
(1) —$NR^3$CONR$^4$—,
(2) —$NR^3$CONR$^4$—$W^1$—, and
(3) —$NR^3$CONR$^4$—$W^1$—O— wherein each symbol is as defined above can be produced by subjecting, for example, compound (I-Aa) wherein $P^1$ is —NHR³ to a conversion reaction such as urea formation reaction known per se and the like.

This reaction can be performed by reacting compound (I-Aa) with a reactive derivative corresponding to the —Z—R⁵ moiety of compound (I), such as isocyanate, carbamoylchloride, trichloroethyl carbamate and the like.

The amount of the reactive derivative to be used is generally 1-10 equivalents relative to 1 equivalent of compound (I-Aa).

This reaction may be performed in the presence of a base as necessary.

The amount of the base to be used is generally 1-10 equivalents relative to 1 equivalent of compound (I-Aa).

In addition, this reaction can be performed in a solvent as necessary. Examples of such solvent include those exemplified for the aforementioned acylation reaction.

The reaction temperature is generally −30-100° C.

The reaction time is generally 0.1-30 hr.

The reactive derivative corresponding to the —Z—R⁵ moiety of compound (I) to be used as a starting material may be commercially available, or can be produced by a method known per se.

In addition, compound (I) can be produced, for example, by converting compound (I-Aa) wherein P¹ is —NHR³ to a reactive intermediate such as carbamoylchloride, carbamoylimidazolide and the like using a carbonylating agent such as triphosgene, carbodiimidazole and the like, and reacting the reactive intermediate with amine corresponding to the —Z—R⁵ moiety of compound (I).

The amount of the carbonylating agent to be used is generally 1-5 equivalents relative to 1 equivalent of compound (I-Aa).

The amount of the amine to be used is generally 1-10 equivalents relative to 1 equivalent of compound (I-Aa).

This reaction may be performed in the presence of a base as necessary.

The amount of the base to be used is generally 1-10 equivalents relative to 1 equivalent of compound (I-Aa).

In addition, this reaction can be performed in a solvent as necessary. Examples of such solvent include those exemplified for the aforementioned acylation reaction.

The reaction temperature is generally −30-100° C.

The reaction time is generally 0.1-30 hr.

The amine corresponding to the —Z—R⁵ moiety of compound (I) to be used as a starting material may be commercially available, or can be produced by a method known per se.

Compound (I) and compound (I-Aa) can be produced according to Production method A, B or C used for producing the following compound (I-A).

(Production Method A)

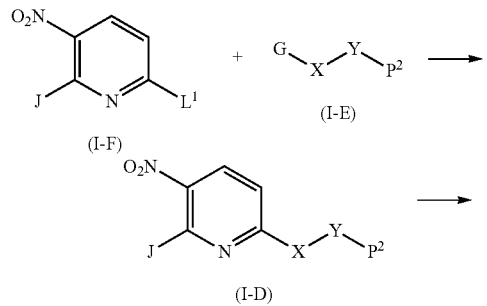

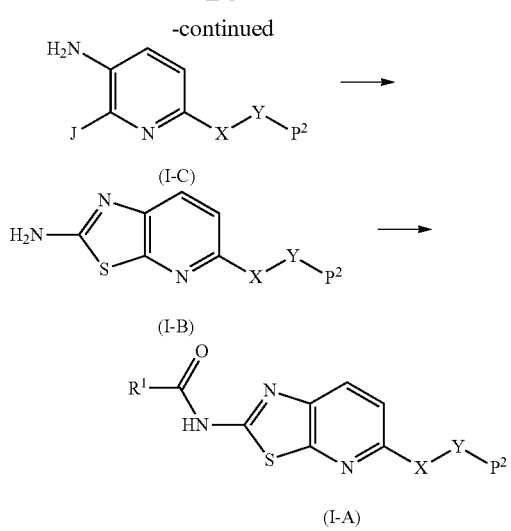

wherein L¹ is a leaving group; G is a hydrogen atom or a metal atom (e.g., alkali metals such as lithium, sodium, potassium, cesium and the like; alkaline earth metals such as magnesium, calcium and the like); P² is —Z—R⁵ or —P¹; J is a hydrogen atom, —SR⁶ or —SCN; R⁶ is a hydrogen atom or a mercapto-protecting group (e.g., methyl, phenyl, benzyl, t-butyl) and other symbols are each as defined above.

Examples of the leaving group for L¹ include
(1) a halogen atom (e.g., fluorine, chlorine, bromine, iodine);
(2) a group represented by the formula: —S(O)$_k$R⁷ wherein k is an integer of 0, 1 or 2; R⁷ is a C$_{1-4}$ alkyl group (e.g., methyl, ethyl, propyl, tert-butyl), a C$_{6-10}$ aryl group (e.g., benzyl, phenyl, tolyl); or
(3) a group represented by the formula: —OR⁷ wherein R⁷ is as defined above, and the like.

Compound (I-A) can be produced by subjecting compound (I-B) to a functional group conversion reaction known per se.

For example, compound (I-B) is subjected to an acylation reaction known per se using carboxylic acid represented by the formula: R¹—COOH or a reactive derivative thereof (e.g., acid halide, acid anhydride, active ester, acid imidazolide and the like), and the resulting compound is subjected to a functional group conversion reaction known per se as necessary, whereby compound (I-A) can be produced.

The acylation reaction can be performed in the same manner as in the aforementioned Production method 1.

The carboxylic acid represented by R¹—COOH and a reactive derivative thereof can be produced by a method known per se.

Compound (I-B) can be produced from compound (I-C).

For example, compound (I-C) wherein J is —SR⁶ is subjected to deprotection known per se to convert J to —SH, and reacted with cyanogen bromide or 1,1-di-1H-imidazol-1-yl methanimine, whereby compound (I-B) can be produced.

The amount of the cyanogen bromide or 1,1-di-1H-imidazol-1-ylmethanimine to be used is generally, 1-10 equivalents, preferably 1-5 equivalents, relative to 1 equivalent of compound (I-C).

This reaction is preferably performed in a solvent. Examples of such solvent include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

In addition, this reaction may also be performed in the presence of a base.

The amount of the base to be used is generally 0.1-10 equivalents, preferably 0.1-2 equivalents, relative to 1 equivalent of compound (I-C).

This reaction can be carried out under cooling (generally about −78 to 20° C., preferably about −10 to 10° C.), at room temperature or under heating (generally about 40 to 200° C., preferably about 40 to 160° C.)

The reaction time is generally about 1 to 30 hr, preferably about 1 to 20 hr, further preferably about 1 to 10 hr.

In addition, compound (I-B) can also be produced by reacting compound (I-C) wherein J is —SCN with an acid in a solvent.

Examples of the acid include hydrochloric acid, acetic acid, sulfuric acid and the like.

The amount of the acid to be used is 1-10 equivalents or a solvent amount in some cases, preferably 1-5 equivalents, relative to 1 equivalent of compound (I-C).

As the solvent, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

This reaction can be carried out under cooling (generally about −78 to 20° C., preferably about −10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

In addition, compound (I-B) can also be produced by reacting compound (I-C) wherein J is a hydrogen atom with potassium thiocyanate, sodium thiocyanate or ammonium thiocyanate, and bromine.

The amount of potassium thiocyanate, sodium thiocyanate or ammonium thiocyanate to be used in this reaction is generally, 1-10 equivalents, preferably 1-5 equivalents, relative to 1 equivalent of compound (I-C).

The amount of bromine to be used is generally 1-5 equivalents, preferably 1-2 equivalents, relative to 1 equivalent of compound (I-C).

This reaction is preferably performed in a solvent. As such solvent, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

This reaction can be carried out under cooling (generally about −78 to 20° C., preferably about −10 to 10° C.), at room temperature or under heating (generally about 40 to 200° C., preferably about 40 to 160° C.)

The reaction time is generally about 1 to 30 hr, preferably about 1 to 20 hr, further preferably about 1 to 10 hr.

Alternatively, compound (I-B) can also be produced by subjecting compound (I-D) to a reduction reaction known per se.

For example, compound (I-B) can be directly produced by subjecting compound (I-D) wherein J is —SCN to a reduction reaction, without via compound (I-C) wherein J is —SCN.

Moreover, compound (I-B) can also be produced by reacting compound (I-D) wherein J is —SCN with reduced iron in the presence of an acid.

Examples of the acid include hydrochloric acid, acetic acid, sulfuric acid and the like.

The amount of the acid to be used is 1-20 equivalents or a solvent amount in some cases, preferably 1-10 equivalents, relative to 1 equivalent of compound (I-D).

The amount of the reduced iron to be used in this reaction is 1-10 equivalents, preferably 1-5 equivalents, relative to 1 equivalent of compound (I-D).

This reaction is preferably performed in a solvent. As such solvent, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

This reaction can be carried out under cooling (generally about −78 to 20° C., preferably about −10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

Compound (I-D) can be produced by reacting compound (I-E) with compound (I-F).

In compound (I-E), G is mainly a hydrogen atom but may be a metal atom.

The amount of compound (I-E) to be used is generally, 1-5 equivalents, preferably 1-2 equivalents, relative to 1 equivalent of compound (I-F).

This reaction is preferably performed in a solvent. Examples of such solvent include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

In addition, a base or an ammonium salt may be used for this reaction.

The amount of the base or ammonium salt to be used is generally 1-10 equivalents, preferably 1-2 equivalents, relative to 1 equivalent of compound (I-F).

In addition, a palladium complex or a phosphine ligand may be used as a catalyst for this reaction.

The amount of the palladium complex to be used is generally 0.05-10 equivalents, preferably 0.05-2 equivalents, relative to 1 equivalent of compound (I-F).

The amount of the phosphine ligand to be used is generally 0.1-20 equivalents, preferably 0.1-4 equivalents, relative to 1 equivalent of compound (I-F).

This reaction can be carried out under cooling (generally about −78 to 20° C., preferably about −10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

In addition, this reaction may be performed under microwave irradiation.

Compound (I-E) to be used as a starting material for this reaction may be commercially available, or can be produced by means known per se.

In addition, compound (I-F) may be commercially available, or can be produced by means known per se.

(Production Method B)

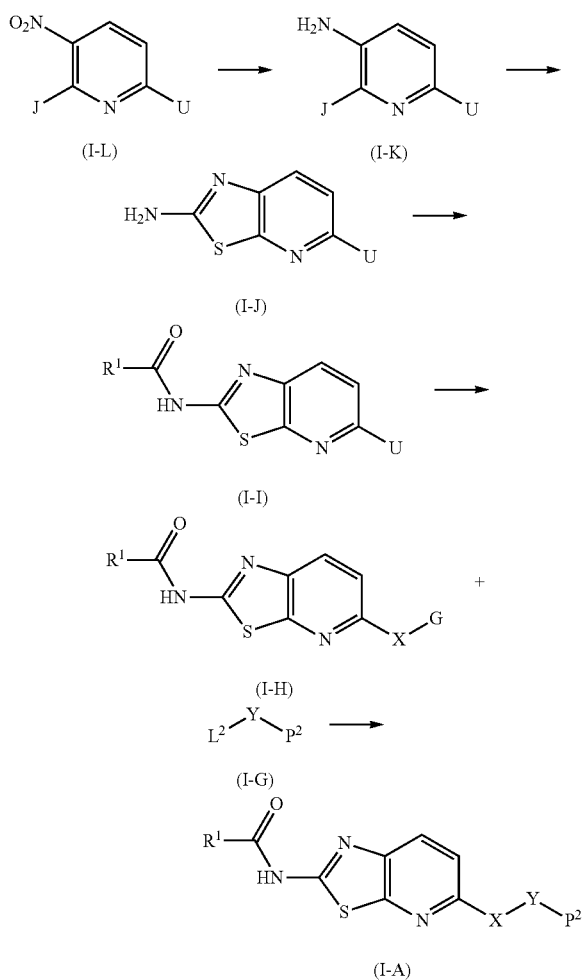

wherein $L^2$ is a leaving group; U is —X-G or a functional group convertible to —X-G (e.g., —NO$_2$, —OR$^8$ (R$^8$ is a C$_{1-4}$ alkyl group (e.g., methyl, ethyl, propyl, tert-butyl), or a C$_{6-10}$ aryl group (e.g., benzyl, phenyl, tolyl)); and other symbols are each as defined above.

Compound (I-A) can be produced by reacting compound (I-H) with compound (I-G).

In compound (I-G), as the leaving group for $L^2$, those similar to the aforementioned leaving group for $L^1$ can be used.

In compound (I-H), G is mainly a hydrogen atom, and a metal atom can also be used.

The amount of compound (I-H) to be used is 1-5 equivalents, preferably 1-2 equivalents, relative to 1 equivalent of compound (I-G).

This reaction is preferably performed in a solvent. Examples of such solvent include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

In addition, a base or an ammonium salt may be used for this reaction.

The amount of the base or ammonium salt to be used is generally 1-10 equivalents, preferably 1-2 equivalents, relative to 1 equivalent of compound (I-G).

In addition, a palladium complex or a phosphine ligand may be used as a catalyst for this reaction.

The amount of the palladium complex to be used is generally 0.05-10 equivalents, preferably 0.05-2 equivalents, relative to 1 equivalent of compound (I-G).

The amount of the phosphine ligand to be used is generally 0.1-20 equivalents, preferably 0.1-4 equivalents, relative to 1 equivalent of compound (I-G).

This reaction can be carried out under cooling (generally about −78 to 20° C., preferably about −10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

In addition, this reaction may be performed under microwave irradiation.

Compound (I-G) to be used as a starting material for this reaction may be commercially available, or can be produced by means known per se.

Compound (I-H) can be produced by subjecting U of compound (I-I) to a functional group conversion reaction known per se.

For example, compound (I-H) wherein —X-G is —NH$_2$ can be produced from compound (I-I) wherein U is —NO$_2$ by a reduction reaction known per se. Furthermore, by subjecting this compound to a reductive amination reaction known per se, a coupling reaction known per se using a palladium catalyst and the like, a methyl group or an amino-protecting group (e.g., benzyl, t-butyl) can be introduced into the —NH$_2$ moiety represented by —X-G.

Alternatively, compound (I-I) wherein U is —OR$^8$ is subjected to deprotection known per se to give compound (I-H) wherein —X-G is —OH.

Compound (I-I) to be used as a starting material can be produced by a means known per se.

For example, compound (I-I) can be produced by subjecting compound (I-J) and carboxylic acid represented by the formula: R$^1$—COOH or a reactive derivative thereof to an acylation reaction known per se by similar steps as in the aforementioned production method A.

Compound (I-J) to be used as a starting material can be produced by a method known per se.

For example, compound (I-J) can be produced from compound (I-K).

For example, compound (I-K) wherein J is —SR$^6$ (R$^6$ is as defined above) is subjected to deprotection known per se to convert J to —SH, and reacted with cyanogen bromide or 1,1-di-1H-imidazol-1-ylmethanimine to give compound (I-J).

The amount of the cyanogen bromide or 1,1-di-1H-imidazol-1-ylmethanimine to be used is generally, 1-10 equivalents, preferably 1-5 equivalents, relative to 1 equivalent of to compound (I-K).

This reaction is preferably performed in a solvent. Examples of such solvent include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

In addition, this reaction may also be performed in the presence of a base.

The amount of the base to be used is generally 0.1-10 equivalents, preferably 0.1-2 equivalents, relative to 1 equivalent of compound (I-K).

This reaction can be carried out under cooling (generally about −78 to 20° C., preferably about −10 to 10° C.), at room temperature or under heating (generally about 40 to 200° C., preferably about 40 to 160° C.)

The reaction time is generally about 1 to 30 hr, preferably about 1 to 20 hr, further preferably about 1 to 10 hr.

In addition, compound (I-J) can also be produced by reacting compound (I-K) wherein J is —SCN with an acid in a solvent.

Examples of the acid include hydrochloric acid, acetic acid, sulfuric acid and the like.

The amount of the acid to be used is 1-10 equivalents or a solvent amount in some cases, preferably 1-5 equivalents, relative to 1 equivalent of compound (I-K).

As the solvent, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

This reaction can be carried out under cooling (generally about –78 to 20° C., preferably about –10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

In addition, compound (I-J) can also be produced by reacting compound (I-K) wherein J is a hydrogen atom with potassium thiocyanate, sodium thiocyanate or ammonium thiocyanate, and bromine.

The amount of the potassium thiocyanate, sodium thiocyanate or ammonium thiocyanate to be used in this reaction is generally 1-10 equivalents, preferably 1-5 equivalents, relative to 1 equivalent of compound (I-K).

The amount of the bromine to be used is generally 1-5 equivalents, preferably 1-2 equivalents, relative to 1 equivalent of compound (I-K).

This reaction is preferably performed in a solvent. As such solvent, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

This reaction can be carried out under cooling (generally about –78 to 20° C., preferably about –10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

Compound (I-K) to be used as a starting material may be commercially available, or can be produced by means known per se.

For example, compound (I-K) can be produced by subjecting compound (I-L) to a reduction reaction known per se to convert the nitro group to an amino group.

Alternatively, compound (I-J) can be directly produced by subjecting compound (I-L) wherein J is —SCN to a reduction reaction, without via compound (I-K) wherein J is —SCN.

In addition, compound (I-J) can also be produced by reacting compound (I-L) wherein J is —SCN with reduced iron in the presence of an acid.

Examples of the acid include hydrochloric acid, acetic acid, sulfuric acid and the like.

The amount of the acid to be used is 1-20 equivalents, or a solvent amount in some cases, preferably 1-10 equivalents, relative to 1 equivalent of compound (I-L).

The amount of the reduced iron to be used in this reaction is 1-10 equivalents, preferably 1-5 equivalents, relative to 1 equivalent of compound (I-L).

This reaction is preferably performed in a solvent. As such solvent, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

This reaction can be carried out under cooling (generally about –78 to 20° C., preferably about –10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

Compound (I-L) to be used as a starting material may be commercially available, or can be produced by means known per se.

(Production Method C)

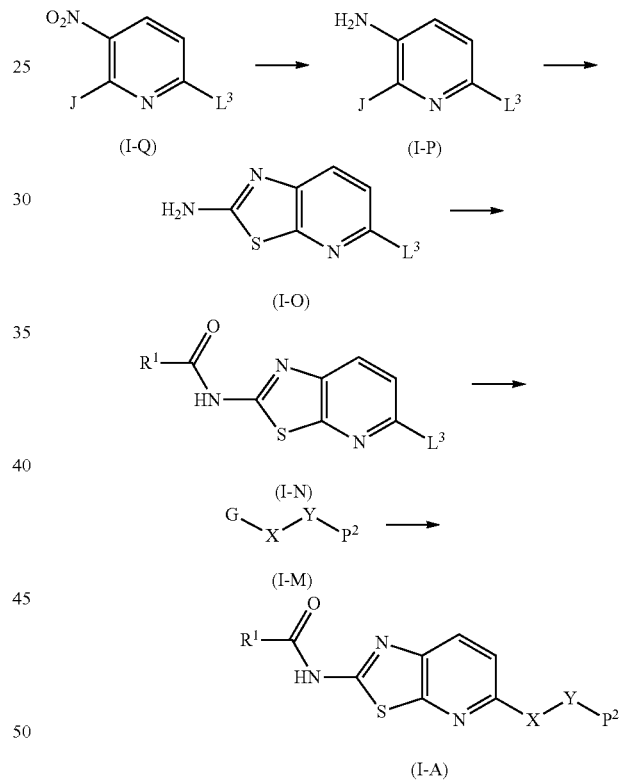

wherein $L^3$ is a leaving group; and other symbols are each as defined above.

Compound (I-A) can be produced by reacting compound (I-M) with compound (I-N).

In compound (I-M), G is mainly a hydrogen atom but may be a metal atom.

In compound (I-N), as the leaving group for $L^3$, those similar to the aforementioned leaving group for $L^1$ can be used.

The amount of compound (I-M) to be used is generally, 1-5 equivalents, preferably 1-2 equivalents, relative to 1 equivalent of compound (I-N).

This reaction is preferably performed in a solvent. Examples of such solvent include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

In addition, a base or an ammonium salt may be used for this reaction.

The amount of the base or ammonium salt to be used is generally 1-10 equivalents, preferably 1-2 equivalents, relative to 1 equivalent of compound (I-N).

In addition, a palladium complex or a phosphine ligand may be used as a catalyst for this reaction.

The amount of the palladium complex to be used is generally 0.05-10 equivalents, preferably 0.05-2 equivalents, relative to 1 equivalent of compound (I-N).

The amount of the phosphine ligand to be used is generally 0.1-20 equivalents, preferably 0.1-4 equivalents, relative to 1 equivalent of compound (I-N).

This reaction can be carried out under cooling (generally about −78 to 20° C., preferably about −10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

In addition, this reaction may be performed under microwave irradiation.

Compound (I-M) to be used as a starting material for this reaction may be commercially available, or can be produced by means known per se.

In addition, compound (I-N) can be produced by a method known per se.

For example, the starting compound (I-N) can be produced by subjecting compound (I-O) and carboxylic acid represented by the formula: $R^1$—COOH or a reactive derivative thereof to an acylation reaction known per se in the same manner as in the aforementioned production method A.

Compound (I-O) to be used as a starting material can be produced by a method known per se.

For example, compound (I-O) can be produced from compound (I-P).

For example, compound (I-O) can be produced by subjecting compound (I-P) wherein J is —$SR^6$ ($R^6$ is as defined above) to deprotection known per se to convert J to —SH and then reacting the compound with cyanogen bromide or 1,1-di-1H-imidazol-1-ylmethanimine.

The amount of the cyanogen bromide or 1,1-di-1H-imidazol-1-ylmethanimine to be used is generally, 1-10 equivalents, preferably 1-5 equivalents, relative to 1 equivalent of compound (I-P).

This reaction is preferably performed in a solvent. Examples of such solvent include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

In addition, this reaction may also be performed in the presence of a base.

The amount of the base to be used is generally 0.1-10 equivalents, preferably 0.1-2 equivalents, relative to 1 equivalent of compound (I-P).

This reaction can be carried out under cooling (generally about −78 to 20° C., preferably about −10 to 10° C.), at room temperature or under heating (generally about 40 to 200° C., preferably about 40 to 160° C.)

The reaction time is generally about 1 to 30 hr, preferably about 1 to 20 hr, further preferably about 1 to 10 hr.

In addition, compound (I-O) can be produced by reacting compound (I-P) wherein J is —SCN with an acid in a solvent.

Examples of the acid include hydrochloric acid, acetic acid, sulfuric acid and the like.

The amount of the acid to be used is 1-10 equivalents or a solvent amount in some cases, preferably 1-5 equivalents, relative to 1 equivalent of compound (I-P).

As the solvent, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

This reaction can be carried out under cooling (generally about −78 to 20° C., preferably about −10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

In addition, compound (I-O) can be produced by reacting compound (I-P) wherein J is a hydrogen atom with potassium thiocyanate, sodium thiocyanate or ammonium thiocyanate, and bromine.

The amount of the potassium thiocyanate, sodium thiocyanate or ammonium thiocyanate to be used in this reaction is generally, 1-10 equivalents, preferably 1-5 equivalents, relative to 1 equivalent of compound (I-P).

The amount of the bromine to be used is 1-5 equivalents, preferably 1-2 equivalents, relative to 1 equivalent of compound (I-P).

This reaction is preferably performed in a solvent. As such solvent, for example, halogenated hydrocarbons, aromatic hydrocarbons, alcohols, ethers, acetone, acetonitrile, ethyl acetate, N,N-dimethylformamide, N,N-dimethylacetamide, methyl-2-pyrrolidone, dimethyl sulfoxide, hexamethylphosphoramide, water, acetic acid or a mixed solvent thereof and the like can be used.

This reaction can be carried out under cooling (generally about −78 to 20° C., preferably about −10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

Compound (I-P) to be used as a starting material may be commercially available, or can be produced by means known per se.

For example, compound (I-P) can be produced by subjecting compound (I-Q) to a reduction reaction known per se to convert a nitro group to an amino group.

Alternatively, compound (I-O) can also be directly produced by subjecting compound (I-Q) wherein J is —SCN to a reduction reaction, without via compound (I-P) wherein J is —SCN.

In addition, compound (I-O) can also be produced by reacting compound (I-Q) wherein J is —SCN with reduced iron in the presence of an acid.

Examples of the acid include hydrochloric acid, acetic acid, sulfuric acid and the like.

The amount of the acid to be used is 1-20 equivalents, or a solvent amount in some cases, preferably 1-10 equivalents, relative to 1 equivalent of compound (I-Q).

The amount of the reduced iron to be used in this reaction is 1-10 equivalents, preferably 1-5 equivalents, relative to 1 equivalent of compound (I-Q).

This reaction is preferably performed in a solvent. As such solvent, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

This reaction can be carried out under cooling (generally about −78 to 20° C., preferably about −10 to 10° C.), at room temperature or under heating (generally about 40 to 200° C., preferably about 40 to 160° C.).

The reaction time is generally about 1 to 30 hr, preferably about 1 to 20 hr, further preferably about 1 to 10 hr.

Compound (I-Q) to be used as a starting material may be commercially available, or can be produced by means known per se.

Compound (I) can be isolated and purified by means known per se, such as phase transfer, concentration, solvent extraction, fractionation, liquid conversion, crystallization, recrystallization, chromatography and the like. When compound (I) is obtained as a free compound, it can be converted to a desired salt by a method known per se or a method analogous thereto. Conversely, when the compound is obtained as a salt, it can be converted to a free form or other desired salt by a method known per se or a method analogous thereto.

Compound (I) may be used as a prodrug. A prodrug of compound (I) means a compound converted to compound (I) by a reaction due to an enzyme, a gastric acid, etc. under the physiological condition in the living body, that is, a compound converted to compound (I) by oxidation, reduction, hydrolysis, etc. due to an enzyme, a compound converted to compound (I) by hydrolysis etc. due to gastric acid, and the like.

A prodrug of compound (I) may be
(1) a compound obtained by subjecting an amino in compound (I) to an acylation, alkylation or phosphorylation (e.g., a compound obtained by subjecting an amino in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, ethoxycarbonylation, tert-butoxycarbonylation, acetylation or cyclopropylcarbonylation);
(2) a compound obtained by subjecting hydroxy in compound (I) to acylation, alkylation, phosphorylation or boration (e.g., a compound obtained by subjecting hydroxy in compound (I) to acetylation, palmitoylation, propanoylation, pivaloylation, succinylation, fumarylation, alanylation or dimethylaminomethylcarbonylation);
(3) a compound obtained by subjecting carboxy in compound (I) to esterification or amidation (e.g., a compound obtained by subjecting carboxy in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any one of these compounds can be produced from compound (I) by a method known per se.

A prodrug of compound (I) may also be a compound converted into compound (I) under physiological conditions, such as those described in IYAKUHIN no KAIHATSU (Development of Pharmaceuticals), Vol. 7, Design of Molecules, p. 163-198, Published by HIROKAWA SHOTEN (1990).

When compound (I) has an isomer such as optical isomer, stereoisomer, positional isomer, rotational isomer and the like, any isomer and a mixture thereof are encompassed in compound (I). For example, when compound (I) has an optical isomer, an optical isomer separated from a racemate is also encompassed in compound (I). Such isomers can be obtained as independent products by a synthesis means or a separation means (concentration, solvent extraction, column chromatography, recrystallization and the like) known per se.

Compound (I) may be a crystal, and both a single crystal and crystal mixtures are encompassed in compound (I). Crystals can be produced by crystallization according to crystallization methods known per se.

Compound (I) may be a solvate (e.g., a hydrate etc.) or a non-solvate (e.g., a non-hydrate etc.), any of which is encompassed in compound (I).

A compound labeled with an isotope (e.g., $^3$H, $^{14}$C, $^{35}$S, $^{125}$I etc.) is also encompassed in compound (I).

Furthermore, a deuterium conversion form wherein $^1$H is converted to $^2$H(D) is also encompassed in compound (I).

Compound (I) or a prodrug thereof (in the specification, sometimes to be abbreviated as "the compound of the present invention") has an Raf (particularly B-Raf) inhibitory activity, and can provide a clinically useful drug for the prophylaxis or treatment of cancer, and a cancer growth inhibitor, a cancer metastasis suppressive agent. In addition, the compound of the present invention can be used for the prophylaxis or treatment of B-Raf dependent diseases in mammals.

The compound of the present invention also has an inhibitory activity on a vascular endothelial growth factor receptor (VEGFR; particularly, VEGFR2).

The compound of the present invention shows a strong inhibitory activity on Raf (particularly, B-Raf). Since the compound of the present invention is also superior in the efficacy, pharmacokinetics (absorption, distribution, metabolism, excretion etc.), solubility (water-solubility etc.), interaction with other pharmaceutical products, safety (acute toxicity, chronic toxicity, genetic toxicity, reproductive toxicity, cardiotoxicity, carcinogenicity etc.), stability (chemical stability, stability to enzyme etc.) and the like, it is useful as a medicament.

Accordingly, the compound of the present invention is useful as an Raf (specifically B-Raf) inhibitor for mammals (e.g., mouse, rat, hamster, rabbit, cat, dog, bovine, sheep, monkey, human, etc.).

The compound of the present invention is used as a medicament such as a drug for the prophylaxis or treatment of Raf-related diseases (proliferative disease, immune disease, inflammatory disease, for example, cancer [e.g., colorectal cancer (e.g., familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer), gastric cancer (e.g., papillary adenocarcinoma, mucinous adenocarcinoma, adenosquamous cancer), breast cancer (e.g., invasive ductal carcinoma, ductal cancer in situ, inflammatory breast cancer), ovarian cancer (e.g., ovarian epithelial cancer, extragonadal germ cell tumor, ovarian germ cell tumor, ovarian low malignant potential tumor), prostate cancer (e.g., hormone-dependent prostate cancer, non-hormone dependent prostate cancer), liver cancer (e.g., primary liver cancer, extrahepatic bile duct cancer), thyroid cancer (e.g., medullary thyroid cancer), kidney cancer (e.g., renal cell carcinoma, renal pelvis and ureter transitional cell cancer), uterine cancer, brain tumor (e.g., pineal astrocytoma, pilocytic astrocytoma, diffuse astrocytoma, anaplastic astrocytoma), melanoma, sarcoma, urinary bladder cancer, hematologic cancer including multiple myeloma]), angiogenesis, diabetic retinopathy, rheumatoid arthritis, psoriasis, atherosclerosis, restenosis, cardiac failure, Kaposi's sarcoma, COPD, cystic fibrosis, pain, asthma, endometriosis, cystic kidney, nephritis, hepatitis, dermatitis, inflammation such as osteoarthritis and the like, hypertension and the like; a cancer growth inhibitor; a cancer metastasis suppressor; an apoptosis promoter and the like.

Among these, it is effective, for example, for colorectal cancer, lung cancer, pancreatic cancer, gastric cancer, breast cancer, ovarian cancer, prostate cancer, liver cancer, thyroid cancer, kidney cancer, brain tumor, melanoma, urinary bladder cancer and hematologic cancer. Particularly, the compound of the present invention is effective for melanoma, thyroid cancer, lung cancer, colorectal cancer (specifically colon cancer), ovarian cancer, prostate cancer or kidney cancer.

The compound of the present invention can be administered orally or parenterally as it is or in a mixture with a pharmacologically acceptable carrier as medicament.

The dosage form of the compound of the present invention for oral administration is, for example, oral preparations such as tablet (including sugar-coated tablet, film-coated tablet, sublingual tablet, buccal tablet, mouth cavity quick-integrating tablet), pill, granule, powder, capsule (including soft capsule, microcapsule), syrup, emulsion, suspension, films (e.g., mouth cavity mucosaadhesion film) and the like. In addition, the dosage form for parenteral administration is, for example, injection, injecting agent, instillation, suppository and the like. In addition, it is effective to make a sustained release preparation by combining the compound with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester etc.).

As a method for producing the compound of the present invention in the above-mentioned dosage form, a known production method (e.g., the method described in the Japanese Pharmacopoeia) generally used in the pertinent field can be employed. When the above-mentioned dosage form is produced, suitable amounts of additives such as excipient, binder, disintegrant, lubricant, sweetening agent, surfactant, suspending agent, emulsifier and the like, generally used in the pharmaceutical field, are appropriately added as necessary for production.

When the compound of the present invention is prepared into a tablet, for example, it can be produced by adding an excipient, a binder, a disintegrant, a lubricant and the like, and when a pill or a granule is to be prepared, it can be produced by adding an excipient, a binder, a disintegrant and the like. When a powder or a capsule is to be prepared, it can be produced by adding an excipient and the like, when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, microcrystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound of the present invention is produced in the above-mentioned dosage form, a suitable amount of a colorant, a preservative, an aromatic, a corrigent, a stabilizer, a thickening agent and the like typically used in the field of preparation can be added on demand.

As the injection, intravenous injection as well as subcutaneous injection, intracutaneous injection, intramuscular injection, instillation and the like are mentioned, and as the sustained release preparation, an iontophoresis transdermal agent and the like are mentioned.

Such injections are prepared by methods known per se, or by dissolving, suspending or emulsifying the compound of the present invention in a sterilized aqueous or oily liquid. As an aqueous liquid for injection, physiological saline, isotonic solutions containing glucose or other auxiliary drugs (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like can be mentioned, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like can be blended. A prepared injection is generally filled in an ampoule.

While the content of the compound of the present invention in the medicament of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the medicament of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 1 to 1000 mg, preferably about 3 to 300 mg, more preferably about 10 to 200 mg, as an active ingredient (the compound of the present invention), which can be given in a single administration or administered in 2 or 3 portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the foam of an injection, relative to 1 kg body weight, which is preferably given by intravenous injection.

The compound of the present invention can be used concurrently with other drugs. To be specific, the compound of the present invention can be used together with medicaments such as hormonal therapeutic agents, chemotherapeutic agents, immunotherapeutic agents, medicaments inhibiting the action of cell growth factors or cell growth factor receptors and the like. In the following, the drugs that can be used in combination with the compound of the present invention are abbreviated as "concomitant drugs".

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testrolactone, aminoglutethimide, LH-RH agonists (e.g., goserelin acetate, buserelin, leuprorelin), droloxifene, epitiostanol, ethinylestradiol sulfonate, aromatase inhibitors (e.g., fadrozole hydrochloride, anastrozole, retrozole, exemestane, vorozole, formestane), anti-androgens (e.g., flutamide, bicartamide, nilutamide), 5α-reductase inhibitors (e.g., finasteride, epristeride), aderenal cortex hormone drugs (e.g., dexamethasone, prednisolone, betamethasone, triamcinolone), androgen synthesis inhibitors (e.g., abiraterone), retinoid and drugs that retard retinoid metabolism (e.g., liarozole), and the like.

Examples of the "chemotherapeutic agents" include alkylating agents, antimetabolites, anticancer antibiotics, plant-derived anticancer agents, and the like.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, DDS preparations thereof, and the like.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine), aminopterine, nelzarabine, leucovorin calcium, tabloid, butocine, calcium folinate, levofolinate calcium, cladribine, emitefur, fludarabine, gemcitabine, hydroxycarbamide, pentostatin, piritrexim, idoxuridine, mitoguazone, thiazophrine, ambamustine, bendamustine, DDS preparations thereof, and the like.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, DDS preparations thereof, and the like.

Examples of the "plant-derived anticancer agents" include etoposide, etoposide phosphate, vinblastine sulfate, vincristine sulfate, vindesine sulfate, teniposide, paclitaxel, docetaxel, vinorelbine, DDS preparations thereof, and the like.

Examples of the "immunotherapeutic agents (Biological Response Modifier; BRM) include picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibody, and the like.

Example of the "cell growth factors" of the "medicaments inhibiting the action of cell growth factors or cell growth factor receptors" include any substances that promote cell proliferation, which are normally peptides having not more than 20,000 molecular weight that are capable of exhibiting their activity at low concentrations by binding to a receptor, including (1) EGF (epidermal growth factor) or substances possessing substantially the same activity as EGF [e.g., TGFα],
(2) insulin or substances possessing substantially the same activity as insulin [e.g., insulin, IGF (insulin-like growth factor)-1, IGF-2],
(3) FGF (fibroblast growth factor) or substances possessing substantially the same activity as FGF [e.g., acidic FGF, basic FGF, KGF (keratinocyte growth factor), FGF-10], and
(4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β, HGF (hepatocyte growth factor), VEGF (vascular endothelial growth factor), heregulin, angiopoietin, and the like].

Examples of the "cell growth factor receptors" include any receptors capable of binding to the aforementioned cell growth factors, including EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor, and the like.

As the "medicaments inhibiting the action of cell growth factors or cell growth factor receptors", EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, Aurora inhibitor, PLK inhibitor, MEK(MEK1/2) inhibitor, MET inhibitor, CDK inhibitor, Akt inhibitor, ERK inhibitor and the like are used. More specifically as such agents, anti-VEGF antibody (e.g., Bevacizumab), anti-HER2 antibody (e.g., Trastuzumab, Pertuzumab), anti-EGFR antibody (e.g., Cetuximab, Panitumumab, Matuzumab, Nimotuzumab), anti-VEGFR antibody, Imatinib, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl) propoxy] quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-

6-(3-methyl-1H-pyrazol-5-ylamino)pyrimidin-2-ylsulfanyl]phenyl]cyclopropanecarboxamide (VX-680), phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2(R), 3-dihydroxypropoxy]-3,4-difluoro-2-(2-fluoro-4-iodophenylamino)benzamide (PD-0325901) and the like are used.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan), topoisomerase II inhibitors (e.g., sobuzoxane), differentiation inducers (e.g., retinoid, vitamin D), other angiogenesis inhibitors (e.g., humagillin, shark extract, COX-2 inhibitor), α-blockers (e.g., tamsulosin hydrochloride), bisphosphonic acids (e.g., pamidronate, zoledronate), thalidomide, 5-azacytidine, decitabine, bortezomib, antitumor antibody (e.g., anti-CD20 antibody), toxin labeled antibody and the like can also be used.

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer, (4) a sustained treatment effect can be designed, (5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to an administration subject simultaneously, or may be administered at different times. The dosage of the concomitant drug may be determined according to the dose clinically set, and can be appropriately selected depending on the administration subject, administration route, disease, combination and the like.

Examples of the administration mode of the combined use of the compound of the present invention and the concomitant drug include the following methods:

(1) The compound of the present invention and the concomitant drug are simultaneously produced to give a single preparation, which is then administered;

(2) The compound of the present invention and the concomitant drug are separately produced to give two kinds of preparations which are administered simultaneously by the same administration route;

(3) The compound of the present invention and the concomitant drug are separately produced to give two kinds of preparations which are administered by the same administration route at different times;

(4) The compound of the present invention and the concomitant drug are separately produced to give two kinds of preparations which are administered simultaneously by different administration routes;

(5) The compound of the present invention and the concomitant drug are separately produced to give two kinds of preparations which are administered by different administration routes at different times (e.g., the compound of the present invention and the concomitant drug are administered in this order, or in the reverse order).

The dose of the concomitant drug is appropriately determined in accordance with its clinical dose and the ratio of the compound of the present invention and the concomitant drug is appropriately determined depending on the administration subject, administration route, target disease, symptom, combination, and the like. For example, when the administration subject is human, the concomitant drug is used in 0.01 to 100 (parts by weight), relative to 1 part by weight of the compound of the present invention.

The combination agent of the present invention has low toxicity and, for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, venous, and the like). An injection can be administered by intravenous, intramuscular, subcutaneous or intra-tissue administration, or directly to the lesion.

As a pharmacologically acceptable carrier which may be used for preparing a preparation of the combination agent of the present invention, those similar to the aforementioned pharmacologically acceptable carriers, which can be used for the production of the medicament of the present invention, can be mentioned. Where necessary, the aforementioned additives that can be used for the production of the medicament of the present invention, such as preservatives, antioxidants, colorants, sweetening agents, adsorbents, wetting agents and the like can also be appropriately used in appropriate amounts.

The compounding ratio of the compound of the present invention to the concomitant drug in the combination agent of the present invention can be appropriately set depending on the administration subject, administration route, diseases and the like.

For example, the content of the compound of the present invention in the combination agent of the present invention varies depending on the dosage form, and is usually from about 0.01 to 100% by weight, preferably from about 0.1 to 50% by weight, further preferably from about 0.5 to 20% by weight, based on the entire preparation.

The content of the concomitant drug in the combination agent of the present invention varies depending on the dosage form, and is usually from about 0.01 to 90% by weight, preferably from about 0.1 to 50% by weight, further preferably from about 0.5 to 20% by weight, based on the entire preparation.

The content of additives in the combination agent of the present invention varies depending on the dosage form, and is usually from about 1 to 99.99% by weight, preferably from about 10 to 90% by weight, based on the entire preparation.

When the compound of the present invention and the concomitant drug are separately prepared, the same content may be adopted.

These preparations can be produced by a method known per se, which is generally employed in the preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin), a stabilizer (e.g., ascorbic acid, sodium pyrosulfite), a surfactant (e.g., Polysorbate 80, macrogol), a solubilizer (e.g., glycerin, ethanol), a buffer (e.g., phosphoric acid and alkali metal salt thereof, citric acid and alkali metal salt thereof), an isotonizing agent (e.g., sodium chloride, potassium chloride, mannitol, sorbitol, glucose), a pH adjuster (e.g., hydrochloric acid, sodium hydroxide), a preservative (e.g., ethyl paraoxybenzoate, benzoic acid, methylparaben, propylparaben, benzyl alcohol), a dissolving agent (e.g., conc, glycerin, meglumine), a solubilizing agent (e.g., propylene glycol, sucrose), a soothing agent (e.g., glucose, benzyl alcohol), and the like, or can be dissolved, suspended or emulsified in a vegetable oil such as olive oil, sesame oil, cotton seed oil, corn oil and the like or a solubilizing agent such as propylene glycol and the like and prepared into an oily injection, whereby an injection is afforded.

In addition, an excipient (e.g., lactose, sucrose, starch), a disintegrating agent (e.g., starch, calcium carbonate), a binder (e.g., starch, gum arabic, carboxymethylcellulose, polyvinylpyrrolidone, hydroxypropylcellulose), a lubricant (e.g., talc, magnesium stearate, polyethylene glycol 6000) and the like may be added to the compound of the present invention or the concomitant drug, and the mixture can be compression-molded, according to a method known per se then if desirable, the molded product can be coated by a method known per se for the purpose of masking of taste, enteric property or durability, to give a preparation for oral administration.

As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid•acrylic acid copolymer, manufactured by Rohm, DE), pigment (e.g., iron oxide red, titanium dioxide) and the like can be used. The preparation for oral administration may be any of an immediate-release preparation and a sustained release preparation.

Moreover, the compound of the present invention and the concomitant drug can be made into an oily or aqueous solid, semisolid or liquid suppository according to a method known per se, by mixing them with an oily substrate, aqueous substrate or aqueous gel substrate.

As the oily substrate, for example, glycerides of higher fatty acid [e.g., cacao butter, Witepsols (manufactured by Dynamit Nobel, Germany)], glycerides of medium chain fatty acid [e.g., Miglyols (manufactured by Dynamit Nobel, Germany)], or vegetable oils (e.g., sesame oil, soybean oil, cotton seed oil), and the like are mentioned.

Furthermore, as the aqueous substrate, for example, polyethylene glycol, propylene glycol and the like are mentioned, and as the aqueous gel substrate, for example, natural gums, cellulose derivatives, vinyl polymers, acrylic acid polymers and the like are mentioned.

As the above-mentioned sustained release preparation, sustained release microcapsules and the like are mentioned.

The sustained release microcapsule can be produced by a method known per se, for example, a method shown in the following [2].

The compound of the present invention is preferably molded into a preparation for oral administration such as a solid preparation (e.g., powder, granule, tablet, capsule) and the like, or molded into a preparation for rectal administration such as a suppository and the like. Particularly, a preparation for oral administration is preferable.

The concomitant drug can be made into the above-mentioned drug form depending on the kind of the drug.

[1] An injection of the compound of the present invention or the concomitant drug, and preparation thereof, [2] a sustained release preparation or immediate-release preparation of the compound of the present invention or the concomitant drug, and preparation thereof, [3] a sublingual tablet, buccal or intraoral quick disintegrating agent of the compound of the present invention or the concomitant drug, and preparation thereof, will be described below specifically.

[1] Injection and Preparation Thereof.

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, salts with organic bases such as tromethamol and the like, etc, are listed.

The concentration of the compound of the present invention or the concomitant drug in an injection is from 0.5 to 50 w/v %, preferably from about 3 to 20 w/v %. The concentration of a benzoate or/and salicylate is from 0.5 to 50 w/v %, preferably from about 3 to 20 w/v %.

Into the injection of the present invention, additives usually used in an injection, for example, a stabilizer (e.g., ascorbic acid, sodium pyrosulfite), a surfactant (e.g., Polysorbate 80, macrogol), a solubilizer (e.g., glycerin, ethanol), a buffer (e.g., phosphoric acid and alkali metal salt thereof, citric acid and alkali metal salt thereof), an isotonizing agent (e.g., sodium chloride, potassium chloride), a dispersing agent (e.g., hydroxypropylmethylcellulose, dextrin), a pH regulator (e.g., hydrochloric acid, sodium hydroxide), a preservative (e.g., ethyl paraoxybenzoate, benzoic acid), a dissolving agent (e.g., conc, glycerin, meglumine), a solubilizing agent (e.g., propylene glycol, sucrose), a soothing agent (e.g., glucose, benzyl alcohol), and the like, can be appropriately blended. These additives are generally blended in a proportion usually used in an injection.

It is advantageous that pH of an injection is controlled from pH 2 to 12, preferably from pH 2.5 to 8.0 by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 min.

Further, a preparation endowed with an antibacterial property of a solution may also be produced so that it can be used as a preparation which is divided and administered multiple-times.

[2] Sustained Release Preparation or Immediate-Release Preparation, and Preparation Thereof.

A sustained release preparation is preferable which is obtained, if desirable, by coating a nucleus containing the compound of the present invention or the concomitant drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacrylic anhydride), glycidyl methacrylate copolymer, particularly, acrylic acid-based polymers such as Eudoragit (manufactured by Rohm Pharma) such as Eudoragit RS-100, RL-100, RS-30D, RL-30D, RL—PO, RS—PO (ethyl acrylate/methyl methacrylate/trimethylammonioethyl methacrylate chloride copolymer), Eudoragit NE-30D (methyl methacrylate/ethyl acrylate copolymer), and the like, hydrogenated oils such as hydrogenated castor oil (e.g., Lubri wax (manufactured by Freund Corporation) and the like), waxes such as carnauba wax, fatty acid glycerin ester, paraffin and the like, polyglycerol ester of fatty acids, and the like.

As the swellable polymer, polymers having an acidic dissociating group and showing pH dependent swell are preferable, and polymers having an acidic dissociating group, which manifest small swelling in acidic regions such as in stomach and large swelling in neutral regions such as in small intestine and large intestine, are preferable.

As such a polymer having an acidic dissociating group and showing pH dependent swell, cross-linkable polyacrylic acid polymers such as, for example, Carbomer 934P, 940, 941, 974P, 980, 1342 and the like, polycarbophil, calcium polycarbophil (last two are manufactured by BF Goodrich), Hiviswako 103, 104, 105, 304 (all are manufactured by Wako Pure Chemical Industries, Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl or carboxyalkyl such as hydroxypropylcellulose, hydroxypropylmethylcellulose, carboxymethylcellulose sodium and the like, methylcellulose, polyvinylpyrrolidone, polyvinyl alcohol, polyethylene glycol and the like can be mentioned.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to about 30% (w/w), preferably from about 3 to about 15% (w/w). The film agent may further contain a hydrophilic substance, and in which case, the content of a hydrophilic substance in the film agent is about 50% (w/w) or less, preferably about 5 to about 40% (w/w), further preferably from about 5 to about 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to about 2000 μm, further preferably, from about 500 to about 1400 μm.

Preparation of the nucleus can be effected by a usual production method. For example, a suitable excipient, binding agent, disintegrating agent, lubricant, stabilizer and the like are mixed with a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropylcellulose, polyethylene glycol, polyvinyl pyrrolidone, Pluronic F68, gum Arabic, gelatin, starch and the like are used. As the disintegrating agent, for example, carboxymethylcellulose calcium (ECG505), croscarmelose sodium (Ac-Di-Sol), crosslinked polyvinylpyrrolidone (Crospovidone), low substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricating agent, polyethylene glycol and the like are used. As the stabilizer, acids such as tartaric acid, citric acid, succinic acid, fumaric acid, maleic acid and the like, are used.

A nucleus can also be prepared by, in addition to the abovementioned productions method, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose or waxes can be used, and the average particle size thereof is preferably from about 100 μm to about 1500 μm.

For separating a drug contained in a nucleus and a film agent, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl or carboxyalkyl are used, more preferably, hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of is these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hydrogenated castor oil, triethyl citrate, cetyl alcohol, stearyl alcohol and the like may also be added as a plasticizer.

After coating with a film agent, if necessary, an antistatic agent such as talc and the like may be mixed.

The immediate-release preparation may be liquid (solution, suspension, emulsion and the like) or solid (particle, pill, tablet and the like). As the immediate-release preparation, oral administration agents and parenteral agents such as an injection and the like are used, and oral administration agents are preferable.

The immediate-release preparation, usually, may contain, in addition to an active component drug, also carriers, additives and excipients conventionally used in the pharmaceutical field (hereinafter, sometimes abbreviated as excipient). The excipient used is not particularly restricted providing it is an excipient ordinarily used as a preparation excipient. For example, as the excipient for an oral solid preparation, lactose, starch, corn starch, crystalline cellulose (Avicel PH101, manufactured by Asahi Kasei Corporation, and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to about 99.4 w/w %, preferably from about 20 to about 98.5 w/w %, further preferably from about 30 to about 97 w/w %, based on the total amount of the immediate-release preparation.

The content of a drug in the immediate-release preparation can be appropriately selected in the range from about 0.5 to about 95 w/w %, preferably from about 1 to about 60 w/w % based on the total amount of the immediate-release preparation.

When the immediate-release preparation is an oral solid preparation, it usually contains, in addition to the above-mentioned components, also a disintegrating agent. As this disintegrating agent, for example, carboxymethylcellulose calcium (ECG-505, manufactured by GOTOKU CHEMICAL CO., LTD.), croscarmelose sodium (e.g., Actisol, manufactured by Asahi Kasei Corporation), crospovidone (e.g.; Kollidon CL, manufactured by BASF), low substituted hydroxypropylcellulose (manufactured by Shin-Etsu Chemical Co., Ltd.), carboxymethylstarch (manufactured by Matsutani Kagaku K.K.), carboxymethylstarch sodium (Exprotab, manufactured by Kimura Sangyo), partially pregelatinized starch (PCS, manufactured by Asahi Kasei Corporation), and the like are used, and for example, those which disintegrate a granule by absorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and blending amount of a drug used, design of releasing property, and the like, and for example, from about 0.05 to about 30 w/w %, preferably from about 0.5 to about 15 w/w %, based on the total amount of the immediate-release preparation.

When the immediate-release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (e.g., Aerosil (manufactured by Nippon Aerosil)), a surfactant (e.g., anionic surfactants such as sodium alkylsulfate and the like, nonionic surfactants such as polyoxyethylene fatty acid ester and polyoxyethylene sorbitan ester of fatty acid, polyoxyethylene castor oil derivatives and the like), a colorant (e.g., tar coloring matter, caramel, iron oxide red, titanium oxide, riboflavins), if necessary, an appetizing agent (e.g., sweetening agent, flavoring agent and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The immediate-release preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a immediate-release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Powrex Corporation), and the like, and then, granulating the mixture by a wet extrusion granulation method, fluidized bed granulation method and the like.

Thus obtained immediate-release preparation and sustained release preparation may be themselves made into products or made into products appropriately together with preparation excipients and the like, separately, by an ordinary method, then, may be administered simultaneously or may be administered in combination at any administration interval, or they may be themselves made into one preparation for oral administration (e.g., granule, fine particle, tablet, capsule and the like) or made into one preparation for oral administration appropriately together with preparation excipients and the like. It may also be permissible that they are made into granules or fine particles, and filled in the same capsule to be used as a preparation for oral administration.

[3] Sublingual Tablet, Buccal or Intraoral Quick Disintegrating Agent and Preparation Thereof.

Sublingual tablet, buccal preparation or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increased in vivo use efficiency, β-cyclodextrin or β-cyclodextrin derivatives (e.g., hydroxypropyl-β-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., microcrystalline cellulose and the like) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolidone, polycarbophil, ascorbic acid, palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, if desired, the above-mentioned auxiliary agents such as a lubricant, isotonizing agent, hydrophilic carrier, water-dispersible polymer, stabilizer, colorant, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably, hydroxypropylcellulose, hydroxypropylmethylcellulose), excipient and the like are dissolved in a solvent such as water and the like, and the resulted solution is cast to give a film. Further, additives such as a plasticizer, stabilizer, antioxidant, preservative, colorant, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into a desired area.

As the preferable intraoral quick disintegrating agent, there are listed solid quick scattering dose agents composed of a network body comprising the compound of the present invention or the concomitant drug, and a water-soluble or water-diffusible carrier which is inert to the compound of the present invention or concomitant drug, are listed. This network body is obtained by sublimating a solvent from the composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include animal proteins or vegetable proteins such as gelatins, dextrins, soybean, wheat and psyllium seed protein and the like; rubber substances such as gum Arabic, guar gum, agar, xanthan and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such a matrix forming agent may be present in addition to a surfactant, or may be present while a surfactant being excluded. The matrix forming agents aid to maintain the compound of the present invention or the concomitant drug in the solution or suspension in diffused condition, in addition to formation of the matrix.

The composition may contain secondary components such as a preservative, antioxidant, surfactant, thickening agent, colorant, pH controlling agent, flavoring agent, sweetening agent, food taste masking agent and the like. As the suitable colorant, there are listed red, black and yellow iron oxides, and FD & C dyes such as FD & C Blue 2, FD & C Red 40 and the like manufactured by Ellis and Everard. Examples of the suitable flavoring agent include mint, raspberry, licorice, orange, lemon, grapefruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1 to about 50% by weight, preferably from about 0.1 to about 30% by weight, and preferable are preparations (such as the above-mentioned sublingual tablet, buccal and the like) which can dissolve 90% or more of the compound of the present invention or the concomitant drug (into water) within the time range of about 1 to about 60 min, preferably of about 1 to about 15 min, more preferably of about 2 to about 5 min, and intraoral quick disintegrating preparations which are disintegrated within the range of 1 to 60 sec, preferably of 1 to 30 sec, further preferably of 1 to 10 sec, after placed in an oral cavity.

The content of the above-mentioned excipient in the whole preparation is from about 10 to about 99% by weight, preferably from about 30 to about 90% by weight. The content of β-cyclodextrin or β-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably, from about 10 to about 70% by weight. The content of the hydrophilic carrier in the whole preparation is from about 0.1 to about 50% by weight, preferably, from about 10 to about 30% by weight. The content of the water-dispersible polymer in the whole preparation is from about 0.1 to about 30% by weight, preferably, from about 10 to about 25% by weight. The content of the stabilizer in the whole preparation is from about 0.1 to about 10% by weight, preferably, from about 1 to about 5% by weight. The above-mentioned preparation may further contain additives such as a colorant, sweetening agent, preservative and the like, if necessary.

The dosage of a combination agent of the present invention differs depending on the kind of a compound of the present invention, age, body weight, condition, drug form, administration method, administration period and the like, and for example, for one cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the administration subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal, which is usually administered once to 4-times in division a day.

In administration of a combination agent of the present invention, the compound of the present invention may be administered after administration of the concomitant drug or the concomitant drug may be administered after administration of the compound of the present invention, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the compound of the present invention or the combination agent of the present invention can be used concurrently with a non-drug therapy. To be precise, the compound of the present invention or the combination agent of the present invention can be combined with a non-drug therapy such as (1) surgery, (2) hypertensive chemotherapy using angiotensin II etc., (3) gene therapy, (4) thelmotherapy, (5) cryotherapy, (6) laser cauterization, (7) radiotherapy, and the like.

For example, by using the compound of the present invention or the combination agent of the present invention before or after an surgery and the like, or before or after a combined treatment of two or three kinds thereof, effects such as prevention of emergence of resistance, prolongation of Disease-Free Survival, suppression of cancer metastasis or recurrence, prolongation of life and the like can be afforded.

In addition, it is possible to combine a treatment with the compound of the present invention or the combination agent of the present invention with a supportive therapy [(i) administration of antibiotic (e.g., β-lactam type such as pansporin etc., macrolide type such as clarithromycin etc.) for the complication with various infectious diseases, (ii) administration of high-calorie transfusion, amino acid preparation or general vitamin preparation for the improvement of malnutrition, (iii) administration of morphine for pain mitigation, (iv) administration of a medicament for ameliorating side effects such as nausea, vomiting, anorexia, diarrhea, leucopenia, thrombocytopenia, decreased hemoglobin concentration, hair loss, hepatopathy, renopathy, DIC, fever and the like and (v) administration of a medicament for suppressing multiple drug resistance of cancer and the like].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the compound of the present invention or the combination agent of the present invention before the surgery, etc., for example, it can be administrated 1-time about 30 min to 24 hrs before the surgery, etc., or in 1 to 3 cycles about 3 months to 6 months before the surgery, etc. In this way, the surgery, etc, can be conducted easily because, for example, a cancer tissue would be reduced by administering the compound of the present invention or the combination agent of the present invention before the surgery, and the like.

As a period for administering the compound of the present invention or the combination agent of the present invention after the surgery, etc., for example, it can be administrated repeatedly per a few weeks to 3 months, about 30 min to 24 hrs after the surgery, and the like. In this way, it enhances the effect of the surgery, etc, by administering the compound of the present invention or the combination agent of the present invention after the surgery, and the like.

EXAMPLES

The present invention is explained in more detail in the following by referring to Reference Examples, Examples, Formulation Examples, Experimental Examples and Test Examples, which are not to be construed as limitative.

LC/MS analysis in the following Examples was performed under the following conditions.
measurement device: Waters MUX system
column: CAPCELL PAK C18UG120 manufactured by Shiseido Co., Ltd., 1.5×35 mm
solvent: SOLUTION A: 5 mM aqueous ammonium acetate solution 98%-acetonitrile 2%; SOLUTION B: 5 mM aqueous ammonium acetate solution 5%-acetonitrile 95% (both in volume ratio)
gradient cycle: 0.0 min (SOLUTION A/SOLUTION B=100/0), 2.00 min (SOLUTION A/SOLUTION B=0/100), 3.00 min (SOLUTION A/SOLUTION B=0/100), 3.01 min (SOLUTION A/SOLUTION B=100/0), 3.80 min (SOLUTION A/SOLUTION B=100/0)
flow rate: 0.5 mL/min
detection method: UV 220 nm
MS conditions: ionization method: ESI
  Purification by preparative HPLC in the following Examples was performed under the following conditions, instrument: High-throughput purification system (Gilson Inc.) column: YMC CombiPrep ODS-A S-5 50×20 mm
solvent: SOLUTION A: 10 mM aqueous ammonium carbonate solution; SOLUTION B: acetonitrile
typical gradient cycle: 0 min (SOLUTION A/SOLUTION B=98/2), 1.00 min (SOLUTION A/SOLUTION B=98/2), 4.70 min (SOLUTION A/SOLUTION B=0/100), 6.40 min (SOLUTION A/SOLUTION B=0/100), 6.50 min (SOLUTION A/SOLUTION B=98/2), 6.60 min (SOLUTION A/SOLUTION B=98/2)
flow rate: 25 mL/min
detection method: UV 220 nm/254 nm Example 1

Production of N-(5-{[4-fluoro-3-({[4-(trifluoromethyl)phenyl]carbamoyl}amino)phenyl](methyl)amino}[1,3]thiazolo[5,4-b]pyridin-2-yl)cyclopropanecarboxamide

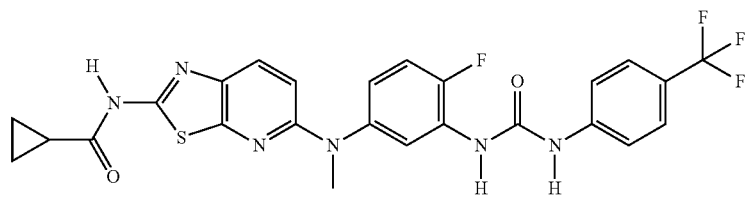 [SMILES: CN(c1ccc(F)c(NC(=O)Nc2ccc(C(F)(F)F)cc2)c1)c1ccc2nc(NC(=O)C3CC3)sc2n1]

(i) Production of tert-butyl (4-fluoro-3-nitrophenyl)carbamate

To a solution of 4-fluoro-3-nitroaniline (1.56 g, 10 mmol) in tert-butanol (15 mL) was added di-tert-butyl bicarbonate (2.40 g, 11 mmol), and the mixture was stirred at 60° C. for 22 hr. The reaction mixture was concentrated under reduced pressure and the obtained residue was triturated with hexane to give the title compound (2.38 g, 93%) as a yellow-brown solid.

$^1$H-NMR (DMSO-$d_6$, 300 MHz) δ 1.49 (9H, s), 7.50 (1H, t, J=10.2 Hz), 7.65-7.81 (1H, m), 8.36 (1H, d, J=6.8 Hz), 9.87 (1H, s).

(ii) Production of tert-butyl (4-fluoro-3-nitrophenyl)methylcarbamate

To a suspension of tert-butyl (4-fluoro-3-nitrophenyl)carbamate (1.00 g, 3.90 mmol) and cesium carbonate (1.53 g, 4.7 mmol) in N,N-dimethylformamide (5 mL) was added methyl iodide (0.37 mL, 5.94 mmol), and the mixture was stirred at room temperature for 6 hr. The reaction mixture was suspended in ethyl acetate (5 mL), washed with water (5 mL) and saturated brine (5 mL), and dried over anhydrous magnesium sulfate. The insoluble material was filtered off, and the filtrate was concentrated under reduced pressure to give the title compound (1.0 g, 95%) as a brown oil. This was used for the next reaction without subjecting to further purification operation.

$^1$H-NMR (DMSO-$d_6$, 300 MHz) δ 1.42 (9H, s), 3.23 (3H, s), 7.57 (1H, dd, J=11.0, 9.1 Hz), 7.76 (1H, ddd, J=9.1, 4.0, 2.8 Hz), 8.10 (1H, dd, J=6.8, 2.8 Hz).

(iii) Production of tert-butyl (3-amino-4-fluorophenyl)methylcarbamate

To a solution of tert-butyl (4-fluoro-3-nitrophenyl)methylcarbamate (1.0 g, 3.70 mmol) in methanol (4 mL) was added 10% palladium-carbon (150 mg), and the mixture was stirred at room temperature under a hydrogen atmosphere (1 atm) for 18 hr. The insoluble material was filtered off, and the filtrate was concentrated under reduced pressure. The obtained residue was purified by silica gel column chromatography (ethyl acetate), and the obtained solution was concentrated under reduced pressure to give the title compound (0.88 g, 99%) as a brown oil.

$^1$H-NMR (DMSO-$d_6$, 300 MHz) δ 1.37 (9H, s), 3.08 (3H, s), 5.14 (2H, s), 6.36 (1H, ddd, J=8.6, 4.0, 2.7 Hz), 6.64 (1H, dd, J=8.6, 2.7 Hz), 6.91 (1H, dd, J=11.1, 8.6 Hz).

(iv) Production of tert-butyl {4-fluoro-3-[(trifluoroacetyl)amino]phenyl}methylcarbamate To a solution of tert-butyl (3-amino-4-fluorophenyl)methylcarbamate (44 g, 183 mmol) in tetrahydrofuran (440 mL) was added trifluoroacetic anhydride (30.5 mL, 220 mmol) at 4° C. and, after the completion of the dropwise addition, the mixture was stirred at 10° C. for 18 hr. The reaction mixture was diluted with ethyl acetate (440 mL), washed with saturated aqueous sodium hydrogen carbonate solution (440 mL), and the obtained aqueous layer was extracted with ethyl acetate (100 mL). The combined organic layer was washed with saturated brine (440 mL), and dried over anhydrous magnesium sulfate. The obtained solution was purified by silica gel column chromatography (ethyl acetate). The obtained solution was concentrated under reduced pressure to give the title compound (60.3 g, 98%) as a pale-yellow solid.

$^1$H-NMR (DMSO-$d_6$, 300 MHz) δ 1.39 (9H, s), 3.17 (3H, s), 7.24-7.38 (2H, m), 7.42 (1H, dd, J=6.8, 1.9 Hz), 11.29 (1H, s).

(v) Production of 2,2,2-trifluoro-N-[2-fluoro-5-(methylamino)phenyl]acetamide To tert-butyl {4-fluoro-3-[(trifluoroacetyl)amino]phenyl}methylcarbamate (2.5 g, 7.43 mmol) was added trifluoroacetic acid (6 ml) at 4° C. to give a solution, which was stirred at 10° C. for 2 hr. The reaction mixture was concentrated under reduced pressure, and the obtained residue was diluted with ethyl acetate (10 mL), washed with saturated aqueous sodium hydrogen carbonate solution (10 mL) and saturated brine (10 mL), and dried over anhydrous magnesium sulfate. The obtained solution was purified by silica gel column chromatography (ethyl acetate). The obtained solution was concentrated under reduced pressure to give the title compound (1.75 g, 99%) as a pale-yellow powder.

$^1$H-NMR (DMSO-$d_6$, 300 MHz) δ 2.64 (3H, d, J=5.1 Hz), 5.74 (1H, q, J=5.1 Hz), 6.47 (1H, ddd, J=9.0, 3.9, 3.0 Hz), 6.54 (1H, dd, J=6.2, 3.0 Hz), 7.05 (1H, dd, J=10.2, 9.0 Hz), 11.05 (1H, s).

(vi) Production of 2,2,2-trifluoro-N-{2-fluoro-5-[methyl(5-nitropyridin-2-yl)amino]phenyl}acetamide A solution of 2-chloro-5-nitropyridine (201 mg, 1.27 mmol) and 2,2,2-trifluoro-N-[2-fluoro-5-(methylamino)phenyl]acetamide (300 mg, 1.27 mmol) in N,N-dimethylformamide (1.5 mL) was stirred at 140° C. for 22 hr. The reaction mixture was cooled to room temperature, suspended in ethyl acetate (5 mL), washed with saturated aqueous sodium hydrogen carbonate solution (5 mL) and saturated brine (5 mL), and dried over anhydrous sodium sulfate. The insoluble material was filtered off, and the filtrate was concentrated under reduced pressure. The obtained residue was crystallized from ethyl acetate/hexane to give the title compound (221 mg, 49%) as yellow crystals.

$^1$H-NMR (DMSO-$d_6$, 300 MHz) δ 3.50 (3H, s), 6.53 (1H, d, J=9.4 Hz), 7.37-7.66 (3H, m), 8.21 (1H, dd, J=9.4, 2.7 Hz), 9.03 (1H, d, J=2.7 Hz), 11.43 (1H, s).

EXAMPLES

The present invention is explained in more detail in the following by referring to Reference Examples, Examples, Formulation Examples, Experimental Examples and Test Examples, which are not to be construed as limitative.

LC/MS analysis in the following Examples was performed under the following conditions.

measurement device: Waters MUX system column: CAPCELL PAK C18UG120 manufactured by Shiseido Co., Ltd., 1.5×35 mm solvent: SOLUTION A: 5 mM aqueous ammonium acetate solution 98%-acetonitrile 2%; SOLUTION B: 5 mM aqueous ammonium acetate solution 5%-acetonitrile 95% (both in volume ratio)

gradient cycle: 0.0 min (SOLUTION A/SOLUTION B=100/0), 2.00 min (SOLUTION A/SOLUTION B=0/100), 3.00 min (SOLUTION A/SOLUTION B=0/100), 3.01 min (SOLUTION A/SOLUTION B=100/0), 3.80 min (SOLUTION A/SOLUTION B=100/0)

flow rate: 0.5 mL/min detection method: UV 220 nm

MS conditions: ionization method: ESI

Purification by preparative HPLC in the following Examples was performed under the following conditions, instrument: High-throughput purification system (Gilson Inc.) column: YMC CombiPrep ODS-A S-5 μm, 50×20 mm solvent: SOLUTION A: 10 mM aqueous ammonium carbonate solution; SOLUTION B: acetonitrile typical gradient cycle: 0 min (SOLUTION A/SOLUTION B=98/2), 1.00 min (SOLUTION A/SOLUTION B=98/2), 4.70 min (SOLUTION A/SOLUTION B=0/100), 6.40 min (SOLUTION A/SOLUTION B=0/100), 6.50 min (SOLUTION A/SOLUTION B=98/2), 6.60 min (SOLUTION A/SOLUTION B=98/2)

flow rate: 25 mL/min detection method: UV 220 nm/254 nm

Example 1

Production of N-(5-{[4-fluoro-3-({[4-(trifluoromethyl)phenyl]carbamoyl}amino)phenyl](methyl)amino}[1,3]thiazolo[5,4-b]pyridin-2-yl)cyclopropanecarboxamide

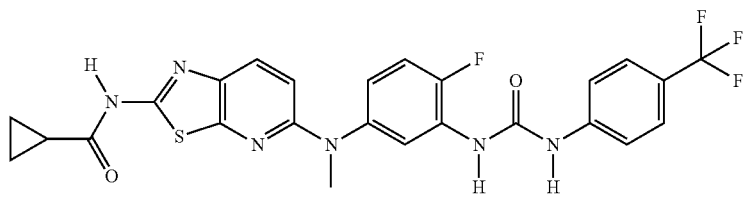 [SMILES: CN(c1ccc(F)c(NC(=O)Nc2ccc(C(F)(F)F)cc2)c1)c1ccc2nc(NC(=O)C3CC3)sc2n1]

(i) Production of tert-butyl (4-fluoro-3-nitrophenyl)carbamate

To a solution of 4-fluoro-3-nitroaniline (1.56 g, 10 mmol) in tert-butanol (15 mL) was added di-tert-butyl bicarbonate (2.40 g, 11 mmol), and the mixture was stirred at 60° C. for 22 hr. The reaction mixture was concentrated under reduced pressure and the obtained residue was triturated with hexane to give the title compound (2.38 g, 93%) as a yellow-brown solid.

$^1$H-NMR (DMSO-$d_6$, 300 MHz) δ 1.49 (9H, s), 7.50 (1H, t, J=10.2 Hz), 7.65-7.81 (1H, m), 8.36 (1H, d, J=6.8 Hz), 9.87 (1H, s).

(ii) Production of tert-butyl (4-fluoro-3-nitrophenyl)methylcarbamate

To a suspension of tert-butyl (4-fluoro-3-nitrophenyl)carbamate (1.00 g, 3.90 mmol) and cesium carbonate (1.53 g, 4.7 mmol) in N,N-dimethylformamide (5 mL) was added methyl iodide (0.37 ml, 5.94 mmol), and the mixture was stirred at room temperature for 6 hr. The reaction mixture was suspended in ethyl acetate (5 mL), washed with water (5 mL) and saturated brine (5 mL), and dried over anhydrous magnesium sulfate. The insoluble material was filtered off, and the filtrate was concentrated under reduced pressure to give the title compound (1.0 g, 95%) as a brown oil. This was used for the next reaction without subjecting to further purification operation.

$^1$H-NMR (DMSO-$d_6$, 300 MHz) δ 1.42 (9H, s), 3.23 (3H, s), 7.57 (1H, dd, J=11.0, 9.1 Hz), 7.76 (1H, ddd, J=9.1, 4.0, 2.8 Hz), 8.10 (1H, dd, J=6.8, 2.8 Hz).

(iii) Production of tert-butyl (3-amino-4-fluorophenyl)methylcarbamate

To a solution of tert-butyl (4-fluoro-3-nitrophenyl)methylcarbamate (1.0 g, 3.70 mmol) in methanol (4 mL) was added 10% palladium-carbon (150 mg), and the mixture was stirred at room temperature under a hydrogen atmosphere (1 atm) for 18 hr. The insoluble material was filtered off, and the filtrate was concentrated under reduced pressure. The obtained residue was purified by silica gel column chromatography (ethyl acetate), and the obtained solution was concentrated under reduced pressure to give the title compound (0.88 g, 99%) as a brown oil.

$^1$H-NMR (DMSO-$d_6$, 300 MHz) δ 1.37 (9H, s), 3.08 (3H, s), 5.14 (2H, s), 6.36 (1H, ddd, J=8.6, 4.0, 2.7 Hz), 6.64 (1H, dd, J=8.6, 2.7 Hz), 6.91 (1H, dd, J=11.1, 8.6 Hz).

(iv) Production of tert-butyl {4-fluoro-3-[(trifluoroacetyl)amino]phenyl}methylcarbamate To a solution of tert-butyl (3-amino-4-fluorophenyl)methylcarbamate (44 g, 183 mmol) in tetrahydrofuran (440 mL) was added trifluoroacetic anhydride (30.5 mL, 220 mmol) at 4° C. and, after the completion of the dropwise addition, the mixture was stirred at 10° C. for 18 hr. The reaction mixture was diluted with ethyl acetate (440 mL), washed with saturated aqueous sodium hydrogen carbonate solution (440 mL), and the obtained aqueous layer was extracted with ethyl acetate (100 mL). The combined organic layer was washed with saturated brine (440 mL), and dried over anhydrous magnesium sulfate. The obtained solution was purified by silica gel column chromatography (ethyl acetate). The obtained solution was concentrated under reduced pressure to give the title compound (60.3 g, 98%) as a pale-yellow solid.

$^1$H-NMR (DMSO-$d_6$, 300 MHz) δ 1.39 (9H, s), 3.17 (3H, s), 7.24-7.38 (2H, m), 7.42 (1H, dd, J=6.8, 1.9 Hz), 11.29 (1H, s).

(v) Production of 2,2,2-trifluoro-N-[2-fluoro-5-(methylamino)phenyl]acetamide To tert-butyl {4-fluoro-3-[(trifluoroacetyl)amino]phenyl}methylcarbamate (2.5 g, 7.43 mmol) was added trifluoroacetic acid (6 mL) at 4° C. to give a solution, which was stirred at 10° C. for 2 hr. The reaction mixture was concentrated under reduced pressure, and the obtained residue was diluted with ethyl acetate (10 mL), washed with saturated aqueous sodium hydrogen carbonate solution (10 mL) and saturated brine (10 mL), and dried over anhydrous magnesium sulfate. The obtained solution was purified by silica gel column chromatography (ethyl acetate). The obtained solution was concentrated under reduced pressure to give the title compound (1.75 g, 99%) as a pale-yellow powder.

$^1$H-NMR (DMSO-$d_6$, 300 MHz) δ 2.64 (3H, d, J=5.1 Hz), 5.74 (1H, q, J=5.1 Hz), 6.47 (1H, ddd, J=9.0, 3.9, 3.0 Hz), 6.54 (1H, dd, J=6.2, 3.0 Hz), 7.05 (1H, dd, J=10.2, 9.0 Hz), 11.05 (1H, s).

(vi) Production of 2,2,2-trifluoro-N-{2-fluoro-5-[methyl(5-nitropyridin-2-yl)amino]phenyl}acetamide A solution of 2-chloro-5-nitropyridine (201 mg, 1.27 mmol) and 2,2,2-trifluoro-N-[2-fluoro-5-(methylamino)phenyl]acetamide (300 mg, 1.27 mmol) in N,N-dimethylformamide (1.5 mL) was stirred at 140° C. for 22 hr. The reaction mixture was cooled to room temperature, suspended in ethyl acetate (5 mL), washed with saturated aqueous sodium hydrogen carbonate solution (5 mL) and saturated brine (5 ml), and dried over anhydrous sodium sulfate. The insoluble material was filtered off, and the filtrate was concentrated under reduced pressure. The obtained residue was crystallized from ethyl acetate/hexane to give the title compound (221 mg, 49%) as yellow crystals.

$^1$H-NMR (DMSO-d$_6$, 300 MHz) δ 3.50 (3H, s), 6.53 (1H, d, J=9.4 Hz), 7.37-7.66 (3H, m), 8.21 (1H, dd, J=9.4, 2.7 Hz), 9.03 (1H, d, J=2.7 Hz), 11.43 (1H, s).

(vii) Production of N-{5-[(5-aminopyridin-2-yl)(methyl)amino]-2-fluorophenyl}-2,2,2-trifluoroacetamide To a solution of 2,2,2-trifluoro-N-{2-fluoro-5-[methyl(5-nitropyridin-2-yl)amino]phenyl}acetamide (18.0 g, 50.2 mmol) in ethanol (100 mL)/tetrahydrofuran (20 mL) was added 10% palladium-carbon (1.8 g), and the mixture was stirred at room temperature for 14 hr under a hydrogen atmosphere (1 atm). The insoluble material was filtered off, and the filtrate was concentrated under reduced pressure. The obtained residue was crystallized from ethyl acetate/hexane to give the title compound (21.2 g, 68%) as colorless crystals.

$^1$H-NMR (DMSO-d$_6$, 300 MHz) δ 3.23 (3H, s), 4.94 (2H, br s), 6.71 (1H, d, J=8.7 Hz), 6.88-6.99 (2H, m), 7.03 (1H, dd, J=6.6, 2.4 Hz), 7.21 (1H, dd, J=10.0, 9.0 Hz), 7.69 (1H, d, J=2.4 Hz), 11.15 (1H, br s).

(viii) Production of N-{5-[(2-amino[1,3]thiazolo[5,4-b]pyridin-5-yl)(methyl)amino]-2-fluorophenyl}-2,2,2-trifluoroacetamide Potassium thiocyanate (2.96 g, 30.5 mmol) was suspended in acetic acid (20 mL), and the suspension was stirred at room temperature for 10 min. To the obtained solution was added N-{5-[(5-aminopyridin-2-yl)(methyl)amino]-2-fluorophenyl}-2,2,2-trifluoroacetamide (2.0 g, 6.96 mmol), and the mixture was further stirred at room temperature for 10 min. The obtained solution was slowly added dropwise to a solution of bromine (1.17 g, 7.30 mmol) in acetic acid (10 mL). After the completion of the dropwise addition, the mixture was stirred at room temperature for 20 hr. The resultant black insoluble material was filtered off, and washed with acetic acid. The combined filtrate and washing were concentrated under reduced pressure. The obtained residue was suspended in ethyl acetate (100 mL), washed with saturated aqueous sodium hydrogen carbonate solution (70 mL) and saturated brine (100 mL), and dried over anhydrous magnesium sulfate. The insoluble material was filtered off, and the filtrate was concentrated under reduced pressure. The obtained residue was purified by basic silica gel column chromatography (hexane/ethyl acetate=40/60→0/100), and the obtained solution was concentrated under reduced pressure. The residue was crystallized from ethyl acetate/hexane to give the title compound (1.00 g, 43%) as a colorless powder.

$^1$H-NMR (DMSO-d$_6$, 300 MHz) δ 3.34 (3H, s), 6.57 (1H, d, J=8.7 Hz), 7.22 (1H, dd, J=4.2, 2.7 Hz), 7.29-7.40 (4H, m), 7.45 (1H, d, J=8.7 Hz), 11.28 (1H, s).

(ix) Production of N-{5-[{4-fluoro-3-[(trifluoroacetyl)amino]phenyl}(methyl)amino][1,3]thiazolo[5,4-b]pyridin-2-yl}cyclopropanecarboxamide To a solution of N-{5-[(2-amino[1,3]thiazolo[5,4-b]pyridin-5-yl)(methyl)amino]-2-fluorophenyl}-2,2,2-trifluoroacetamide (385 mg, 1.00 mmol) in pyridine (10 mL) was added cyclopropanecarbonyl chloride (144 μL, 1.60 mmol) at 4° C., and the mixture was stirred at room temperature for 1 hr. The reaction mixture was concentrated under reduced pressure, and the residue was suspended in ethyl acetate (10 mL). The obtained suspension was washed with saturated aqueous sodium hydrogen carbonate solution (10 mL) and saturated brine (10 mL), and dried over anhydrous magnesium sulfate. The insoluble material was filtered off, and the filtrate was concentrated under reduced pressure. The obtained residue was purified by basic silica gel column chromatography (hexane/ethyl acetate=80/20→0/100), and the obtained solution was concentrated under reduced pressure to give the title compound (250 mg, 59%) as a colorless powder.

$^1$H-NMR (DMSO-d$_6$, 300 MHz) δ 0.85-1.04 (4H, m), 1.86-2.10 (1H, m), 3.41 (3H, s), 6.65 (1H, d, J=9.0 Hz), 7.28-7.59 (3H, m), 7.80 (1H, d, J=9.0 Hz), 11.35 (1H, s), 12.47 (1H, s).

(x) Production of N-{5-[(3-amino-4-fluorophenyl)(methyl)amino][1,3]thiazolo[5,4-b]pyridin-2-yl}cyclopropanecarboxamide To a suspension of sodium borohydride (3.34 g, 88.2 mmol) in ethanol (40 mL) were added methanol (1 mL) and N-[5-[{4-fluoro-3-[(trifluoroacetyl)amino]phenyl}(methyl)amino][1,3]thiazolo[5,4-b]pyridin-2-yl]cyclopropanecarboxamide (1.71 g, 3.77 mmol) at 4° C., and the mixture was stirred for 30 min. The reaction mixture was poured into a two-layer solvent of ethyl acetate (200 mL) and 5% aqueous ammonium chloride solution (200 mL), and the mixture was vigorously stirred at room temperature for 5 min. The aqueous layer was separated, and extracted with ethyl acetate (200 mL). The combined organic layer was washed with saturated aqueous sodium hydrogen carbonate solution (200 mL) and saturated brine (200 mL), and dried over anhydrous magnesium sulfate. The insoluble material was filtered off, and the filtrate was concentrated under reduced pressure. The residue was purified by silica gel column chromatography (hexane/ethyl acetate=80/20→60/40), and the obtained solution was concentrated under reduced pressure to give the title compound (1.19 g, 88%) as a colorless powder.

$^1$H-NMR (DMSO-d$_6$, 300 MHz) δ 0.71-1.08 (4H, m), 1.83-2.06 (1H, m), 3.33 (3H, s), 5.27 (2H, s), 6.34-6.47 (1H, m), 6.50 (1H, d, J=9.1 Hz), 6.67 (1H, dd, J=8.4, 2.6 Hz), 7.05 (1H, dd, J=11.3, 8.4 Hz), 7.72 (1H, d, J=9.1 Hz), 12.41 (1H, s).

(xi) Production of N-(5-{[4-fluoro-3-({[4-(trifluoromethyl)phenyl]carbamoyl}amino)phenyl](methyl)amino}[1,3]thiazolo[5,4-b]pyridin-2-yl)cyclopropanecarboxamide N-{5-[(3-Amino-4-fluorophenyl)(methyl)amino][1,3]thiazolo[5,4-b]pyridin-2-yl}cyclopropanecarboxamide (120 mg, 0.33 mmol) was dissolved in N,N-dimethylformamide (2.0 mL), 1-isocyanato-4-(trifluoromethyl)benzene (58 μL, 0.40 mmol) was added, and the mixture was stirred at room temperature for 12 hr. The reaction mixture was diluted with ethyl acetate (10 mL), and washed successively with saturated aqueous sodium hydrogen carbonate solution (10 ml) and saturated brine (10 mL). The organic layer was dried over anhydrous sodium sulfate and concentrated under reduced pressure. The obtained residue was purified by basic silica gel column chromatography (ethyl acetate/hexane=30/70→100/0), and the obtained solution was concentrated under reduced pressure. The residue was recrystallized from ethyl acetate to give the title compound (130 mg, 71%) as a colorless powder.

$^1$H-NMR (DMSO-d$_6$, 300 MHz) δ 0.88-1.01 (4H, m), 1.87-2.11 (1H, m), 3.41 (3H, s), 6.60 (1H, d, J=9.0 Hz), 6.86-7.10 (1H, m), 7.34 (1H, dd, J=11.0, 8.8 Hz), 7.63 (4H, s), 7.76 (1H, d, J=9.0 Hz), 8.13 (1H, dd, J=7.4, 2.7 Hz), 8.79 (1H, s), 9.49 (1H, s), 12.45 (1H, s).

Example 2

Production of N-{5-[(3-{[(3-tert-butyl-1-phenyl-1H-pyrazol-5-yl)carbamoyl]amino}-4-fluorophenyl)(methyl)amino][1,3]thiazolo[5,4-b]pyridin-2-yl}cyclopropanecarboxamide hydrochloride

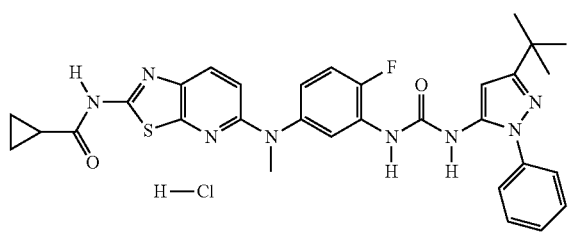 [SMILES: CN(c1ccc(F)c(NC(=O)Nc2cc(C(C)(C)C)nn2-c2ccccc2)c1)c1ccc2nc(NC(=O)C3CC3)sc2n1 ; Cl]

N-{5-[(3-Amino-4-fluorophenyl)(methyl)amino][1,3]thiazolo[5,4-b]pyridin-2-yl}cyclopropanecarboxamide (150 mg, 0.42 mmol) produced in Example 1(x) was dissolved in dimethyl sulfoxide (2.0 mL), 2,2,2-trichloroethyl (3-tert-butyl-1-phenyl-1H-pyrazol-5-yl)carbamate (170 mg, 0.44 mmol) and triethylamine (64 μL, 0.46 mmol) were added, and the mixture was stirred at 60° C. for 4 hr. The reaction mixture was cooled to room temperature, diluted with ethyl acetate (10 mL), and washed successively with 5% aqueous sodium hydrogen carbonate solution (10 mL) and saturated brine (10 mL). The organic layer was dried over anhydrous sodium sulfate, and concentrated under reduced pressure. The obtained residue was purified by basic silica gel column chromatography (ethyl acetate/hexane=30/70→80/20), and the obtained solution was concentrated under reduced pressure. The residue was treated with 4N hydrogen chloride/ethyl acetate to give hydrochloride. The obtained residue was recrystallized from ethyl acetate to give the title compound (136 mg, 51%) as a pale-yellow powder.

$^1$H-NMR (DMSO-$d_6$, 300 MHz) δ 0.89-0.99 (4H, m), 1.25 (9H, s), 1.92-2.07 (1H, m), 3.39 (3H, s), 6.37 (1H, s), 6.56 (1H, d, J=9.1 Hz), 6.93-7.00 (1H, m), 7.31 (1H, dd, J=11.1, 8.7 Hz), 7.38-7.47 (1H, m), 7.48-7.60 (4H, m), 7.76 (1H, d, J=9.1 Hz), 8.11 (1H, dd, J=7.4, 2.6 Hz), 8.99 (1H, s), 9.12 (1H, d, J=1.9 Hz), 12.47 (1H, s).

Example 3

Production of N-{5-[(3-{[(4-tert-butylphenyl)carbamoyl]amino-}-4-fluorophenyl)(methyl)amino][1,3]thiazolo[5,4-b]pyridin-2-yl}cyclopropanecarboxamide

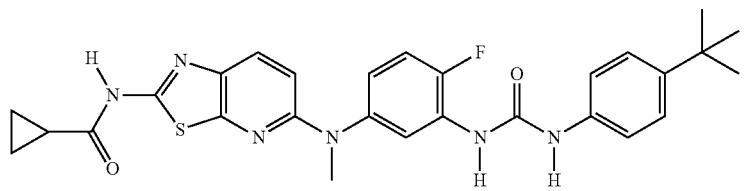 [SMILES: CN(c1ccc(F)c(NC(=O)Nc2ccc(C(C)(C)C)cc2)c1)c1ccc2nc(NC(=O)C3CC3)sc2n1]

N-{5-[(3-Amino-4-fluorophenyl)(methyl)amino][1,3]thiazolo[5,4-b]pyridin-2-yl}cyclopropanecarboxamide (120 mg, 0.34 mmol) produced in Example 1(x) was dissolved in N,N-dimethylformamide (1.5 mL), 1-tert-butyl-4-isocyanatobenzene (72 μL, 0.40 mmol) was added, and the mixture was stirred at room temperature for 6 hr. The reaction mixture was diluted with ethyl acetate (10 mL), and washed successively with saturated aqueous sodium hydrogen carbonate solution (10 mL) and saturated brine (10 mL). The organic layer was dried over anhydrous sodium sulfate and concentrated under reduced pressure. The obtained residue was purified by basic silica gel column chromatography (ethyl acetate/hexane=50/50→100/0), and the obtained solution was concentrated under reduced pressure. The residue was recrystallized from ethyl acetate to give the title compound (31 mg, 17%) as a colorless powder.

$^1$H-NMR (DMSO-$d_6$, 300 MHz) δ 0.71-1.06 (4H, m), 1.25 (9H, s), 1.86-2.10 (1H, m), 3.40 (3H, s), 6.58 (1H, d, J=9.1 Hz), 6.86-7.06 (1H, m), 7.20-7.46 (5H, m), 7.75 (1H, d, J=9.1 Hz), 8.15 (1H, dd, J=7.4, 2.6 Hz), 8.63 (1H, d, J=2.6 Hz), 9.03 (1H, s), 12.44 (1H, br s).

Example 4

Production of N-(5-{[3-({[4-chloro-3-(trifluoromethyl)phenyl]carbamoyl}amino)-4-fluorophenyl](methyl)amino}[1,3]thiazolo[5,4-b]pyridin-2-yl)cyclopropanecarboxamide

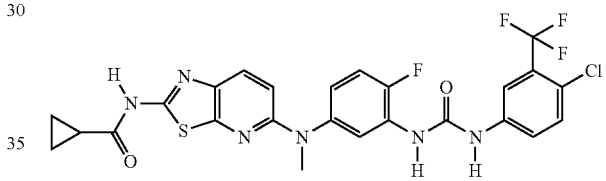

N-{5-[(3-Amino-4-fluorophenyl)(methyl)amino][1,3]thiazolo[5,4-b]pyridin-2-yl}cyclopropanecarboxamide (120 mg, 0.34 mmol) produced in Example 1(x) was dissolved in N,N-dimethylformamide (1.5 mL), 1-chloro-4-isocyanato-2-(trifluoromethyl)benzene (89 mg, 0.40 mmol) was added, and the mixture was stirred at room temperature for 6 hr. The reaction mixture was diluted with ethyl acetate (10 mL), and washed successively with saturated aqueous sodium hydrogen carbonate solution (10 mL) and saturated brine (10 mL). The organic layer was dried over anhydrous sodium sulfate and concentrated under reduced pressure. The obtained residue was purified by basic silica gel column chromatography (ethyl acetate/hexane=50/50→100/0), and the obtained solution was concentrated under reduced pressure. The residue was recrystallized from ethyl acetate to give the title compound (140 mg, 72%) as a colorless powder.

$^1$H-NMR (DMSO-$d_6$, 300 MHz) δ 0.80-1.04 (4H, m), 1.87-2.05 (1H, m), 3.40 (3H, s), 6.58 (1H, d, J=9.1 Hz), 6.87-7.08% (1H, m), 7.35 (1H, dd, J=11.0, 8.8 Hz), 7.50-7.68 (2H, m), 7.76 (1H, d, J=9.1 Hz), 7.98-8.19 (2H, m), 8.79 (1H, s), 9.54 (1H, s), 12.44 (1H, br s).

Example 5

Production of N-(5-{[3-({[2-chloro-5-(trifluoromethyl)phenyl]carbamoyl}amino)-4-fluorophenyl](methyl)amino}[1,3]thiazolo[5,4-b]pyridin-2-yl)cyclopropanecarboxamide

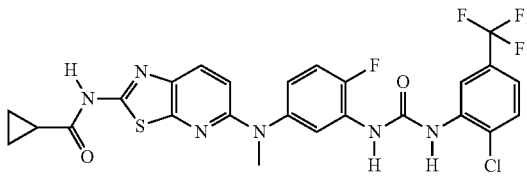 [SMILES: CN(c1ccc(F)c(NC(=O)Nc2cc(C(F)(F)F)ccc2Cl)c1)c1ccc2nc(NC(=O)C3CC3)sc2n1]

N-{5-[(3-Amino-4-fluorophenyl)(methyl)amino][1,3]thiazolo[5,4-b]pyridin-2-yl}cyclopropanecarboxamide (120 mg, 0.34 mmol) produced in Example 1(x) was dissolved in N,N-dimethylformamide (1.5 mL), 1-chloro-2-isocyanato-4-(trifluoromethyl)benzene (60 μL, 0.40 mmol) was added, and the mixture was stirred at room temperature for 6 hr. The reaction mixture was diluted with ethyl acetate (10 mL), and washed successively with saturated aqueous sodium hydrogen carbonate solution (10 mL) and saturated brine (10 mL). The organic layer was dried over anhydrous sodium sulfate and concentrated under reduced pressure. The obtained residue was purified by basic silica gel column chromatography (ethyl acetate/hexane=50/50→100/0), and the obtained solution was concentrated under reduced pressure. The residue was recrystallized from ethyl acetate to give the title compound (152 mg, 78%) as a colorless powder.

$^1$H-NMR (DMSO-$d_6$, 300 MHz) δ 0.77-1.05 (4H, m), 1.88-2.05 (1H, m), 3.41 (3H, s), 6.56 (1H, d, J=9.1 Hz), 6.84-7.09 (1H, m), 7.21-7.51 (2H, m), 7.61-7.87 (2H, m), 8.14 (1H, dd, J=7.2, 2.6 Hz), 8.55 (1H, d, J=2.1 Hz), 9.14 (1H, s), 9.65 (1H, s), 12.44 (1H, br s).

Example 6

Production of N-(5-{[3-({[2-chloro-4-(trifluoromethyl)phenyl]carbamoyl}amino)-4-fluorophenyl](methyl)amino}[1,3]thiazolo[5,4-b]pyridin-2-yl)cyclopropanecarboxamide

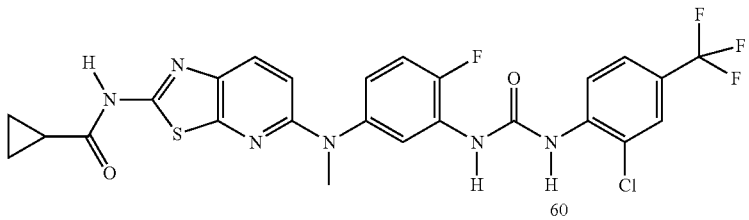

N-{5-[(3-Amino-4-fluorophenyl)(methyl)amino][1,3]thiazolo[5,4-b]pyridin-2-yl}cyclopropanecarboxamide (120 mg, 0.34 mmol) produced in Example 1(x) was dissolved in N,N-dimethylformamide (1.5 mL), 2-chloro-1-isocyanato-4-(trifluoromethyl)benzene (62 μL, 0.40 mmol) was added, and the mixture was stirred at room temperature 6 hr. The reaction mixture was diluted with ethyl acetate (10 mL), and washed successively with saturated aqueous sodium hydrogen carbonate solution (10 mL) and saturated brine (10 mL). The organic layer was dried over anhydrous sodium sulfate and concentrated under reduced pressure. The obtained residue was purified by basic silica gel column chromatography (ethyl acetate/hexane=50/50→100/0), and the obtained solution was concentrated under reduced pressure. The residue was recrystallized from ethyl acetate to give the title compound (125 mg, 64%) as a colorless powder.

$^1$H-NMR (DMSO-$d_6$, 300 MHz) δ 0.89-0.98 (4H, m), 1.86-2.06 (1H, m), 3.41 (3H, s), 6.60 (1H, d, J=9.0 Hz), 6.89-7.13 (1H, m), 7.36 (1H, dd, J=11.0, 8.8 Hz), 7.65 (1H, dd, J=8.9, 1.5 Hz), 7.76 (1H, d, J=9.0 Hz), 7.88 (1H, d, J=1.7 Hz), 8.15 (1H, dd, J=7.4, 2.6 Hz), 8.41 (1H, d, J=8.3 Hz), 9.15 (1H, s), 9.69 (1H, s), 12.46 (1H, s).

Example 7

Production of N-(5-{[4-fluoro-3-({[4-(trifluoromethoxy)phenyl]carbamoyl}amino)phenyl](methyl)amino}[1,3]thiazolo[5,4-b]pyridin-2-yl)cyclopropanecarboxamide

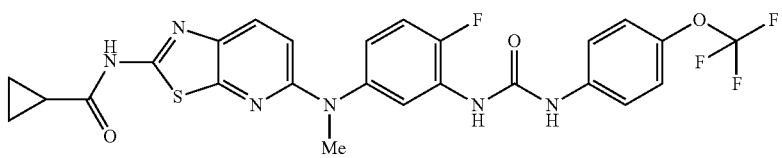 [SMILES: CN(c1ccc(F)c(NC(=O)Nc2ccc(OC(F)(F)F)cc2)c1)c1ccc2nc(NC(=O)C3CC3)sc2n1]

N-{5-[(3-Amino-4-fluorophenyl)(methyl)amino][1,3]thiazolo[5,4-b]pyridin-2-yl}cyclopropanecarboxamide (120 mg, 0.34 mmol) produced in Example 1(x) was dissolved in N,N-dimethylformamide (1.5 mL), 1-isocyanato-4-(trifluoromethoxy)benzene (70 μl, 0.46 mmol) was added, and the mixture was stirred at room temperature for 12 hr. 1-Isocyanato-4-(trifluoromethoxy)benzene (70 μL, 0.46 mmol) was further added to the reaction mixture, and the mixture was further stirred at 70° C. for 3 hr. Pyridine (1.5 mL) was added to the reaction mixture, and the mixture was further stirred at 70° C. for 2 hr. The reaction mixture was diluted with ethyl acetate (20 mL), and washed successively with saturated aqueous sodium hydrogen carbonate solution (20 mL) and saturated brine (10 mL). The organic layer was dried over anhydrous sodium sulfate and concentrated under reduced pressure. The obtained residue was purified by basic silica gel column chromatography (ethyl acetate/hexane=50/50→100/0), and the obtained solution was concentrated under reduced pressure. The residue was recrystallized from ethyl acetate to give the title compound (69 mg, 37%) as a colorless powder.

$^1$H-NMR (DMSO-$d_6$, 300 MHz) δ 0.88-1.04 (4H, m), 1.92-2.07 (1H, m), 3.40 (3H, s), 6.59 (1H, d, J=9.1 Hz), 6.92-7.04 (1H, m), 7.15-7.42 (3H, m), 7.48-7.59 (2H, m), 7.76 (1H, d, J=9.1 Hz), 8.13 (1H, dd, J=7.4, 2.5 Hz), 8.71 (1H, d, J=2.5 Hz), 9.29 (1H, s), 12.45 (1H, s).

Example 8

Production of N-{5-[(3-{[(4-tert-butylphenyl)carbamoyl]amino}phenyl)(methyl)amino][1,3]thiazolo[5,4-b]pyridin-2-yl}cyclopropanecarboxamide

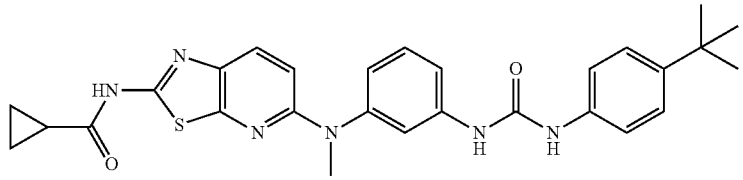 [SMILES: CN(c1cccc(NC(=O)Nc2ccc(C(C)(C)C)cc2)c1)c1ccc2nc(NC(=O)C3CC3)sc2n1]

(i) Production of tert-butyl (3-nitrophenyl)carbamate

To a solution of 3-nitroaniline (25.0 g, 0.181 mol) in tert-butanol (250 mL) was added di-tert-butyl bicarbonate (45.7 mL, 0.199 mol), and the mixture was stirred at 60° C. for 20 hr. The reaction mixture was concentrated under reduced pressure, and the precipitate was collected by filtration to give the title compound (38.6 g, 90%) as a pale-yellow powder.

$^1$H-NMR (CDCl$_3$, 300 MHz) δ 1.54 (9H, s), 6.67 (1H, br s), 7.44 (1H, t, J=8.2 Hz), 7.69 (1H, dd, J=8.2, 1.1 Hz), 7.88 (1H, ddd, J=8.2, 2.2, 1.1 Hz), 8.30 (1H, t, J=2.2 Hz).

(ii) Production of tert-butyl (3-nitrophenyl)methylcarbamate

To a solution of tert-butyl (3-nitrophenyl)carbamate (38.6 g, 0.162 mol) in N,N-dimethylformamide (386 ml) were added cesium carbonate (63.2 g, 0.194 mol) and methyl iodide (11.1 mL, 0.178 mol), and the mixture was stirred at room temperature for 3 hr. Cesium carbonate (5.30 g, 16.2 mmol) and methyl iodide (1.0 mL, 16.2 mmol) were further added to the reaction mixture, and the mixture was stirred at room temperature for 1 hr. The insoluble material was filtered off, and the filtrate was concentrated under reduced pressure. Ethyl acetate (600 mL) was added to the residue, and the mixture was washed successively with water (200 mL) and saturated brine (200 mL). The organic layer was dried over anhydrous magnesium sulfate and concentrated under reduced pressure to give the title compound (40.5 g, 99%) as a pale-yellow powder.

$^1$H-NMR (CDCl$_3$, 300 MHz) δ 1.49 (9H, s), 3.33 (3H, s), 7.49 (1H, t, J=8.1 Hz), 7.61-7.65 (1H, m), 8.01 (1H, ddd, J=8.1, 2.2, 1.1 Hz), 8.16 (1H, t, J=2.2 Hz).

(iii) Production of tert-butyl (3-aminophenyl)methylcarbamate

To a solution of tert-butyl (3-nitrophenyl)methylcarbamate (40.5 g, 0.161 mol) in ethanol (810 mL) was added 10% palladium-carbon (4.1 g), and the mixture was stirred at room temperature for 19 hr under a hydrogen atmosphere. The insoluble material was filtered off through celite, and the filtrate was concentrated under reduced pressure. The precipitate was collected by filtration to give the title compound (34.1 g, 96%) as a colorless powder.

$^1$H-NMR (CDCl$_3$, 300 MHz) δ 1.45 (9H, s), 3.22 (3H, s), 3.66 (2H, br s), 6.50 (1H, ddd, J=7.9, 2.3, 0.9 Hz), 6.56-6.66 (2H, m), 7.09 (1H, t, J=7.9 Hz).

(iv) Production of tert-butyl methyl{3-[(trifluoroacetyl)amino]phenyl}carbamate To a solution of tert-butyl (3-aminophenyl)methylcarbamate (34.1 g, 0.153 mol) in tetrahydrofuran (341 mL) was added trifluoroacetic anhydride (23.5 mL, 0.169 mol) at 0° C., and the mixture was stirred for 40 min. The reaction mixture was diluted with ethyl acetate (500 mL), and washed with aqueous sodium hydrogen carbonate solution (200 mL) and saturated brine (200 mL). The organic layer was dried over anhydrous magnesium sulfate and concentrated under reduced pressure, and the precipitate was collected by filtration to give the title compound (47.8 g, 98%) as a colorless powder.

$^1$H-NMR (CDCl$_3$, 300 MHz) δ 1.49 (9H, s), 3.27 (3H, s), 7.05-7.13 (1H, m), 7.28-7.36 (2H, m), 7.52-7.60 (1H, m), 8.15 (1H, br s).

(v) Production of 2,2,2-trifluoro-N-[3-(methylamino)phenyl]acetamide

To trifluoroacetic acid (144 mL) was added tert-butyl methyl{3-[(trifluoroacetyl)amino]phenyl}carbamate (47.8 g, 0.150 mol) at 0° C., and the mixture was stirred for 1 hr. The reaction mixture was concentrated under reduced pressure, ethyl acetate (500 ml) was added to the residue, and the mixture was washed successively with aqueous sodium hydrogen carbonate solution (200 ml) and saturated brine (200 mL). The organic layer was dried over anhydrous magnesium sulfate and concentrated under reduced pressure, and the precipitate was collected by filtration to give the title compound (29.2 g, 89%) as a pale-green powder.

$^1$H-NMR (DMSO-d$_6$, 300 MHz) δ 2.65 (3H, d, J=5.0 Hz), 5.82 (1H, q, J=5.0 Hz), 6.39 (1H, ddd, J=8.1, 2.3, 0.9 Hz), 6.79-6.91 (2H, m), 7.07 (1H, t, J=8.1 Hz), 10.96 (1H, br s).

(vi) Production of 2,2,2-trifluoro-N-{3-[methyl(5-nitropyridin-2-yl)amino]phenyl}acetamide To a solution of 2,2,2-trifluoro-N-[3-(methylamino)phenyl]acetamide (10.0 g, 45.8 mmol) in N,N-dimethylformamide (40 mL) was added 2-chloro-5-nitropyridine (7.99 g, 50.4 mmol), and the mixture was stirred at 120° C. for 23 hr. The reaction mixture was cooled to room temperature, aqueous sodium hydrogen carbonate solution (100 mL) was added, and the mixture was extracted with ethyl acetate (300 mL). The organic layer was washed with water (70 mL) and saturated brine (50 mL), and dried over anhydrous magnesium sulfate. The dried organic layer was purified by silica gel column chromatography (150 g, ethyl acetate) to give the title compound (15.0 g, 96%) as a yellow powder.

¹H-NMR (DMSO-d₆, 300 MHz) δ 3.52 (3H, s), 6.53 (1H, d, J=9.6 Hz), 7.26 (1H, ddd, J=8.6, 1.3, 1.1 Hz), 7.56 (1H, t, J=8.6 Hz), 7.62-7.78 (2H, m), 8.19 (1H, dd, J=9.6, 2.5 Hz), 9.05 (1H, d, J=2.5 Hz), 11.44 (1H, br s).

(vii) Production of N-{3-[(5-aminopyridin-2-yl)(methyl)amino]phenyl}-2,2,2-trifluoroacetamide 2,2,2-Trifluoro-N-{3-[methyl(5-nitropyridin-2-yl)amino]phenyl}acetamide (5.00 g, 14.7 mmol) was dissolved in ethanol (66 mL)/tetrahydrofuran (33 mL), 10% palladium-carbon (500 mg) was added, and the mixture was stirred at room temperature for 3 hr under a hydrogen atmosphere. The insoluble material was filtered off through celite, and the filtrate was concentrated under reduced pressure. The precipitate was collected by filtration to give the title compound (3.60 g, 79%) as a pale-violet powder.
¹H-NMR (DMSO-d₆, 300 MHz) δ 3.24 (3H, s), 5.01 (2H, s), 6.71-6.84 (2H, m), 6.94 (1H, dd, J=8.7, 2.9 Hz), 7.15-7.29 (3H, m), 7.73 (1H, d, J=2.3 Hz), 11.07 (1H, br s).

(viii) Production of N-{3-[(2-amino[1,3]thiazolo[5,4-b]pyridin-5-yl)(methyl)amino]phenyl}-2,2,2-trifluoroacetamide To a solution of potassium thiocyanate (4.31 g, 44.4 mmol) in acetic acid (15 ml) was added a solution of N-[3-[(5-aminopyridin-2-yl)(methyl)amino]phenyl]-2,2,2-trifluoroacetamide (3.46 g, 11.1 mmol) in acetic acid (10 mL), and the mixture was stirred at room temperature for 20 min. To this solution was added dropwise a solution of bromine (1.95 g, 12.2 mmol) in acetic acid (10 mL), and the mixture was stirred at room temperature for 16 hr. The reaction mixture was filtered through celite, and the filtrate was concentrated under reduced pressure. The residue was dissolved in ethyl acetate (140 mL)/tetrahydrofuran (70 mL), and washed with aqueous sodium hydrogen carbonate solution (70 mL) and saturated brine (50 mL). The organic layer was dried over anhydrous sodium sulfate and concentrated under reduced pressure, and the residue was purified by silica gel column chromatography (hexane/ethyl acetate=80/20→0/100) to give the title compound (829 mg, 20%) as a violet powder.
¹H-NMR (DMSO-d₆, 300 MHz) δ 3.38 (3H, s), 6.68 (1H, d, J=8.7 Hz), 7.07 (1H, dt, J=7.7, 1.8 Hz), 7.32-7.61 (6H, m), 11.21 (1H, br s).

(ix) Production of N-[5-(methyl{3-[(trifluoroacetyl)amino]phenyl}amino)[1,3]thiazolo[5,4-b]pyridin-2-yl]cyclopropanecarboxamide To a solution of N-{3-[(2-amino[1,3]thiazolo[5,4-b]pyridin-5-yl)(methyl)amino]phenyl}-2,2,2-trifluoroacetamide (174 mg, 0.474 mmol) in pyridine (1.7 mL) was added cyclopropanecarbonyl chloride (55 μL, 0.610 mmol) at −20° C., and the mixture was stirred for 2 hr. The reaction mixture was diluted with ethyl acetate (50 mL), washed with water (20 mL) and saturated brine (20 mL), dried over anhydrous sodium sulfate, and concentrated under reduced pressure. The residue was purified by basic silica gel column chromatography (hexane/ethyl acetate=80/20→0/100) to give the title compound (147 mg, 71%) as a pale-violet powder.
¹H-NMR (DMSO-d₆, 300 MHz) δ 0.85-1.04 (4H, m), 1.91-2.04 (1H, m), 3.44 (3H, s), 6.73 (1H, d, J=9.0 Hz), 7.18 (1H, dd, J=7.4, 1.5 Hz), 7.36-7.70 (3H, m), 7.80 (1H, d, J=9.0 Hz), 11.29 (1H, br s), 12.45 (1H, br s).

(x) Production of N-{5-[(3-aminophenyl)(methyl)amino][1,3]thiazolo[5,4-b]pyridin-2-yl}cyclopropanecarboxamide N-[5-(Methyl{3-[(trifluoroacetyl)amino]phenyl}amino)[1,3]thiazolo[5,4-b]pyridin-2-yl]cyclopropanecarboxamide (748 mg, 1.72 mmol) was dissolved in tetrahydrofuran (22.5 mL)/methanol (7.5 mL), 2N aqueous sodium hydroxide solution (7.5 mL) was added, and the mixture was stirred at room temperature for 19 hr. Aqueous ammonium chloride solution (20 mL) was added to the reaction mixture, and the mixture was extracted with ethyl acetate (50 mL). The organic layer was washed with saturated brine (20 mL), dried over anhydrous sodium sulfate, and concentrated under reduced pressure. The residue was purified by silica gel column chromatography (hexane/ethyl acetate=80/20→0/100) to give the title compound (542 mg, 93%) as a colorless powder.
¹H-NMR (DMSO-d₆, 300 MHz) δ 0.92-0.94 (4H, m), 1.90-1.98 (1H, m), 3.35 (3H, s), 5.21 (2H, br s), 6.35-6.52 (3H, m), 6.58 (1H, d, J=9.1 Hz), 7.08 (1H, t, J=8.1 Hz), 7.71 (1H, d, J=9.1 Hz), 12.42 (1H, br s).

(xi) Production of N-{5-[(3-{([(4-tert-butylphenyl)carbamoyl]amino}phenyl)(methyl)amino][1,3]thiazolo[5,4-b]pyridin-2-yl}cyclopropanecarboxamide To a solution of N-{5-[(3-aminophenyl)(methyl)amino][1,3]thiazolo[5,4-b]pyridin-2-yl}cyclopropanecarboxamide (100 mg, 0.295 mmol) in N,N-dimethylformamide (1.0 mL) was added 1-tert-butyl-4-isocyanatobenzene (62.9 μL, 0.354 mmol), and the mixture was stirred at room temperature for 1 hr. Aqueous sodium hydrogen carbonate solution (20 mL) was added to the reaction mixture, and the mixture was extracted with ethyl acetate (50 mL). The organic layer was washed with saturated brine (20 mL), dried over anhydrous sodium sulfate, and concentrated under reduced pressure. The precipitate was collected by filtration, and recrystallized from hexane/tetrahydrofuran to give the title compound (89.0 mg, 56%) as a colorless powder.
¹H-NMR (DMSO-d₆, 300 MHz) δ 0.87-1.00 (4H, m), 1.25 (9H, s), 1.92-2.03 (1H, m), 3.42 (3H, s), 6.66 (1H, d, J=9.1 Hz), 6.86-6.97 (1H, m), 7.18-7.41 (6H, m), 7.51 (1H, t, J=2.0 Hz), 7.76 (1H, d, J=9.1 Hz), 8.58 (1H, s), 8.72 (1H, s), 12.45 (1H, s).

Example 9

Production of N-(5-{methyl[3-({[4-(trifluoromethoxy)phenyl]carbamoyl}amino)phenyl]amino}[1,3]thiazolo[5,4-b]pyridin-2-yl)cyclopropanecarboxamide

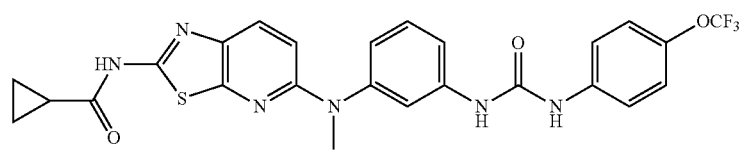 [SMILES: CN(c1cccc(NC(=O)Nc2ccc(OC(F)(F)F)cc2)c1)c1ccc2nc(NC(=O)C3CC3)sc2n1]

To a solution of N-{5-[(3-aminophenyl)(methyl)amino][1,3]thiazolo[5,4-b]pyridin-2-yl}cyclopropanecarboxamide (100 mg, 0.295 mmol) produced in Example 8(x) in N,N-dimethylformamide (1.0 mL) was added 1-isocyanato-4-(trifluoromethoxy)benzene (53 μL, 0.354 mmol), and the mixture was stirred at room temperature for 1 hr. Aqueous sodium hydrogen carbonate solution (20 mL) was added to the reaction mixture, and the mixture was extracted with ethyl acetate (50 mL). The organic layer was washed with saturated brine (20 mL), dried over anhydrous sodium sulfate, and concentrated under reduced pressure. The precipitate was collected by filtration, and recrystallized from hexane/tetrahydrofuran to give the title compound (101 mg, 63%) as a colorless powder.

$^1$H-NMR (DMSO-$d_6$, 300 MHz) δ 0.85-1.00 (4H, m), 1.89-2.04 (1H, m), 3.42 (3H, s), 6.67 (1H, d, J=9.0 Hz), 6.86-7.00 (1H, m), 7.20-7.42 (4H, m), 7.46-7.61 (3H, m), 7.75 (1H, d, J=9.0 Hz), 8.96 (1H, br s), 9.04 (1H, br s), 12.45 (1H, br s).

Example 10

Production of N-(5-{methyl[3-({[4-(trifluoromethyl)phenyl]carbamoyl}amino)phenyl]amino}[1,3]thiazolo[5,4-b]pyridin-2-yl)cyclopropanecarboxamide

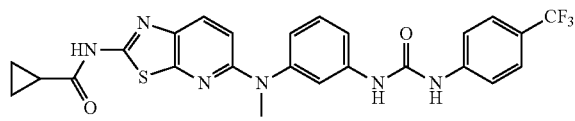 [SMILES: CN(c1cccc(NC(=O)Nc2ccc(C(F)(F)F)cc2)c1)c1ccc2nc(NC(=O)C3CC3)sc2n1]

To a solution of N-{5-[(3-aminophenyl)(methyl)amino][1,3]thiazolo[5,4-b]pyridin-2-yl}cyclopropanecarboxamide (100 mg, 0.295 mmol) produced in Example 8(x) in N,N-dimethylformamide (1.0 mL) was added 1-isocyanato-4-(trifluoromethyl)benzene (50.5 μL, 0.354 mmol), and the mixture was stirred at room temperature for 1 hr. Aqueous sodium hydrogen carbonate solution (20 mL) was added to the reaction mixture, and the mixture was extracted with ethyl acetate (50 mL). The organic layer was washed with saturated brine (20 mL), dried over anhydrous sodium sulfate, and concentrated under reduced pressure. The precipitate was collected by filtration and recrystallized from hexane/tetrahydrofuran to give the title compound (98 mg, 63%) as a colorless powder.

$^1$H-NMR (DMSO-$d_6$, 300 MHz) δ 0.84-1.00 (4H, m), 1.89-2.04 (1H, m), 3.43 (3H, s), 6.68 (1H, d, J=9.0 Hz), 6.88-7.01 (1H, m), 7.22-7.42 (2H, m), 7.53 (1H, t, J=2.0 Hz), 7.56-7.70 (4H, m), 7.76 (1H, d, J=9.0 Hz), 9.12 (1H, br s), 9.33 (1H, br s), 12.44 (1H, br s).

Example 11

Production of N-(5-{[3-({[4-chloro-3-(trifluoromethyl)phenyl]carbamoyl}amino)phenyl](methyl)amino}[1,3]thiazolo[5,4-b]pyridin-2-yl)cyclopropanecarboxamide

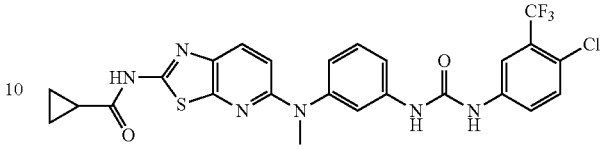

To a solution of N-{5-[(3-aminophenyl)(methyl)amino][1,3]thiazolo[5,4-b]pyridin-2-yl}cyclopropanecarboxamide (100 mg, 0.295 mmol) produced in Example 8(x) in N,N-dimethylformamide (1.0 mL) was added 1-chloro-4-isocyanato-2-(trifluoromethyl)benzene (78.4 mg, 0.354 mmol), and the mixture was stirred at room temperature for 1 hr. Aqueous sodium hydrogen carbonate solution (20 mL) was added to the reaction mixture, and the mixture was extracted with ethyl acetate (50 mL). The organic layer was washed with saturated brine (20 mL), dried over anhydrous sodium sulfate, and concentrated under reduced pressure. The precipitate was collected by filtration and recrystallized from hexane/tetrahydrofuran to give the title compound (118 mg, 72%) as a colorless powder.

$^1$H-NMR (DMSO-$d_6$, 300 MHz) δ 0.85-1.02 (4H, m), 1.92-2.04 (1H, m), 3.43 (3H, s), 6.67 (1H, d, J=9.0 Hz), 6.90-7.01 (1H, m), 7.23-7.42 (2H, m), 7.51 (1H, t, J=2.0 Hz), 7.55-7.69 (2H, m), 7.76 (1H, d, J=9.0 Hz), 8.07 (1H, d, J=2.3 Hz), 8.95 (1H, s), 9.17 (1H, s), 12.45 (1H, s).

Example 12

Production of N-(5-{[4-fluoro-3-({[4-(trifluoromethoxy)phenyl]carbamoyl}amino)phenyl]amino}[1,3]thiazolo[5,4-b]pyridin-2-yl)cyclopropanecarboxamide

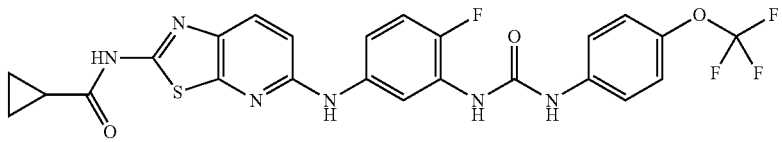 [SMILES: O=C(Nc1ccc(OC(F)(F)F)cc1)Nc1cc(Nc2ccc3nc(NC(=O)C4CC4)sc3n2)ccc1F]

(i) Production of di-tert-butyl (2-fluoro-5-nitrophenyl)imidodicarbonate

To a solution of 2-fluoro-5-nitroaniline (15.6 g, 100 mmol) in dichloromethane (200 mL) were added di-tert-butyl bicarbonate (87.2 g, 400 mmol) and triethylamine (20.4 g, 200 mmol), and the mixture was stirred at 55° C. overnight. The reaction mixture was concentrated under reduced pressure, and the residue was purified by silica gel column chromatography (petroleum ether/ethyl acetate=10/1) to give the title compound (19.3 g, 54%) as a yellow powder.

$^1$H-NMR (CDCl$_3$, 300 MHz) δ 1.44 (18H, s), 8.12-8.16 (1H, m), 8.21-8.25 (2H, m).

(ii) Production of di-tert-butyl (5-amino-2-fluorophenyl)imidodicarbonate

To a solution of di-tert-butyl (2-fluoro-5-nitrophenyl)imidodicarbonate (256 mg, 0.718 mmol) in methanol (10 mL) was added 10% palladium-carbon (50 mg), and the mixture was stirred at room temperature overnight under a hydrogen atmosphere. The insoluble material was filtered off through celite, and the filtrate was concentrated under reduced pressure to give the title compound (150 mg, 64%).

$^1$H-NMR (CDCl$_3$, 300 MHz) δ 1.42 (18H, s), 3.55 (2H, br s), 6.46-6.54 (1H, m), 6.55-6.59 (1H, m), 6.85-6.92 (1H, m).

(iii) Production of 5-chloro[1,3]thiazolo[5,4-b]pyridin-2-amine

Potassium thiocyanate (16.0 g, 165 mmol) and 6-chloropyridin-3-amine (2.6 g, 20.2 mmol) were dissolved in acetic acid (52 mL). To this solution was added dropwise a solution of bromine (3.2 mL, 62.5 mmol) in acetic acid (12 mL) under cooling in a water bath, and the mixture was stirred for 2 hr. The mixture was warmed to, stirred for 10 hr, and water (30 mL) was added. This reaction mixture was filtered at 85° C., and the insoluble material was suspended in acetic acid (50 mL) and the suspension was filtered. The obtained filtrate was neutralized with aqueous ammonia solution, and the precipitated solid was collected by filtration and recrystallized from methanol to give the title compound (2.0 g, 54%) as a colorless powder.

$^1$H-NMR (DMSO-d$_6$, 300 MHz) δ 7.31 (1H, d, J=8.4 Hz), 7.65 (1H, d, J=8.4 Hz), 7.93 (2H, br s).

(iv) Production of tert-butyl [5-({2-[(cyclopropylcarbonyl)amino][1,3]thiazolo[5,4-b]pyridin-5-yl}amino)-2-fluorophenyl]carbamate To a solution of cyclopropanecarboxylic acid (129 mg, 1.50 mmol) in dichloromethane (5 ml) were added oxalyl chloride (190 mg, 1.50 mmol) and N,N-dimethylformamide (40 μL), and the mixture was stirred at room temperature for 1 hr. This is reaction mixture was added to a solution of 5-chloro[1,3]thiazolo[5,4-b]pyridin-2-amine (185 mg, 1.00 mmol) in tetrahydrofuran (10 mL) at 0° C., and the mixture was stirred for 2 hr. Water (10 mL) was added to the reaction mixture, and the mixture was extracted with ethyl acetate (30 mL×3). The organic layer was concentrated under reduced pressure to give N-(5-chloro[1,3]thiazolo[5,4-b]pyridin-2-yl)cyclopropanecarboxamide.

$^1$H-NMR (CDCl$_3$, 300 MHz) δ 1.02-1.06 (2H, m), 1.23-1.30 (2H, m), 1.51-1.69 (1H, m), 7.38 (1H, d, J=8.7 Hz), 7.92 (1H, d, J=8.7 Hz), 9.93 (1H, br s).

To a mixture of N-(5-chloro[1,3]thiazolo[5,4-b]pyridin-2-yl)cyclopropanecarboxamide (76 mg, 0.300 mmol) produced above, di-tert-butyl (5-amino-2-fluorophenyl) imidodicarbonate (98 mg, 0.300 mmol), tris(dibenzylideneacetone)dipalladium (57 mg, 60.0 μmol), dicyclohexyl(2',4',6'-triisopropylbiphenyl-2-yl)phosphine (X-phos) (15 mg, 30.0 μmol) and potassium tert-butoxide (145 mg, 1.40 mmol) waa added tert-butanol (20 mL) under a nitrogen atmosphere, and the mixture was stirred at 90° C. for 35 min under microwave irradiation. Water (5 mL) was added to the reaction mixture, and the mixture was extracted with ethyl acetate (50 mL×3). The organic layer was dried over anhydrous sodium sulfate and concentrated under reduced pressure. The residue was purified by silica gel column chromatography (petroleum ether/ethyl acetate=1/1) to give the title compound (84 mg, 63%) as a brown powder.

$^1$H-NMR (CDCl$_3$, 300 MHz) δ 0.93-1.00 (2H, m), 1.25-1.28 (2H, m), 1.50 (9H, s), 1.54-1.69 (1H, m), 6.80-6.85 (3H, m), 6.97-7.05 (1H, m), 7.16-7.22 (1H, m), 7.77 (1H, d, J=8.7 Hz), 8.02 (1H, dd, J=7.2, 2.4 Hz), 11.56 (1H, br s).

(v) Production of N-{5-[(3-amino-4-fluorophenyl)amino][1,3]thiazolo[5,4-b]pyridin-2-yl}cyclopropanecarboxamide To tert-butyl [5-({2-[(cyclopropylcarbonyl)amino][1,3]thiazolo[5,4-b]pyridin-5-yl}amino)-2-fluorophenyl]carbamate (3.40 g, 7.67 mmol) was added 4N hydrogen chloride/ethyl acetate (50 mL), and the mixture was stirred at 0° C. overnight. The reaction mixture was neutralized with saturated aqueous sodium hydrogen carbonate solution, and the mixture was extracted with ethyl acetate (50 mL×3). The organic layer was concentrated under reduced pressure to give the title compound (1.70 g, 65%) as a violet powder.

$^1$H-NMR (DMSO-d$_6$, 300 MHz) δ 0.92-0.97 (4H, m), 1.96-2.00 (1H, m), 5.08 (2H, br s), 6.73-6.78 (1H, m), 6.85-6.92 (2H, m), 7.16 (1H, dd, J=8.4, 2.4 Hz), 7.84 (1H, d, J=9.0 Hz), 8.97 (1H, s), 12.41 (1H, s).

(vi) Production of N-(5-{[4-fluoro-3-({[4-(trifluoromethoxy)phenyl]carbamoyl}amino)phenyl]amino}[1,3]thiazolo[5,4-b]pyridin-2-yl)cyclopropanecarboxamide N-{5-[(3-Amino-4-fluorophenyl)amino][1,3]thiazolo[5,4-b]pyridin-2-yl}cyclopropanecarboxamide (200 mg, 0.58 mmol) was dissolved in pyridine (3.0 mL), 1-isocyanato-4-(trifluoromethoxy)benzene (132 μL, 0.88 mmol) was added, and the mixture was stirred at 70° C. for 8 hr. The reaction mixture was cooled to room temperature, diluted with ethyl acetate (10 mL) and washed successively with water (10 mL) and saturated brine (10 mL). The organic layer was dried over anhydrous sodium sulfate and concentrated under reduced pressure. The obtained residue was purified by basic silica gel column chromatography (ethyl acetate/hexane=5/95→50/50), and the obtained solution was concentrated under reduced pressure. The residue was recrystallized from ethyl acetate to give the title compound (145 mg, 45%) as a colorless powder.

$^1$H-NMR (DMSO-d$_6$, 300 MHz) δ 0.93 (4H, d, J=5.5 Hz), 1.85-2.10 (1H, m), 6.93 (1H, d, J=9.0 Hz), 7.17 (1H, dd, J=11.0, 9.0 Hz), 7.31 (2H, d, J=8.6 Hz), 7.48-7.69 (3H, m), 7.88 (1H, d, J=9.0 Hz), 8.28 (1H, dd, J=7.4, 2.6 Hz), 8.55 (1H, d, J=2.6 Hz), 9.31 (2H, d, J=8.6 Hz), 12.45 (1H, br s).

Example 13

Production of N-(5-{[3-({[4-chloro-3-(trifluoromethyl)phenyl]carbamoyl}amino)-4-fluorophenyl]amino}[1,3]thiazolo[5,4-b]pyridin-2-yl)cyclopropanecarboxamide

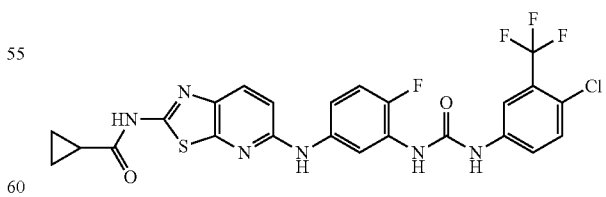

N-{5-[(3-Amino-4-fluorophenyl)amino][1,3]thiazolo[5,4-b]pyridin-2-yl}cyclopropanecarboxamide (200 mg, 0.58 mmol) produced in Example 12(v) was dissolved in pyridine (3.0 mL), 1-chloro-4-isocyanato-2-(trifluoromethyl)benzene (190 mg, 0.88 mmol) was added, and the mixture was stirred at 70° C. for 8 hr. The reaction mixture was cooled to room temperature, diluted with ethyl acetate (10 mL), and washed successively with water (10 mL) and saturated brine (10 ml). The organic layer was dried over anhydrous sodium sulfate and concentrated under reduced pressure. The obtained residue was purified by basic silica gel column chromatography (ethyl acetate/hexane=10/90→80/20), and the obtained solution was concentrated under reduced pressure. The residue was recrystallized from ethyl acetate to give the title compound (130 mg, 39%) as a colorless powder.

$^1$H-NMR (DMSO-$d_6$, 300 MHz) δ 0.78-1.06 (4H, m), 1.84-2.09 (1H, m), 6.93 (1H, d, J=9.0 Hz), 7.19 (1H, dd, J=11.0, 9.0 Hz), 7.46-7.77 (3H, m), 7.89 (1H, d, J=9.0 Hz), 8.09-8.38 (2H, m), 8.65 (1H, d, J=2.4 Hz), 9.35 (1H, s), 9.54 (1H, s), 12.46 (1H, s).

Example 14

Production of N-(5-{[4-fluoro-3-({[4-(trifluoromethyl)phenyl]carbamoyl}amino)phenyl]amino}[1,3]thiazolo[5,4-b]pyridin-2-yl)cyclopropanecarboxamide

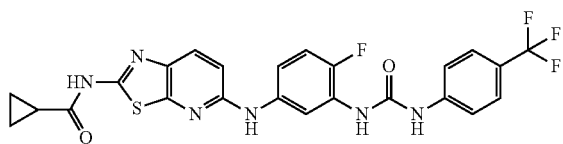 [SMILES: O=C(Nc1ccc(C(F)(F)F)cc1)Nc1cc(Nc2ccc3nc(NC(=O)C4CC4)sc3n2)ccc1F]

N-{5-[(3-Amino-4-fluorophenyl)amino][1,3]thiazolo[5,4-b]pyridin-2-yl}cyclopropanecarboxamide (100 mg, 0.30 mmol) produced in Example 12(v) was dissolved in tetrahydrofuran (10 ml), 1-isocyanato-4-(trifluoromethyl)benzene (84 mg, 0.45 mmol) was added, and the mixture was stirred at room temperature for 1 hr. The reaction mixture was concentrated under reduced pressure, and the residue was purified by silica gel column chromatography (petroleum ether/ethyl acetate=10/1) to give the title compound (47 mg, 30%) as a yellow-brown powder.

$^1$H-NMR (DMSO-$d_6$, 300 MHz) δ 0.93-0.95 (4H, m), 1.94-2.00 (1H, m), 6.93 (1H, d, J=9.0 Hz), 7.15-7.22 (1H, m), 7.59-7.64 (1H, m), 7.66 (4H, s), 7.88 (1H, d, J=9.0 Hz), 8.29 (1H, dd, J=7.5, 3.0 Hz), 8.62 (1H, br s), 9.33 (1H, s), 9.48 (1H, s), 12.45 (1H, s).

Example 15

Production of N-{5-[4-chloro-3-({[4-chloro-3-(trifluoromethyl)phenyl]carbamoyl}amino)phenoxy][1,3]thiazolo[5,4-b]pyridin-2-yl}cyclopropanecarboxamide

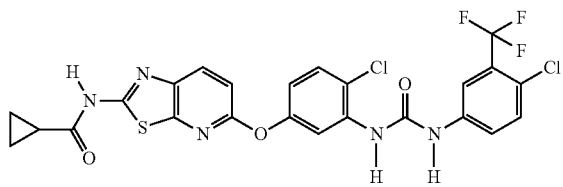 [SMILES: O=C(Nc1ccc(Cl)c(C(F)(F)F)c1)Nc1cc(Oc2ccc3nc(NC(=O)C4CC4)sc3n2)ccc1Cl]

(i) Production of 2-chloro-5-[(5-nitropyridin-2-yl)oxy]aniline

To a solution of 2-chloro-5-nitropyridine (4.76 g, 30 mmol) and 3-amino-4-chlorophenol (4.31 g, 30 mmol) in N,N-dimethylformamide (15 mL) was added potassium carbonate (4.15 g, 30 mmol), and the mixture was stirred at room temperature for 16 hr. Ethyl acetate (80 mL) was added to the reaction mixture, and the mixture was washed successively with water (50 mL) and saturated brine (50 mL). The organic layer was dried over anhydrous magnesium sulfate and concentrated under reduced pressure. The residual solid was recrystallized from ethyl acetate (15 mL)/n-hexane (15 mL), and the precipitated crystals were collected by filtration, washed with diisopropyl ether (20 mL) and dried under reduced pressure to give the title compound (6.74 g, 85%) as brownish-red crystals.

$^1$H-NMR (CDCl$_3$, 300 MHz) δ 4.19 (2H, br s), 6.48 (1H, dd, J=8.6, 2.7 Hz), 6.58 (1H, d, J=2.7 Hz), 7.01 (1H, d, J=9.0 Hz), 7.29 (1H, d, J=8.6 Hz), 8.47 (1H, dd, J=9.0, 2.7 Hz), 9.05 (1H, d, J=2.7 Hz).

(ii) Production of N-{2-chloro-5-[(5-nitropyridin-2-yl)oxy]phenyl}-2,2,2-trifluoroacetamide 2-Chloro-5-[(5-nitropyridin-2-yl)oxy]aniline (6.5 g, 24.5 mmol) was dissolved in tetrahydrofuran (50 mL), trifluoroacetic acid anhydride (3.73 mL, 26.9 mmol) was added, and the mixture was stirred at room temperature for 1 hr. The reaction mixture was concentrated under reduced pressure, and the residue was dissolved in ethyl acetate (80 mL), and washed with aqueous sodium hydrogen carbonate solution (50 mL). The organic layer was dried over anhydrous magnesium sulfate, and concentrated under reduced pressure. The residual solid was collected by filtration with diisopropyl ether (30 mL), and dried to give the title compound (7.73 g, 87%) as a colorless is powder.

$^1$H-NMR (CDCl$_3$, 300 MHz) δ 6.95-7.19 (2H, m), 7.52 (1H, dd, J=9.0, 1.5 Hz), 8.20-8.30 (1H, m), 8.40-8.60 (2H, m), 9.00-9.10 (1H, m).

(iii) Production of N-{5-[(5-aminopyridin-2-yl)oxy]-2-chlorophenyl}-2,2,2-trifluoroacetamide N-{2-Chloro-5-[(5-nitropyridin-2-yl)oxy]phenyl}-2,2,2-trifluoroacetamide (13 g, 35.9 mmol) was dissolved in acetic acid (200 mL), reduced iron (10 g, 179 mmol) was added, and the mixture was stirred at 60° C. for 3 hr. After cooling to room temperature, the reaction mixture was concentrated under reduced pressure. The concentrate was diluted with ethyl acetate (150 mL), aqueous sodium hydrogen carbonate solution (200 mL) was gradually added, and the mixture was filtered through celite. The organic layer was separated, dried over anhydrous magnesium sulfate and concentrated under reduced pressure. The residual oily substance was dissolved in toluene, and purified by silica gel column chromatography (ethyl acetate/hexane=20/80→80/20) to give the title compound (10.9 g, 91%) as a brownish-red oil.

$^1$H-NMR (CDCl$_3$, 300 MHz) δ 3.57 (2H, br s), 6.83 (1H, d, J=8.7 Hz), 6.93 (1H, dd, J=8.7, 2.8 Hz), 7.11 (1H, dd, J=8.7, 2.8 Hz), 7.39 (1H, d, J=8.7 Hz), 7.69 (1H, d, J=3.0 Hz), 8.11 (1H, d, J=3.0 Hz), 8.41 (1H, br s).

(iv) Production of N-{5-[(2-amino[1,3]thiazolo[5,4-b]pyridin-5-yl)oxy]-2-chlorophenyl}-2,2,2-trifluoroacetamide N-{5-[(5-Aminopyridin-2-yl)oxy]-2-chlorophenyl}-2,2,2-trifluoroacetamide (12 g, 36.2 mmol) and potassium thiocyanate (14.1 g, 145 mmol) were suspended in acetic acid (145 mL), bromine (8.67 g, 54.3 mmol) was added dropwise under ice-cooling, and the reaction mixture was stirred at room temperature for 16 hr. The reaction mixture was filtered through celite, and the filtrate was concentrated under reduced pressure. The residual oily substance was dissolved in ethyl acetate (100 mL), and aqueous sodium hydrogen carbonate solution (150 mL) was gradually added to partition the solution. The organic layer was dried over anhydrous magnesium sulfate and concentrated under reduced pressure. The residual solid was collected by filtration with diisopropyl ether (100 mL), and dried to give the title compound (10.1 g, 72%) as a pale-yellow solid.

$^1$H-NMR (DMSO-$d_5$, 300 MHz) δ 6.98 (1H, d, J=8.5 Hz), 7.16 (1H, dd, J=8.8, 2.8 Hz), 7.27 (1H, d, J=2.8 Hz), 7.61 (1H, d, J=8.8 Hz), 7.66 (2H, br s), 7.75 (1H, d, J=8.5 Hz), 11.30 (1H, br s).

(v) Production of N-(5-{4-chloro-3-[(trifluoroacetyl)amino]phenoxy}[1,3]thiazolo[5,4-b]pyridin-2-yl)cyclopropanecarboxamide N-{5-[(2-Amino[1,3]thiazolo[5,4-b]pyridin-5-yl)oxy]-2-chlorophenyl}-2,2,2-trifluoroacetamide (5.0 g, 12.9 mmol) was dissolved in pyridine (25 mL), cyclopropanecarbonyl chloride (1.28 ml, 14.2 mmol) was added dropwise under ice-cooling, and the mixture was stirred at room temperature for 1 hr. The reaction mixture was treated with aqueous sodium hydrogen carbonate solution (100 mL), and diluted with ethyl acetate (100 mL). The organic layer was separated, dried over anhydrous magnesium sulfate and concentrated under reduced pressure. The residual solid was crystallized from ethyl acetate (30 mL), collected by filtration, and dried to give the title compound (3.46 g, 59%) as a colorless powder.

$^1$H-NMR (DMSO-$d_6$, 300 MHz) δ 0.86-1.07 (4H, m), 1.90-2.10 (1H, m), 7.20 (1H, d, J=8.7 Hz), 7.26 (1H, dd, J=8.9, 2.7 Hz), 7.38 (1H, d, J=2.7 Hz), 7.66 (1H, d, J=8.9 Hz), 8.20 (1H, d, J=8.7 Hz), 11.34 (1H, br s), 12.72 (1H, br s).

(vi) Production of N-[5-(3-amino-4-chlorophenoxy)[1,3]thiazolo[5,4-b]pyridin-2-yl]cyclopropanecarboxamide Sodium borohydride (5.63 g, 149 mmol) was suspended in ethanol (100 mL), and methanol (66 mL) was gradually added. While cooling in a water bath, to the obtained reaction mixture was added N-(5-{4-chloro-3-[(trifluoroacetyl)amino]phenoxy}[1,3]thiazolo[5,4-b]pyridin-2-yl)cyclopropanecarboxamide (3.4 g, 7.44 mmol) powder by small portions, and thereafter the mixture was stirred at room temperature, for 1 hr. The reaction mixture was diluted with ethyl acetate (150 mL), and partitioned with water (200 mL). The organic layer was concentrated under reduced pressure. The residue was diluted with ethyl acetate (200 mL), and washed with saturated brine (100 mL). The organic layer was dried over anhydrous magnesium sulfate and concentrated under reduced pressure. The residue was purified by basic silica gel column chromatography (ethyl acetate/methanol=100/0), and triturated with diisopropyl ether to give the title compound (2.00 g, 75%) as a colorless powder.

$^1$H-NMR (DMSO-$d_6$, 300 MHz) δ 0.88-1.10 (4H, m), 1.90-2.10 (1H, m), 5.49 (2H, br s), 6.32 (1H, dd, J=8.6, 2.7 Hz), 6.54 (1H, d, J=2.7 Hz), 7.08 (1H, d, J=8.6 Hz), 7.21 (1H, d, J=8.6 Hz), 8.15 (1H, d, J=8.6 Hz), 12.69 (1H, br s).

(vii) Production of N-{5-[4-chloro-3-({[4-chloro-3-(trifluoromethyl)phenyl]carbamoyl}amino)phenoxy][1,3]thiazolo[5,4-b]pyridin-2-yl}cyclopropanecarboxamide N-[5-(3-Amino-4-chlorophenoxy)[1,3]thiazolo[5,4-b]pyridin-2-yl]cyclopropanecarboxamide (120 mg, 0.33 mmol) was dissolved in N,N-dimethylformamide (2.0 ml), 1-chloro-4-isocyanato-2-(trifluoromethyl)benzene (89 mg, 0.40 mmol) was added, and the mixture was stirred at room temperature for 10 hr. The reaction mixture was diluted with ethyl acetate (10 mL), and washed with saturated brine (10 mL). The organic layer was dried over anhydrous sodium sulfate and concentrated under reduced pressure. The obtained residue was purified by basic silica gel column chromatography (ethyl acetate/hexane=50/50→100/0), and the obtained solution was concentrated under reduced pressure. The residue was recrystallized from ethyl acetate to give the title compound (63 mg, 33%) as a colorless powder.

$^1$H-NMR (DMSO-$d_6$, 300 MHz) δ 0.85-1.04 (4H, m), 1.99 (1H, s), 6.90 (1H, dd, J=8.7, 2.8 Hz), 7.16 (1H, d, J=8.7 Hz), 7.53 (1H, d, J=8.7 Hz), 7.58-7.66 (2H, m), 7.95-8.10 (2H, m), 8.18 (1H, d, J=8.7 Hz), 8.50 (1H, s), 9.93 (1H, s), 12.70 (1H, br s).

Example 16

Production of N-{5-[4-fluoro-3-({[4-(trifluoromethoxy)phenyl]carbamoyl}amino)phenoxy][1,3]thiazolo[5,4-b]pyridin-2-yl}cyclopropanecarboxamide

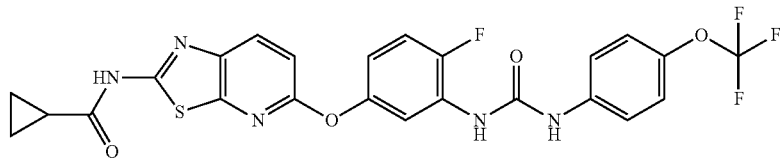 [SMILES: O=C(Nc1ccc(OC(F)(F)F)cc1)Nc1cc(Oc2ccc3nc(NC(=O)C4CC4)sc3n2)ccc1F]

(i) Production of 2-fluoro-5-[(5-nitropyridin-2-yl)oxy]aniline

A mixture of 2-chloro-5-nitropyridine (6.34 g, 40 mmol), 3-amino-4-fluorophenol (5.08 g, 40 mmol), potassium carbonate (5.52 g, 40 mmol) and N,N-dimethylformamide (20 mL) was stirred at room temperature overnight. The reaction mixture was poured into water (200 mL), and the Mixture was extracted with ethyl acetate (100 mL×2). The ethyl acetate layers were combined and dried over anhydrous sodium sulfate. The insoluble material was filtered off, and the filtrate was to concentrated under reduced pressure. The obtained residue was purified by silica gel column chromatography (ethyl acetate/hexane=0/100→50/50), and crystallized from diethyl ether to give the title compound (7.90 g, 79%) as a yellow powder.

$^1$H-NMR (DMSO-d$_6$, 300 MHz) δ 3.88 (2H, br s), 6.43-6.48 (1H, m), 6.57 (1H, dd, J=9.0, 2.7 Hz), 6.99 (1H, dd, J=9.0, 0.6 Hz), 7.04 (1H, dd, J=10.5, 8.7 Hz), 8.46 (1H, dd, J=9.0, 3.0 Hz), 9.06 (1H, dd, J=2.7, 0.3 Hz).

(ii) Production of tert-butyl{2-fluoro-5-[(5-nitropyridin-2-yl)oxy]phenyl}carbamate A solution of 2-fluoro-5-[(5-nitropyridin-2-yl)oxy]aniline (7.43 g, 30 mmol) and di-tert-butyl bicarbonate (10.9 g, 50 mmol) in tetrahydrofuran (50 ml) was refluxed overnight. The reaction mixture was poured into water (200 mL), and the mixture was extracted with ethyl acetate (100 mL×2). The ethyl acetate layers were combined and dried over anhydrous sodium sulfate. The insoluble material was filtered off, and the filtrate was concentrated under reduced pressure. The obtained residue was triturated with diethyl ether to give the title compound (9.41 g, 90%) as a colorless powder.

$^1$H-NMR (DMSO-d$_6$, 300 MHz) δ 1.51 (9H, s), 6.73-6.79 (1H, m), 6.81 (1H, br s), 7.03 (1H, d, J=9.0 Hz), 7.13 (1H, dd, J=10.5, 9.0 Hz), 8.02 (1H, d, J=4.5 Hz), 8.47 (1H, dd, J=9.0, 3.0 Hz), 9.04 (1H, d, J=2.7 Hz).

(iii) Production of tert-butyl {5-[(5-aminopyridin-2-yl)oxy]-2-fluorophenyl}carbamate A suspension of tert-butyl {2-fluoro-5-[(5-nitropyridin-2-yl)oxy]phenyl}carbamate (3.49 g, 10 mmol) and 10% palladium-carbon (1.0 g) in methanol (20 mL)-tetrahydrofuran (20 mL) was vigorously stirred at room temperature overnight under a hydrogen atmosphere. The insoluble material was filtered off, and the filtrate was concentrated under reduced pressure. The to residue was poured into water (200 mL), and the mixture was extracted with ethyl acetate (100 mL×2). The ethyl acetate layers were combined and dried over anhydrous sodium sulfate. The insoluble material was filtered off, and the filtrate was concentrated under reduced pressure. The residue was triturated with diethyl ether to give the title compound (3.00 g, 94%) as a colorless powder.

$^1$H-NMR (DMSO-d$_6$, 300 MHz) δ 1.50 (9H, s), 3.49 (2H, br s), 6.65-6.70 (1H, m), 6.71 (1H, br s), 6.75 (1H, d, J=8.7 Hz), 7.02 (1H, dd, J=10.5, 9.0 Hz), 7.07 (1H, dd, J=8.4, 3.0 Hz), 7.68 (1H, d, J=3.0 Hz), 7.88 (1H, d, J=2.7 Hz).

(iv) Production of tert-butyl{5-[(2-amino[1,3]thiazolo[5,4-b]pyridin-5-yl)oxy]-2-fluorophenyl}carbamate To a solution of tert-butyl {5-[(5-aminopyridin-2-yl)oxy]-2-fluorophenyl}carbamate (3.00 g, 9.4 mmol) and potassium thiocyanate (3.93 g, 40 mmol) in acetic acid (40 mL) was added dropwise bromine (2.40 g, 15 mmol) under ice-cooling, and the mixture was stirred at room temperature overnight. The yellow insoluble material was filtered off, and the filtrate was concentrated under reduced pressure. Saturated aqueous sodium hydrogen carbonate solution (200 mL) was added to the residue, and the mixture was extracted with ethyl acetate (100 mL×2). The ethyl acetate layers were combined and dried over anhydrous sodium sulfate. The insoluble material was filtered off, and the filtrate was concentrated under reduced pressure. The obtained residue was triturated with diethyl ether to give the title compound (3.20 g, 90%) as a pale-yellow powder.

$^1$H-NMR (DMSO-d$_6$, 300 MHz) δ 1.51 (9H, s), 5.49 (2H, br s), 6.71-6.76 (2H, m), 6.85 (1H, d, J=8.4 Hz), 7.06 (1H, dd, J=10.5, 9.0 Hz), 7.73 (1H, d, J=8.7 Hz), 8.30 (1H, br s).

(v) Production of tert-butyl (5-{[2-(cyclopropylcarbonyl)amino[1,3]thiazolo[5,4-b]pyridin-5-yl]oxy}-2-fluorophenyl)carbamate To a solution of tert-butyl {5-[(2-amino[1,3]thiazolo[5,4-b]pyridin-5-yl)oxy]-2-fluorophenyl}carbamate (1.13 g, 3.0 mmol) and N,N-dimethylpyridin-4-amine (1.22 g, 10 mmol) in pyridine (10 mL) was added dropwise cyclopropanecarbonyl chloride (1.05 g, 10 mmol) under ice-cooling, and the mixture was stirred at room temperature overnight. Water (200 mL) was added to the reaction mixture, and the mixture was extracted with ethyl acetate (100 mL×2). The ethyl acetate layers were combined and dried over anhydrous magnesium sulfate. The insoluble material was filtered off, and the filtrate was concentrated under reduced pressure. The obtained residue was triturated with diethyl ether to give the title compound (0.78 g, 59%) as a pale-yellow powder.

$^1$H-NMR (DMSO-d$_6$, 300 MHz) δ 1.02-1.10 (2H, m), 1.21-1.28 (2H, m), 1.50 (9H, s), 1.58-1.67 (1H, m), 6.76-6.81 (2H, m), 6.95 (1H, d, J=8.7 Hz), 7.08 (1H, dd, J=10.8, 9.0 Hz), 7.96 (1H, d, J=3.6 Hz), 7.97 (1H, br s), 10.12 (1H, br s).

(vi) Production of N-[5-(3-amino-4-fluorophenoxy)[1,3]thiazolo[5,4-b]pyridin-2-yl]cyclopropanecarboxamide A solution of tert-butyl (5-{[2-(cyclopropylcarbonyl)amino[1,3]thiazolo[5,4-b]pyridin-5-yl]oxy}-2-fluorophenyl)carbamate (0.78 g, 1.75 mmol) in trifluoroacetic acid (5 mL) was stirred at room temperature for 30 min. The reaction mixture was concentrated under reduced pressure, and the residue was diluted with ethyl acetate (100 mL), washed with 0.1N aqueous sodium hydroxide solution (100 mL), and dried over anhydrous magnesium sulfate. The insoluble material was filtered off, and the filtrate was concentrated under reduced pressure. The obtained residue was triturated with diethyl ether to give the title compound (0.60 g, quantitative) as a colorless powder.

$^1$H-NMR (DMSO-d$_6$, 300 MHz) δ 0.91-0.99 (2H, m), 1.11-1.19 (2H, m), 1.90-1.98 (1H, m), 4.03 (2H, br s), 6.40-6.44 (1H, m), 6.60 (1H, dd, J=7.5, 2.7 Hz), 6.88 (1H, d, J=8.7 Hz), 6.97 (1H, dd, J=10.5, 9.0 Hz), 7.92 (1H, d, J=8.7 Hz), 11.85 (1H, br s).

(vii) Production of N-{5-[4-fluoro-3-({[4-(trifluoromethoxy)phenyl]carbamoyl}amino)phenoxy][1,3]thiazolo[5,4-b]pyridin-2-yl}cyclopropanecarboxamide N-[5-(3-Amino-4-fluorophenoxy)[1,3]thiazolo[5,4-b]pyridin-2-yl]cyclopropanecarboxamide (150 mg, 0.44 mmol) was dissolved in pyridine (3.0 mL), 1-isocyanato-4-(trifluoromethoxy)benzene (99 μL, 0.66 mmol) was added, and the mixture was stirred at 70° C. for 2 hr. 1-Isocyanato-4-(trifluoromethoxy)benzene (20 μL, 0.13 mmol) was added to the reaction mixture, and the mixture was further stirred at 70° C. for 3 hr. The obtained suspension was cooled to room temperature, and diluted with ethyl acetate (5 mL), tetrahydrofuran (1 mL) and n-hexane (5 mL). The precipitated resultant product was collected by filtration to give the title compound (177 mg, 74%) as a colorless powder.

$^1$H-NMR (DMSO-$d_6$, 300 MHz) δ 0.76-1.15 (4H, m), 1.92-2.08 (1H, m), 6.72-6.91 (1H, m), 7.12 (1H, d, J=8.7 Hz), 7.21-7.37 (3H, m), 7.45-7.60 (2H, m), 7.98 (1H, dd, J=6.8, 3.0 Hz), 8.15 (1H, d, J=8.7 Hz), 8.75 (1H, d, J=2.5 Hz), 9.33 (1H, s), 12.70 (1H, br s).

Example 17

Production of N-{5-[3-({[4-chloro-3-(trifluoromethyl)phenyl]carbamoyl}amino)-4-fluorophenoxy][1,3]thiazolo[5,4-b]pyridin-2-yl}cyclopropanecarboxamide

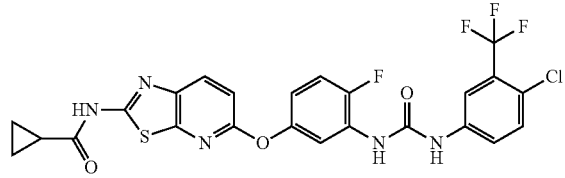 [SMILES: O=C(Nc1ccc(Cl)c(C(F)(F)F)c1)Nc1cc(Oc2ccc3nc(NC(=O)C4CC4)sc3n2)ccc1F]

N-[5-(3-Amino-4-fluorophenoxy)[1,3]thiazolo[5,4-b]pyridin-2-yl]cyclopropanecarboxamide (150 mg, 0.44 mmol) produced in Example 16(vi) was dissolved in pyridine (3.0 ml), 1-chloro-4-isocyanato-2-(trifluoromethyl)benzene (145 mg, 0.65 mmol) was added, and the mixture was stirred at 70° C. for 12 hr. 1-Chloro-4-isocyanato-2-(trifluoromethyl)benzene (70 mg, 0.32 mmol) was added to the reaction mixture, and the mixture was further stirred at 70° C. for 4 hr. The reaction mixture was cooled to room temperature, diluted with ethyl acetate (10 mL) and tetrahydrofuran (1 mL), and washed successively with saturated aqueous sodium hydrogen carbonate solution (10 mL) and saturated brine (10 mL). The organic layer was dried over anhydrous sodium sulfate and concentrated under reduced pressure. The obtained residue was suspended in ethyl acetate (5 mL), and the suspension was stirred at room temperature for 10 min. The solid was collected by filtration, and washed successively with ethyl acetate and n-hexane to give the title compound (170 mg, 70%) as a colorless powder.

$^1$H-NMR (DMSO-$d_6$, 300 MHz) δ 0.89-1.02 (4H, m), 1.93-2.06 (1H, m), 6.80-6.94 (1H, m), 7.13 (1H, d, J=8.7 Hz), 7.33 (1H, dd, J=11.0, 8.9 Hz), 7.52-7.67 (2H, m), 7.95 (1H, dd, J=6.9, 2.9 Hz), 8.06 (1H, d, J=2.4 Hz), 8.17 (1H, d, J=8.7 Hz), 8.82 (1H, d, J=2.4 Hz), 9.57 (1H, s), 12.70 (1H, s).

Example 18

Production of N-[5-(3-{[amino(phenyl)acetyl]amino}-4-fluorophenoxy)[1,3]thiazolo[5,4-b]pyridin-2-yl]cyclopropanecarboxamide

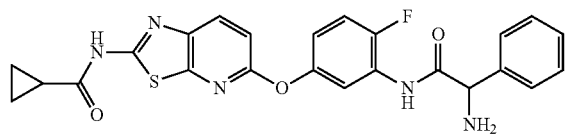 [SMILES: NC(C(=O)Nc1cc(Oc2ccc3nc(NC(=O)C4CC4)sc3n2)ccc1F)c1ccccc1]

N-[5-(3-Amino-4-fluorophenoxy)[1,3]thiazolo[5,4-b]pyridin-2-yl]cyclopropanecarboxamide (200 mg, 0.58 mmol) produced in Example 16(vi) was dissolved in pyridine (3.0 mL), [(tert-butoxycarbonyl)amino](phenyl)acetic acid (290 mg, 1.2 mmol) and O-(7-azabenzotriazol-1-yl)-N,N,N',N'-tetramethyluronium hexafluorophosphate (440 mg, 1.2 mmol) were added, and the mixture was stirred at 60° C. for 7 hr. [(tert-Butoxycarbonyl)amino](phenyl)acetic acid (145 mg, 0.58 mmol) and O-(7-azabenzotriazol-1-yl)-N,N,N',N'-tetramethyluronium hexafluorophosphate (220 mg, 0.58 mmol) were added to the reaction mixture, and the mixture was further stirred at 60° C. for 1 hr. The reaction mixture was cooled to room temperature, diluted with ethyl acetate (10 mL), and washed successively with 5% aqueous ammonium chloride solution (10 ml), saturated aqueous sodium hydrogen carbonate solution (5 mL) and saturated brine (5 mL). The organic layer was dried over anhydrous sodium sulfate and concentrated under reduced pressure. The obtained residue was dissolved in trifluoroacetic acid (4 mL), and the mixture was stirred at room temperature for 1 hr. The reaction mixture was concentrated under reduced pressure, and the obtained residue was diluted with ethyl acetate (20 mL), and washed successively with saturated aqueous sodium hydrogen carbonate solution (20 mL) and saturated brine (20 mL). The organic layer was dried over anhydrous sodium sulfate and concentrated under reduced pressure. The obtained residue was purified by silica gel column chromatography (ethyl acetate/hexane=40/60→100/0), and the obtained oil residue was crystallized from ethyl acetate/heptane to give the title compound (150 mg, 53%) as a pale-yellow powder.

$^1$H-NMR (DMSO-$d_6$, 300 MHz) δ 0.90-1.02 (4H, m), 1.91-2.08 (1H, m), 4.62 (1H, s), 6.86-7.01 (1H, m), 7.11 (1H, d, J=8.7 Hz), 7.21-7.51 (6H, m), 7.91 (1H, dd, J=6.6, 2.8 Hz), 8.15 (1H, d, J=8.7 Hz).

Example 19

Production of N-{5-[4-fluoro-3-({[2-(trifluoromethyl)phenyl]acetyl}amino)phenoxy][1,3]thiazolo[5,4-b]pyridin-2-yl}cyclopropanecarboxamide

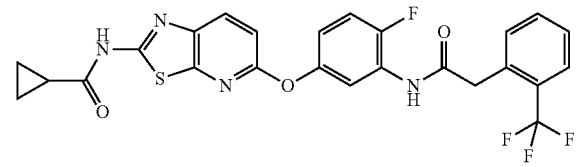 [SMILES: O=C(Cc1ccccc1C(F)(F)F)Nc1cc(Oc2ccc3nc(NC(=O)C4CC4)sc3n2)ccc1F]

N-[5-(3-Amino-4-fluorophenoxy)[1,3]thiazolo[5,4-b]pyridin-2-yl]cyclopropanecarboxamide (100 mg, 0.29 mmol) produced in Example 16(vi) was dissolved in pyridine (2.0 mL), [2-(trifluoromethyl)phenyl]acetic acid (120 mg, 0.58 mmol) and O-(7-azabenzotriazol-1-yl)-N,N,N',N'-tetramethyluronium hexafluorophosphate (220 mg, 0.58 mmol) were added, and the mixture was stirred at 80° C. for 4 hr. The reaction mixture was cooled to room temperature, diluted with ethyl acetate (10 mL), and washed successively with 5% aqueous ammonium chloride solution (5 mL), saturated aqueous sodium hydrogen carbonate solution (5 mL) and saturated brine (5 mL). The organic layer was dried over anhydrous sodium sulfate and concentrated under reduced pressure. The obtained residue was purified by basic silica gel column chromatography (ethyl acetate/hexane=40/60→100/0), and the obtained solid was washed with ethyl acetate/heptane to give the title compound (120 mg, 79%) as a colorless powder.

$^1$H-NMR (DMSO-d$_6$, 300 MHz) δ 0.88-1.02 (4H, m), 1.92-2.06 (1H, m), 4.02 (2H, s), 6.96 (1H, dt, J=8.6, 3.6 Hz), 7.11 (1H, d, J=8.7 Hz), 7.34 (1H, dd, J=10.7, 9.0 Hz), 7.41-7.54 (2H, m), 7.55-7.73 (2H, m), 7.77 (1H, dd, J=6.5, 2.9 Hz), 8.15 (1H, d, J=8.7 Hz), 10.16 (1H, s), 12.69 (1H, s).

Example 20

Production of N-(5-{4-fluoro-3-[(thiophen-3-ylacetyl)amino]phenoxy}[1,3]thiazolo[5,4-b]pyridin-2-yl)cyclopropanecarboxamide

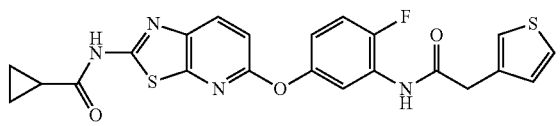 [SMILES: O=C(Cc1ccsc1)Nc1cc(Oc2ccc3nc(NC(=O)C4CC4)sc3n2)ccc1F]

N-[5-(3-Amino-4-fluorophenoxy)[1,3]thiazolo[5,4-b]pyridin-2-yl]cyclopropanecarboxamide (55 mg, 0.16 mmol) produced in Example 16(vi) was dissolved in pyridine (2.0 mL), thiophen-3-ylacetic acid (45 mg, 0.32 mmol) and O-(7-azabenzotriazol-1-yl)-N,N,N',N'-tetramethyluronium hexafluorophosphate (120 mg, 0.32 mmol) were added, and the mixture was stirred at 80° C. for 12 hr. The reaction mixture was cooled to room temperature, diluted with ethyl acetate (5 mL), and washed successively with 5% aqueous ammonium chloride solution (5 mL), saturated aqueous sodium hydrogen carbonate solution (5 mL) and saturated brine (5 mL). The organic layer was dried over anhydrous sodium sulfate and concentrated under reduced pressure. The obtained residue was purified by basic silica gel column chromatography (ethyl acetate/hexane=40/60→100/0), and the obtained solution was concentrated under reduced pressure. The obtained residue was washed with ethyl acetate/heptane to give the title compound (51 mg, 68%) as a colorless powder.

$^1$H-NMR (DMSO-d$_6$, 300 MHz) δ 0.88-1.04 (4H, m), 1.92-2.08 (1H, m), 3.75 (2H, s), 6.80-7.02 (1H, m), 7.03-7.19 (2H, m), 7.24-7.41 (2H, m), 7.47 (1H, dd, J=4.9, 3.0 Hz), 7.82 (1H, dd, J=6.6, 2.8 Hz), 8.15 (1H, d, J=8.7 Hz), 10.04 (1H, s), 12.69 (1H, br s).

Example 21

Production of N-{5-[4-fluoro-3-[{(4-(trifluoromethyl)phenyl]acetyl}amino)phenoxy][1,3]thiazolo[5,4-b]pyridin-2-yl}cyclopropanecarboxamide

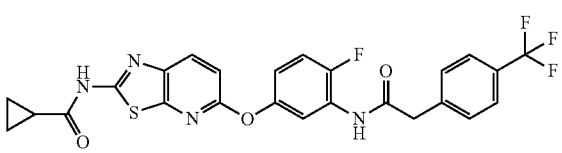 [SMILES: O=C(Cc1ccc(C(F)(F)F)cc1)Nc1cc(Oc2ccc3nc(NC(=O)C4CC4)sc3n2)ccc1F]

N-[5-(3-Amino-4-fluorophenoxy)[1,3]thiazolo[5,4-b]pyridin-2-yl]cyclopropanecarboxamide (100 mg, 0.29 mmol) produced in Example 16(vi) was dissolved in pyridine (2.0 mL), [4-(trifluoromethyl)phenyl]acetic acid (120 mg, 0.58 mmol) and O-(7-azabenzotriazol-1-yl)-N,N,N',N'-tetramethyluronium hexafluorophosphate (220 mg, 0.58 mmol) were added, and the mixture was stirred at 80° C. for 12 hr. The reaction mixture was cooled to room temperature, diluted with ethyl acetate (10 mL), and washed successively with 5% aqueous ammonium chloride solution (10 mL), saturated aqueous sodium hydrogen carbonate solution (10 mL) and saturated brine (10 mL). The organic layer was dried over anhydrous sodium sulfate and concentrated under reduced pressure. The obtained residue was purified by basic silica gel column chromatography (ethyl acetate/hexane=40/60→100/0), and the obtained solution was concentrated under reduced pressure. The obtained residue was washed with ethyl acetate/heptane to give the title compound (82 mg, 53%) as a colorless powder.

$^1$H-NMR (DMSO-d$_6$, 300 MHz) δ 0.84-1.07 (4H, m), 1.91-2.06 (1H, m), 3.87 (2H, s), 6.86-7.03 (1H, m), 7.10 (1H, d, J=8.7 Hz), 7.33 (1H, dd, J=10.6, 8.9 Hz), 7.45-7.74 (4H, m), 7.80 (1H, dd, J=6.5, 2.9 Hz), 8.14 (1H, d, J=8.7 Hz), 10.18 (1H, s), 12.69 (1H, br s).

Example 22

Production of N-{5-[4-fluoro-3-({[3-(trifluoromethyl)phenyl]acetyl}amino)phenoxy][1,3]thiazolo[5,4-b]pyridin-2-yl}cyclopropanecarboxamide

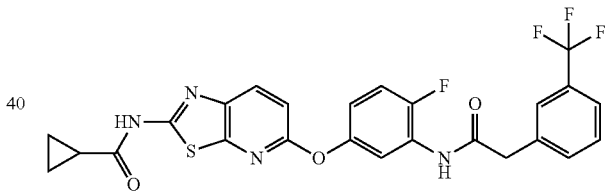

N-[5-(3-Amino-4-fluorophenoxy)[1,3]thiazolo[5,4-b]pyridin-2-yl]cyclopropanecarboxamide (150 mg, 0.44 mmol) produced in Example 16(vi) was dissolved in N,N-dimethylacetamide (3.0 mL)/pyridine (9.0 mL), [3-(trifluoromethyl)phenyl]acetic acid (110 mg, 0.52 mmol) and 0-(7-azabenzotriazol-1-yl)-N,N,N',N'-tetramethyluronium hexafluorophosphate (330 mg, 0.65 mmol) were added, and the mixture was stirred at 90° C. for 2 hr. The reaction mixture was cooled to room temperature, diluted with ethyl acetate (27 mL), and washed successively with water (27 mL) and saturated brine (27 mL). The organic layer was dried over anhydrous sodium sulfate and concentrated under reduced pressure. The obtained residue was purified by basic silica gel column chromatography (ethyl acetate/hexane=50/50→100/0), and the obtained solution was concentrated under reduced pressure. The residue was recrystallized from ethyl acetate/heptane to give the title compound (78 mg, 34%) as a colorless powder.

$^1$H-NMR (DMSO-d$_6$, 300 MHz) δ 0.87-1.04 (4H, m), 1.93-2.10 (1H, m), 3.88 (2H, s), 6.89-7.01 (1H, m), 7.11 (1H, d, J=8.7 Hz), 7.34 (1H, dd, J=10.7, 9.0 Hz), 7.47-7.66 (3H, m), 7.69 (1H, s), 7.80 (1H, dd, J=6.6, 2.8 Hz), 8.15 (1H, d, J=8.7 Hz), 10.17 (1H, s), 12.69 (1H, s).

Example 23

Production of N-{5-[4-fluoro-3-({[3-(trifluoromethyl)phenyl]carbamoyl}amino)phenoxy][1,3]thiazolo[5,4-b]pyridin-2-yl}cyclopropanecarboxamide

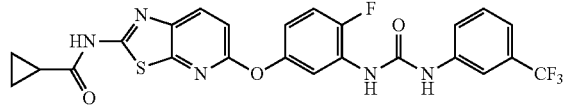 [SMILES: O=C(Nc1cccc(C(F)(F)F)c1)Nc1cc(Oc2ccc3nc(NC(=O)C4CC4)sc3n2)ccc1F]

To a solution of N-[5-(3-amino-4-fluorophenoxy)[1,3]thiazolo[5,4-b]pyridin-2-yl]cyclopropanecarboxamide (150 mg, 0.436 mmol) produced in Example 16(vi) in pyridine (4 mL) was added 1-isocyanato-3-(trifluoromethyl)benzene (120 μL, 0.871 mmol), and the mixture was stirred at 90° C. for 2 hr. The reaction mixture was diluted with ethyl acetate (15 mL)/tetrahydrofuran (5 mL), and washed successively with aqueous sodium hydrogen carbonate solution (15 mL) and saturated brine (5 mL). The organic layer was dried over anhydrous sodium sulfate and concentrated under reduced pressure. The obtained residue was washed with acetone (15 mL) to give the title compound (69 mg, 37%) as a white solid.
$^1$H-NMR (DMSO-$d_6$, 300 MHz) δ 0.86-1.04 (4H, m), 1.93-2.05 (1H, m), 6.85 (1H, ddd, J=8.9, 4.0, 3.1 Hz), 7.12 (1H, d, J=8.7 Hz), 7.27-7.39 (2H, m), 7.48-7.56 (2H, m), 7.94-8.03 (2H, m), 8.16 (1H, d, J=8.7 Hz), 8.82 (1H, d, J=2.3 Hz), 9.49 (1H, br s), 12.70 (1H, br s).

Example 24

Production of N-{5-[4-fluoro-3-({[4-(trifluoromethyl)phenyl]carbamoyl}amino)phenoxy][1,3]thiazolo[5,4-b]pyridin-2-yl}cyclopropanecarboxamide

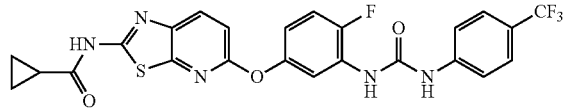

To a solution of N-[5-(3-amino-4-fluorophenoxy)[1,3]thiazolo[5,4-b]pyridin-2-yl]cyclopropanecarboxamide (100 mg, 0.290 mmol) produced in Example 16(vi) in pyridine (3 mL) was added 1-isocyanato-4-(trifluoromethyl)benzene (50 μL, 0.348 mmol), and the mixture was stirred at room temperature for 2 hr. The reaction mixture was concentrated under reduced pressure, and the obtained residue was purified by basic silica gel column chromatography (methanol/ethyl acetate=5/95→10/90). The obtained solution was concentrated under reduced pressure to give the title compound (58 mg, 37%) as a white solid.
$^1$H-NMR (DMSO-$d_6$, 300 MHz) δ 0.84-1.05 (4H, m), 1.93-2.06 (1H, m), 6.85 (1H, ddd, J=8.9, 4.0, 2.9 Hz), 7.13 (1H, d, J=8.7 Hz), 7.33 (1H, dd, J=11.0, 8.9 Hz), 7.63 (4H, br s), 7.98 (1H, dd, J=6.9, 2.9 Hz), 8.17 (1H, d, J=8.7 Hz), 8.83 (1H, d, J=2.6 Hz), 9.53 (1H, br s), 12.70 (1H, br s).

Example 25

Production of N-{5-[4-fluoro-3-({[2-(trifluoromethyl)phenyl]carbamoyl}amino)phenoxy][1,3]thiazolo[5,4-b]pyridin-2-yl}cyclopropanecarboxamide

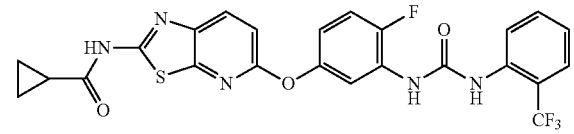 [SMILES: O=C(Nc1cc(Oc2ccc3nc(NC(=O)C4CC4)sc3n2)ccc1F)Nc1ccccc1C(F)(F)F]

To a solution of N-[5-(3-amino-4-fluorophenoxy)[1,3]thiazolo[5,4-b]pyridin-2-yl]cyclopropanecarboxamide (100 mg, 0.290 mmol) produced in Example 16(vi) in pyridine (3 mL) was added 1-isocyanato-2-(trifluoromethyl)benzene (53 μL, 0.348 mmol), and the mixture was stirred at room temperature for 30 min. The reaction mixture was diluted with ethyl acetate (15 mL)/tetrahydrofuran (5 mL), and washed successively with aqueous sodium hydrogen carbonate solution (15 mL) and saturated brine (5 mL). The organic layer was dried over anhydrous sodium sulfate and concentrated under reduced pressure. The obtained residue was purified by basic silica gel column chromatography (ethyl acetate/hexane=50/50→90/10), and the obtained solution was concentrated under reduced pressure. The obtained residue was washed with ethyl acetate (10 mL) to give the title compound (95 mg, 61%) as a white solid.
$^1$H-NMR (DMSO-$d_6$, 300 MHz) δ 0.82-1.00 (4H, m), 1.92-2.04 (1H, m), 6.83 (1H, ddd, J=8.9, 4.0, 2.9 Hz), 7.11 (1H, d, J=8.7 Hz), 7.25-7.38 (2H, m), 7.61 (1H, t, J=7.8 Hz), 7.68 (1H, dd, J=7.8, 1.2 Hz), 7.82 (1H, d, J=8.3 Hz), 8.00 (1H, dd, J=6.9, 2.9 Hz), 8.14 (1H, d, J=8.7 Hz), 8.65 (1H, br s), 9.44 (1H, d, J=2.3 Hz), 12.68 (1H, br s).

Example 26

Production of N-{5-[4-fluoro-3-({[3-(trifluoromethyl)benzyl]carbamoyl}amino)phenoxy][1,3]thiazolo[5,4-b]pyridin-2-yl}cyclopropanecarboxamide

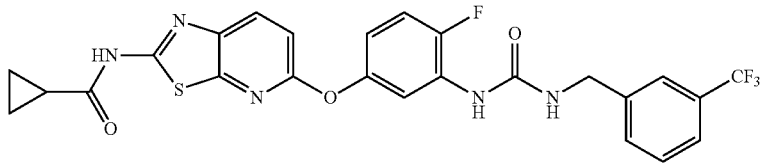 [SMILES: O=C(NCc1cccc(C(F)(F)F)c1)Nc1cc(Oc2ccc3nc(NC(=O)C4CC4)sc3n2)ccc1F]

To a solution of bis(trichloromethyl) carbonate (30 mg, 0.102 mmol) in tetrahydrofuran (2 mL) was added dropwise a suspension of N-[5-(3-amino-4-fluorophenoxy)[1,3]thiazolo[5,4-b]pyridin-2-yl]cyclopropanecarboxamide (100 mg, 0.290 mmol) produced in Example 16(vi) and triethylamine (80 μL, 0.580 mmol) in tetrahydrofuran (2 mL) at 0° C., and the mixture was stirred at 0° C. for 30 min. 1-[3-(Trifluoromethyl)phenyl]methanamine (50 μL, 0.348 mmol) was added to the reaction mixture, and the mixture was stirred at room temperature for 2.5 hr. The reaction mixture was diluted with ethyl acetate (20 mL), and washed successively with aqueous sodium hydrogen carbonate solution (15 mL) and saturated brine (5 mL). The organic layer was dried over anhydrous sodium sulfate and concentrated under reduced pressure. The obtained residue was purified by basic silica gel column chromatography (ethyl acetate/hexane=50/50→70/30), and the obtained solution was concentrated under reduced pressure.

The obtained residue was washed with ethyl acetate (5 ml) to give the title compound (62 mg, 39%) as a white solid.
$^1$H-NMR (DMSO-d$_6$, 300 MHz) δ 0.86-1.02 (4H, m), 1.93-2.05 (1H, m), 4.47 (2H, d, J=5.9 Hz), 6.74 (1H, ddd, J=8.9, 4.0, 2.9 Hz), 7.09 (1H, d, J=8.8 Hz), 7.23 (1H, t, J=5.9 Hz), 7.26 (1H, dd, J=11.3, 8.9 Hz), 7.47 (1H, t, J=7.8 Hz), 7.57 (1H, d, J=7.8 Hz), 7.63-7.75 (2H, m), 7.98 (1H, dd, J=6.9, 2.9 Hz), 8.14 (1H, d, J=8.8 Hz), 8.72 (1H, d, J=2.5 Hz), 12.68 (1H, br s).

Example 28

Production of N-{5-[4-fluoro-3-({[4-(trifluoromethyl)benzyl]carbamoyl}amino)phenoxy][1,3]thiazolo[5,4-b]pyridin-2-yl}cyclopropanecarboxamide

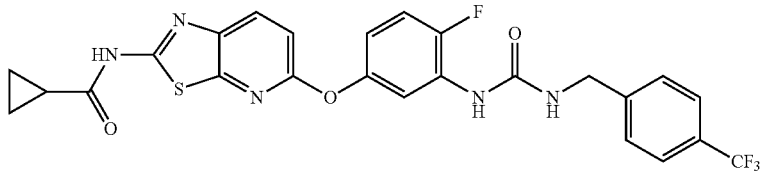

The obtained residue was washed with ethyl acetate (3 mL) to give the title compound (80 mg, 50%) as a white solid.
$^1$H-NMR (DMSO-d$_6$, 300 MHz) δ 0.87-1.01 (4H, m), 1.92-2.04 (1H, m), 4.38 (2H, d, J=5.9 Hz), 6.74 (1H, ddd, J=8.9, 3.9, 2.9 Hz), 7.08 (1H, d, J=8.7 Hz), 7.19-7.31 (2H, m), 7.53-7.66 (4H, m), 7.96 (1H, dd, J=6.9, 2.9 Hz), 8.13 (1H, d, J=8.7 Hz), 8.63 (1H, d, J=2.5 Hz), 12.68 (1H, br s).

Example 27

Production of N-{5-[4-fluoro-3-({[2-(trifluoromethyl)benzyl]carbamoyl}amino)phenoxy][1,3]thiazolo[5,4-b]pyridin-2-yl}cyclopropanecarboxamide

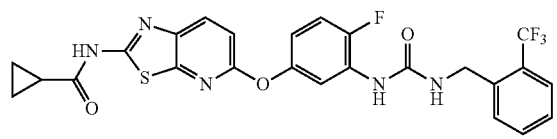 [SMILES: O=C(NCc1ccccc1C(F)(F)F)Nc1cc(Oc2ccc3nc(NC(=O)C4CC4)sc3n2)ccc1F]

To a solution of bis(trichloromethyl) carbonate (30 mg, 0.102 mmol) in tetrahydrofuran (2 mL) was dropwise added a suspension of N-[5-(3-amino-4-fluorophenoxy)[1,3]thiazolo[5,4-b]pyridin-2-yl]cyclopropanecarboxamide (100 mg, 0.290 mmol) produced in Example 16(vi) and triethylamine (80 μL, 0.580 mmol) in tetrahydrofuran (2 mL) at 0° C., and the mixture was stirred at 0° C. for 30 min. 1-[2-(Trifluoromethyl)phenyl]methanamine (49 μL, 0.348 mmol) was added to the reaction mixture, and the mixture was stirred at room temperature for 1.5 hr. The reaction mixture was diluted with ethyl acetate (20 mL), and washed successively with aqueous sodium hydrogen carbonate solution (15 mL) and saturated brine (5 mL). The organic layer was dried over anhydrous sodium sulfate and concentrated under reduced pressure. The obtained residue was purified by basic silica gel column chromatography (ethyl acetate/hexane=50/50→70/30), and the obtained solution was concentrated under reduced pressure.

To a solution of bis(trichloromethyl) carbonate (30 mg, 0.102 mmol) in tetrahydrofuran (2 mL) was added dropwise a suspension of N-[5-(3-amino-4-fluorophenoxy)[1,3]thiazolo[5,4-b]pyridin-2-yl]cyclopropanecarboxamide (100 mg, 0.290 mmol) produced in Example 16(vi) and triethylamine (80 μL, 0.580 mmol) in tetrahydrofuran (2 mL) at 0° C., and the mixture was stirred at 0° C. for 30 min. 1-[4-(Trifluoromethyl)phenyl]methanamine (50 μL, 0.348 mmol) was added to the reaction mixture, and the mixture was stirred at room temperature for 1.5 hr. The reaction mixture was diluted with ethyl acetate (20 mL), and washed successively with aqueous sodium hydrogen carbonate solution (15 mL) and saturated brine (5 mL). The solid precipitated in the organic layer was collected by filtration to give the title compound (65 mg, 41%) as a white solid.
$^1$H-NMR (DMSO-d$_6$, 300 MHz) δ 0.89-1.01 (4H, m), 1.91-2.04 (1H, m), 4.38 (2H, d, J=6.2 Hz), 6.66-6.80 (1H, m), 7.07 (1H, d, J=8.8 Hz), 7.19-7.32 (2H, m), 7.49 (2H, d, J=8.0 Hz), 7.69 (2H, d, J=8.0 Hz), 7.97 (1H, dd, J=6.9, 2.9 Hz), 8.12 (1H, d, J=8.8 Hz), 8.65 (1H, d, J=2.6 Hz), 12.67 (1H, br s).

Example 29

Production of N-{5-[4-fluoro-3-({[6-(trifluoromethyl)pyridin-3-yl]carbamoyl}amino)phenoxy][1,3]thiazolo[5,4-b]pyridin-2-yl}cyclopropanecarboxamide

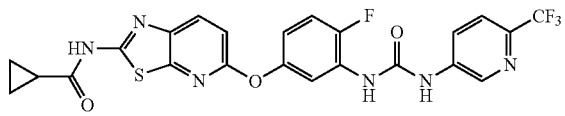 [SMILES: O=C(Nc1ccc(C(F)(F)F)nc1)Nc1cc(Oc2ccc3nc(NC(=O)C4CC4)sc3n2)ccc1F]

To a solution of bis(trichloromethyl) carbonate (30 mg, 0.102 mmol) in tetrahydrofuran (2 mL) was added dropwise a suspension of N-[5-(3-amino-4-fluorophenoxy)[1,3]thiazolo[5,4-b]pyridin-2-yl]cyclopropanecarboxamide (100 mg, 0.290 mmol) produced in Example 16(vi) and triethylamine (80 μL, 0.580 mmol) in tetrahydrofuran (2 mL) at 0° C., and the mixture was stirred at 0° C. for 30 min. 6-(Trifluoromethyl)pyridin-3-amine (56 mg, 0.348 mmol) was added to the reaction mixture, and the mixture was stirred at 50° C. for 2 hr and at room temperature for 4 days. The reaction mixture was diluted with ethyl acetate (20 mL) and washed with aqueous sodium hydrogen carbonate solution (15 mL), and the insoluble material was filtered off. The filtrate was concentrated under reduced pressure, and the obtained residue was washed with acetone (3 mL) to give the title compound (40 mg, 26%) as a white solid.

$^1$H-NMR (DMSO-$d_6$, 300 MHz) δ 0.81-1.06 (4H, m), 1.92-2.05 (1H, m), 6.87 (1H, ddd, J=8.9, 3.9, 3.0 Hz), 7.13 (1H, d, J=8.7 Hz), 7.34 (1H, dd, J=11.0, 8.9 Hz), 7.81 (1H, d, J=8.7 Hz), 7.96 (1H, dd, J=6.8, 3.0 Hz), 8.16 (1H, d, J=8.7 Hz), 8.19 (1H, dd, J=8.7, 2.4 Hz), 8.69 (1H, d, J=2.4 Hz), 8.99 (1H, br s), 9.74 (1H, br s), 12.69 (1H, br s).

Example 30

Production of N-{5-[4-fluoro-3-({[3-(trifluoromethoxy)benzyl]carbamoyl}amino)phenoxy][1,3]thiazolo[5,4-b]pyridin-2-yl}cyclopropanecarboxamide

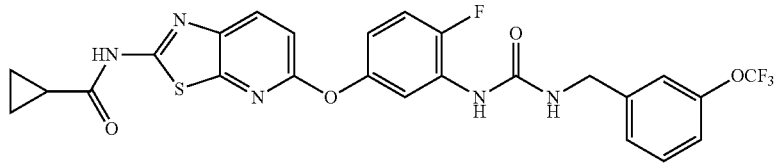 [SMILES: O=C(NCc1cccc(OC(F)(F)F)c1)Nc1cc(Oc2ccc3nc(NC(=O)C4CC4)sc3n2)ccc1F]

To a solution of bis(trichloromethyl) carbonate (30 mg, 0.102 mmol) in tetrahydrofuran (2 mL) was added dropwise a suspension of N—[5-(3-amino-4-fluorophenoxy)[1,3]thiazolo[5,4-b]pyridin-2-yl]cyclopropanecarboxamide (100 mg, 0.290 mmol) produced in Example 16(vi) and triethylamine (80 μL, 0.580 mmol) in tetrahydrofuran (2 ml) at 0° C., and the mixture was stirred at 0° C. for 30 min. 1-[3-(Trifluoromethoxy)phenyl]methanamine (59 μL, 0.348 mmol) was added to the reaction mixture, and the mixture was stirred at room temperature for 2 hr. The reaction mixture was diluted with ethyl acetate (20 mL), and washed successively with aqueous sodium hydrogen carbonate solution (15 mL) and saturated brine (5 ml). The organic layer was dried over anhydrous sodium sulfate and concentrated under reduced pressure. The obtained residue was purified by basic silica gel column chromatography (ethyl acetate/hexane=50/50→80/20), and the obtained solution was concentrated under reduced pressure. The obtained residue was recrystallized from tetrahydrofuran (3 mL)/ethyl acetate (2 mL) to give the title compound (85 mg, 52%) as a white solid.

$^1$H-NMR (DMSO-$d_6$, 300 MHz) δ 0.84-1.04 (4H, m), 1.93-2.05 (1H, m), 4.33 (2H, d, J=5.9 Hz), 6.74 (1H, ddd, J=8.9, 3.9, 2.9 Hz), 7.09 (1H, d, J=8.7 Hz), 7.17-7.35 (5H, m), 7.47 (1H, dt, J=0.6, 7.7 Hz), 7.96 (1H, dd, J=6.9, 2.9 Hz), 8.15 (1H, d, J=8.7 Hz), 8.62 (1H, d, J=2.5 Hz), 12.69 (1H, br s).

Example 31

Production of N-[5-(4-fluoro-3-{[(pyridin-2-ylmethyl)carbamoyl]amino}phenoxy)[1,3]thiazolo[5,4-b]pyridin-2-yl]cyclopropanecarboxamide

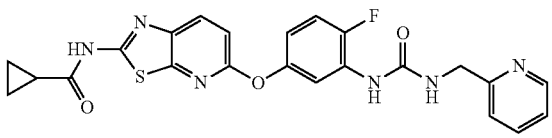 [SMILES: O=C(NCc1ccccn1)Nc1cc(Oc2ccc3nc(NC(=O)C4CC4)sc3n2)ccc1F]

To a solution of bis(trichloromethyl) carbonate (30 mg, 0.102 mmol) in tetrahydrofuran (2 mL) was added dropwise a suspension of N-[5-(3-amino-4-fluorophenoxy)[1,3]thiazolo[5,4-b]pyridin-2-yl]cyclopropanecarboxamide (100 mg, 0.290 mmol) produced in Example 16(vi) and triethylamine (80 μL, 0.580 mmol) in tetrahydrofuran (2 ml) at 0° C., and the mixture was stirred at 0° C. for 30 min. 1-Pyridin-2-ylmethanamine (40 μL, 0.348 mmol) was added to the reaction mixture, and the mixture was stirred at room temperature for 3 hr. Ethyl acetate (6 mL) and water (4 mL) were added to the reaction mixture, and the mixture was stirred at room temperature for 30 min. The precipitated solid was collected by filtration to give the title compound (81 mg, 58%) as a white solid.

$^1$H-NMR (DMSO-$d_6$, 300 MHz) δ 0.89-1.04 (4H, m), 1.93-2.07 (1H, m), 4.38 (2H, d, J=5.7 Hz), 6.73 (1H, ddd, J=8.9, 3.9, 2.9 Hz), 7.09 (1H, d, J=8.7 Hz), 7.21-7.37 (4H, m), 7.76 (1H, dt, J=1.8, 7.7 Hz), 7.99 (1H, dd, J=7.0, 2.9 Hz), 8.15 (1H, d, J=8.7 Hz), 8.52 (1H, ddd, J=4.9, 1.8, 0.8 Hz), 8.77 (1H, d, J=2.3 Hz), 12.52 (1H, br s).

Example 32

Production of N-[5-(4-fluoro-3-{[(2-phenoxyethyl)carbamoyl]amino}phenoxy)[1,3]thiazolo[5,4-b]pyridin-2-yl]cyclopropanecarboxamide

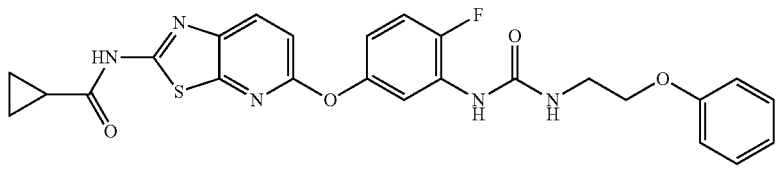 [SMILES: O=C(NCCOc1ccccc1)Nc1cc(Oc2ccc3nc(NC(=O)C4CC4)sc3n2)ccc1F]

To a solution of bis(trichloromethyl) carbonate (30 mg, 0.102 mmol) in tetrahydrofuran (2 mL) was added dropwise a suspension of N-[5-(3-amino-4-fluorophenoxy)[1,3]thiazolo[5,4-b]pyridin-2-yl]cyclopropanecarboxamide (100 mg, 0.290 mmol) produced in Example 16(vi) and triethylamine (100 μL, 0.725 mmol) in tetrahydrofuran (2 mL) at 0° C., and the mixture was stirred at 0° C. for 30 min. 2-Phenoxyethanamine (45 μL, 0.348 mmol) was added to the reaction mixture, and the mixture was stirred at room temperature for 3 hr. Ethyl acetate (6 ml) and water (4 mL) were added to the reaction mixture, and the mixture was stirred at room temperature for 30 min. The precipitated solid was collected by filtration to give the title compound (93 mg, 63%) as a white solid.

¹H-NMR (DMSO-d₆, 300 MHz) δ 0.88-1.04 (4H, m), 1.93-2.05 (1H, m), 3.45 (2H, q, J=5.4 Hz), 4.00 (2H, t, J=5.4 Hz), 6.73 (1H, ddd, J=8.8, 3.9, 3.0 Hz), 6.88-7.03 (4H, m), 7.09 (1H, d, J=8.7 Hz), 7.17-7.34 (3H, m), 7.99 (1H, dd, J=7.0, 3.0 Hz), 8.15 (1H, d, J=8.7 Hz), 8.60 (1H, d, J=2.6 Hz), 12.70 (1H, br s).

Example 33

Production of benzyl [3-({2-[(cyclopropylcarbonyl)amino][1,3]thiazolo[5,4-b]pyridin-5-yl}oxy)-4-methylphenyl]carbamate

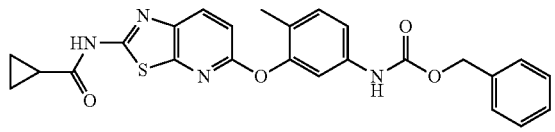 [SMILES: Cc1ccc(NC(=O)OCc2ccccc2)cc1Oc1ccc2nc(NC(=O)C3CC3)sc2n1]

(i) Production of benzyl (3-hydroxy-4-methylphenyl)carbamate

To a suspension of 5-amino-2-methylphenol (39.6 g, 321 mmol) and sodium hydrogen carbonate (40.5 g, 482 mmol) in tetrahydrofuran (300 mL)/water (150 mL) was added dropwise benzyl chlorocarbonate (48.1 mL, 321 mmol) at 0° C. over 30 min, and the mixture was stirred at room temperature for 30 min. The reaction mixture was diluted with ethyl acetate (300 mL) and washed with water (100 mL), and the obtained aqueous layer was extracted with ethyl acetate (2×100 ml). The combined organic layer was washed with saturated brine (100 mL), and purified by silica gel (ethyl acetate). The obtained solution was concentrated under reduced pressure to give the title compound (83.1 g, quantitatively) as a pale-brown solid. The obtained compound was used for the next reaction without purification.

¹H-NMR (DMSO-d₆, 300 MHz) δ 2.03 (3H, s), 5.12 (2H, s), 6.74 (1H, dd, J=8.4, 1.8 Hz), 6.90 (1H, d, J=8.4 Hz), 7.06 (1H, d, J=1.8 Hz), 7.26-7.49 (5H, m), 9.25 (1H, s), 9.52 (1H, s).

(ii) Production of benzyl {4-methyl-3-[(5-nitropyridin-2-yl)oxy]phenyl}carbamate To a solution of benzyl (3-hydroxy-4-methylphenyl)carbamate (83.1 g, 321 mmol) in N,N-dimethylformamide (300 mL) were added cesium carbonate (157 g, 482 mmol) and 2-chloro-5-nitropyridine (50.9 g, 321 mmol), and the mixture was stirred at room temperature for 4 hr. The reaction mixture was diluted with ethyl acetate (500 mL) and washed with water (1 L), and the obtained aqueous layer was extracted with ethyl acetate (2×200 mL). The combined organic layer was washed with saturated brine (100 mL) and purified by basic silica gel (ethyl acetate). The obtained solution was concentrated under reduced pressure. The obtained residue was washed with ethyl acetate/hexane (1:1) to give the title compound (91.8 g, 75%) as a pale-yellow solid.

¹H-NMR (DMSO-d₆, 300 MHz) δ 1.99 (3H, s), 5.13 (2H, s), 7.18-7.28 (3H, m), 7.29-7.46 (6H, m), 8.62 (1H, dd, J=9.2, 2.8 Hz), 9.01 (1H, dd, J=2.8, 0.4 Hz), 9.87 (1H, s).

(iii) Production of benzyl {3-[(5-aminopyridin-2-yl)oxy]-4-methylphenyl}carbamate To a solution of benzyl {4-methyl-3-[(5-nitropyridin-2-yl)oxy]phenyl}carbamate (36.9 g, 97.4 mmol) in ethanol (200 mL)/1-methylpyrrolidin-2-one (50 mL) were added 1N hydrochloric acid (50 mL) and reduced iron (27.2 g, 487 mmol), and the mixture was stirred at 100° C. for 3 hr. The reaction mixture was diluted with ethyl acetate (200 mL), and 2N aqueous sodium hydroxide solution (50 mL) was added. The insoluble material was filtered off through a celite pad, and the insoluble material was washed with ethyl acetate (1 L). Benzyl {4-methyl-3-[(5-nitropyridin-2-yl)oxy]phenyl}carbamate (38.3 g, 101 mmol) was treated in the same manner as above. The obtained filtrates were combined, washed with saturated brine (3×200 mL), and purified by silica gel (ethyl acetate). The obtained solution was concentrated under reduced pressure, and the crystals precipitated during concentration were collected by filtration to give the title compound (56.6 g, 82%) as a pale-orange solid.

¹H-NMR (DMSO-d₅, 300 MHz) δ 2.05 (3H, s), 5.02 (2H, s), 5.10 (2H, s), 6.70 (1H, d, J=8.5 Hz), 6.99-7.15 (4H, m), 7.25-7.43 (5H, m), 7.49 (1H, dd, J=2.8, 0.6 Hz), 9.67 (1H, s).

(iv) Production of benzyl {3-[(2-amino[1,3]thiazolo[5,4-b]pyridin-5-yl)oxy]-4-methylphenyl}carbamate To a solution of potassium thiocyanate (62.9 g, 647 mmol) in acetic acid (500 ml) was added benzyl {3-[(5-aminopyridin-2-yl)oxy]-4-methylphenyl}carbamate (56.5 g, 162 mmol), and a solution of bromine (27.1 g, 170 mmol) in acetic acid (100 mL) was added dropwise. The reaction mixture was stirred at room temperature for 18 hr, and the insoluble material was filtered off through a celite pad. The filtrate was concentrated under reduced pressure, and the obtained residue was diluted with ethyl acetate (500 mL) and washed with saturated aqueous sodium hydrogen carbonate solution (300 mL). The obtained aqueous layer was extracted with ethyl acetate (100 mL). The combined organic layer was washed with saturated brine (100 mL), and purified by silica gel (ethyl acetate). The obtained solution was concentrated under reduced pressure, and the crystals precipitated during concentration were collected by filtration to give the title compound (48.4 g, 74%) as a pale-brown solid.

¹H-NMR (DMSO-d₆, 300 MHz) δ 2.04 (3H, s), 5.11 (2H, s), 6.84 (1H, d, J=8.7 Hz), 7.16 (1H, s), 7.19 (2H, s), 7.27-7.44 (5H, m), 7.57 (2H, s), 7.70 (1H, d, J=8.7 Hz), 9.75 (1H, s).

(v) Production of benzyl [3-({2-[(cyclopropylcarbonyl)amino][1,3]thiazolo[5,4-b]pyridin-5-yl}oxy)-4-methylphenyl]carbamate To a solution of benzyl {3-[(2-amino[1,3]thiazolo[5,4-b]pyridin-5-yl)oxy]-4-methylphenyl}carbamate (25.1 g, 61.9 mmol) in pyridine (200 mL) was added cyclopropanecarbonyl chloride (9.47 mL, 105 mmol) at 0° C., and the mixture was stirred at room temperature for 30 min. Methanol (100 mL) and potassium carbonate (8.55 g, 61.9 mmol) were added to the reaction mixture, and the mixture was stirred at room temperature for 1 hr. The precipitated crystals were collected by filtration, and washed successively with methanol (200 mL), water (100 mL), methanol (100 mL) and hexane (100 mL) to give the title compound (23.9 g, 81%) as a white solid.

¹H-NMR (DMSO-d₆, 300 MHz) δ 0.83-1.01 (4H, m), 1.92-2.01 (1H, m), 2.03 (3H, s), 5.11 (2H, s), 7.06 (1H, d, J=8.7 Hz), 7.17-7.28 (3H, m), 7.27-7.43 (5H, m), 8.13 (1H, d, J=8.7 Hz), 9.80 (1H, s), 12.67 (1H, br s).

Reference Example 1

Production of N-[5-(5-amino-2-methylphenoxy)[1,3]thiazolo[5,4-b]pyridin-2-yl]cyclopropanecarboxamide

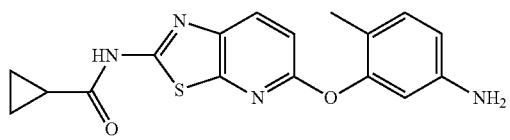 [SMILES: Cc1ccc(N)cc1Oc1ccc2nc(NC(=O)C3CC3)sc2n1]

To a solution of benzyl [3-({2-[(cyclopropylcarbonyl)amino][1,3]thiazolo[5,4-b]pyridin-5-yl}oxy)-4-methylphenyl]carbamate (14.4 g, 30.3 mmol) produced in Example 33(v) in ethanol (300 mL)/1-methylpyrrolidin-2-one (100 mL) were added 10% palladium carbon (27.3 g, 25.7 mmol) and ammonium formate (61.9 g, 909 mmol), and the mixture was stirred at room temperature for 5 days under a hydrogen atmosphere (1 atm). The insoluble material was filtered off through a celite pad, and the filtrate was concentrated under reduced pressure. To the obtained solution in 1-methylpyrrolidin-2-one was added water (300 ml), and the precipitated solid was collected by filtration and washed with water (500 mL). The solid collected by filtration was dissolved in a mixture of tetrahydrofuran (800 mL)/ethyl acetate (800 mL), washed with saturated brine (2×400 mL), dried over anhydrous sodium sulfate, and concentrated under reduced pressure. The obtained residue was washed successively with a mixture of tetrahydrofuran (10 mL)/diisopropyl ether (10 mL) and diisopropyl ether (40 mL) to give the title compound (7.29 g, 71%) as a white solid.

$^1$H-NMR (DMSO-$d_6$, 300 MHz) δ 0.89-0.99 (4H, m), 1.92 (3H, s), 1.94-2.04 (1H, m), 5.02 (2H, br s), 6.25 (1H, d, J=2.3 Hz), 6.38 (1H, dd, J=8.1, 2.3 Hz), 6.93 (1H, d, J=8.1 Hz), 6.97 (1H, d, J=8.7 Hz), 8.11 (1H, d, J=8.7 Hz), 12.65 (1H, br s).

Example 34

Production of N-[5-(2-methyl-5-{[(2E)-3-(pyridin-3-yl)prop-2-enoyl]amino}phenoxy)[1,3]thiazolo[5,4-b]pyridin-2-yl]cyclopropanecarboxamide

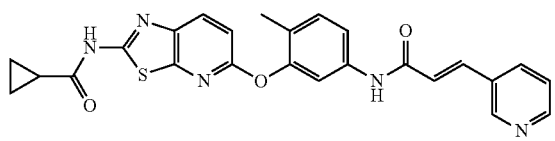 [SMILES: Cc1ccc(NC(=O)/C=C/c2cccnc2)cc1Oc1ccc2nc(NC(=O)C3CC3)sc2n1]

A solution of N-[5-(5-amino-2-methylphenoxy)[1,3]thiazolo[5,4-b]pyridin-2-yl]cyclopropanecarboxamide (41 mg, 0.12 mmol) produced in Reference Example 1,3-(3-pyridyl)acrylic acid (22 mg, 0.15 mmol), HOBt (20 mg, 0.15 mmol) and 1-ethyl-3-(3-dimethylaminopropyl)carbodiimide hydrochloride (28 mg, 0.15 mmmo) in N,N-dimethylformamide (3 mL) was stirred at room temperature overnight. Ethyl acetate (3 mL) and water (3 mL) were added to the reaction mixture, and the organic layer was dehydrated with Presep Tube manufactured by Wako Pure Chemical Industries, Ltd, and concentrated. Dimethyl sulfoxide was added to the residue, and methanol was further added. The precipitate was collected by filtration, washed with methanol and dried to give the title compound (28.6 mg, 51%) as a powder.

LC-MS m/z 472 (ESI+)

Example 35

Production of N-(5-{2-methyl-5-[(3-phenylprop-2-ynoyl)amino]phenoxy}[1,3]thiazolo[5,4-b]pyridin-2-yl)cyclopropanecarboxamide

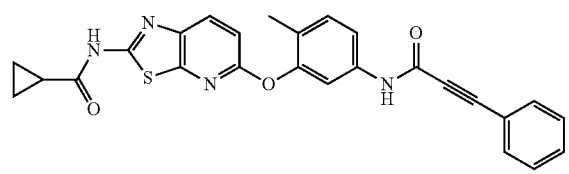 [SMILES: Cc1ccc(NC(=O)C#Cc2ccccc2)cc1Oc1ccc2nc(NC(=O)C3CC3)sc2n1]

A solution of N-[5-(5-amino-2-methylphenoxy)[1,3]thiazolo[5,4-b]pyridin-2-yl]cyclopropanecarboxamide (41 mg, 0.12 mmol) produced in Reference Example 1,3-phenylprop-2-ynoic acid (21 mg, 0.15 mmol), HOBt (20 mg, 0.15 mmol) and 1-ethyl-3-(3-dimethylaminopropyl)carbodiimide hydrochloride (28 mg, 0.15 mmol) in N,N-dimethylformamide (3 mL) was stirred at room temperature overnight. Ethyl acetate (3 mL) and water (3 ml) were added to the reaction mixture, and the organic layer was dehydrated with Presep Tube manufactured by Wako Pure Chemical Industries, Ltd, and concentrated. The residue was dissolved in dimethyl sulfoxide, and purified by preparative HPLC. The obtained fraction was concentrated to give the title compound (6.3 mg, 11%) as a powder.

LC-MS m/z 469 (ESI+)

Examples 36-57 were produced according to the method shown in Example 34 or Example 35.

TABLE 1

| Ex. | structure | name | LCMS m/z | yield (mg) | yield (%) |
|---|---|---|---|---|---|
| 36 | 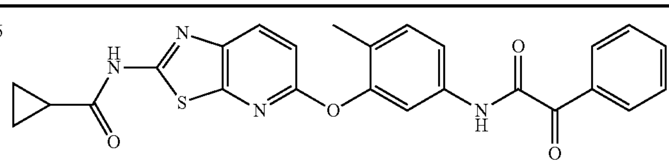 | N-[5-(2-methyl-5-{[oxo(phenyl)acetyl]amino}phenoxy)[1,3]-thiazolo-[5,4-b]-pyridin-2-yl]cyclopropanecarboxamide | 473 | 6.7 | 12 |

TABLE 1-continued

| Ex. | structure | name | LCMS m/z | yield (mg) | yield (%) |
|---|---|---|---|---|---|
| 37 | 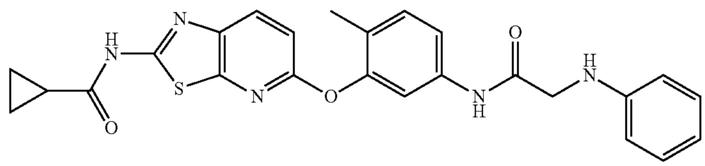 [SMILES: Cc1ccc(NC(=O)CNc2ccccc2)cc1Oc1ccc2nc(NC(=O)C3CC3)sc2n1] | N-(5-{2-methyl-5-[(N-phenylglycyl)amino]-phenoxy} [1,3]-thiazolo-[5,4-b]pyridin-2-yl)cyclo-propanecarboxamide | 474 | 7 | 12 |
| 38 | 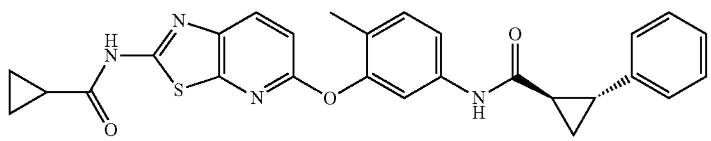 [SMILES: Cc1ccc(NC(=O)[C@@H]2C[C@H]2c2ccccc2)cc1Oc1ccc2nc(NC(=O)C3CC3)sc2n1] | (1R,2R)-N-[3-({2-[(cyclopropyl-carbonyl)amino] [1,3]-thiazolo[5,4-b]pyridin-5-yl}oxy)-4-methylphenyl]-2-phenylcyclopropane-carboxamide | 485 | 11.1 | 19 |
| 39 | 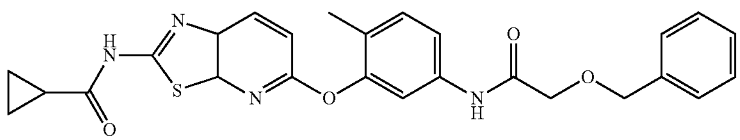 [SMILES: Cc1ccc(NC(=O)COCc2ccccc2)cc1OC1=NC2SC(NC(=O)C3CC3)=NC2C=C1] | N-[5-(5-{[(benzyl-oxy)acetyl]amino}-2-methylphenoxy) [1,3]-thiazolo[5,4-b]-pyridin-2-yl]cyclo-propanecarboxamide | 489 | 7.6 | 13 |
| 40 | 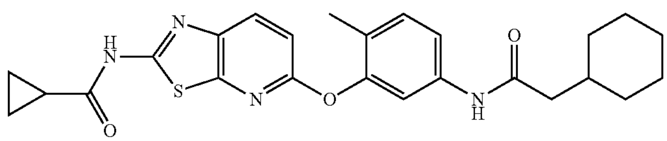 [SMILES: Cc1ccc(NC(=O)CC2CCCCC2)cc1Oc1ccc2nc(NC(=O)C3CC3)sc2n1] | N-(5-{5-[(cyclohexyl-acetyl)amino]-2-methylphenoxy} [1,3]-thiazolo[5,4-b]-pyridin-2-yl)cyclo-propanecarboxamide | 465 | 22.1 | 40 |
| 41 | 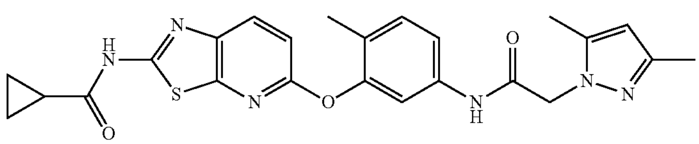 [SMILES: Cc1cc(C)n(CC(=O)Nc2ccc(C)c(Oc3ccc4nc(NC(=O)C5CC5)sc4n3)c2)n1] | N-[5-(5-{[(3,5-dimethyl-1H-pyrazol-1-yl)acetyl]amino}-2-methylphenoxy)-[1,3]thiazolo[5,4-b]pyridin-2-yl]cyclo-propanecarboxamide | 477 | 4.3 | 7.5 |
| 42 | 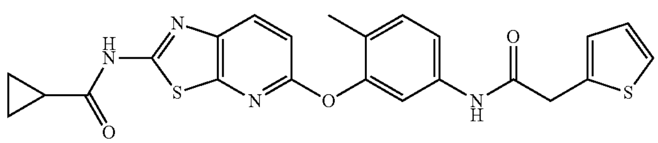 [SMILES: Cc1ccc(NC(=O)Cc2cccs2)cc1Oc1ccc2nc(NC(=O)C3CC3)sc2n1] | N-(5-{2-methyl-5-[(thiophen-2-ylacetyl)amino]-phenoxy}[1,3]-thiazolo[5,4-b]-pyridin-2-yl)cyclo-propanecarboxamide | 465 | 4.2 | 7.5 |
| 43 | 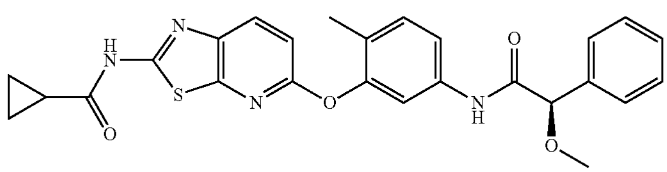 [SMILES: CO[C@@H](C(=O)Nc1ccc(C)c(Oc2ccc3nc(NC(=O)C4CC4)sc3n2)c1)c1ccccc1] | N-[5-(5-{[(2R)-2-methoxy-2-phenyl-acetyl]amino}-2-methylphenoxy)[1,3]-thiazolo[5,4-b]-pyridin-2-yl]cyclo-propanecarboxamide | 489 | 25.9 | 44 |
| 44 | 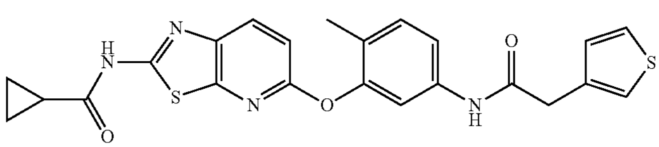 [SMILES: Cc1ccc(NC(=O)Cc2ccsc2)cc1Oc1ccc2nc(NC(=O)C3CC3)sc2n1] | N-(5-{2-methyl-5-[(thiophen-3-ylacetyl)amino]-phenoxy} [1,3]thia-zolo[5,4-b]pyridin-2-yl)cyclo-propanecarboxamide | 465 | 7.9 | 14 |
| 45 | 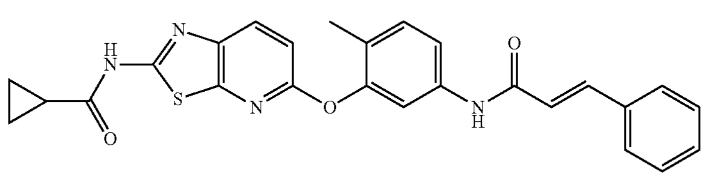 [SMILES: Cc1ccc(NC(=O)/C=C/c2ccccc2)cc1Oc1ccc2nc(NC(=O)C3CC3)sc2n1] | N-[5-(2-methyl-5-{[(2E)-3-phenylprop-2-enoyl]amino}-phenoxy) [1,3]thia-zolo[5,4-b]pyridin-2-yl]cyclo-propanecarboxamide | 471 | 16.5 | 29 |

TABLE 1-continued

| Ex. | structure | name | LCMS m/z | yield (mg) | yield (%) |
|---|---|---|---|---|---|
| 46 | 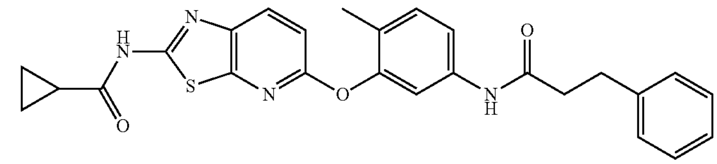 [SMILES: Cc1ccc(NC(=O)CCc2ccccc2)cc1Oc1ccc2nc(NC(=O)C3CC3)sc2n1] | N-(5-{2-methyl-5-[(3-phenyl-propanoyl)amino]-phenoxy} [1,3]-thiazolo[5,4-b]-pyridin-2-yl)cyclo-propanecarboxamide | 473 | 17.5 | 31 |
| 47 | 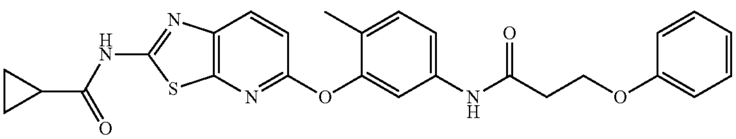 [SMILES: Cc1ccc(NC(=O)CCOc2ccccc2)cc1Oc1ccc2nc(NC(=O)C3CC3)sc2n1] | N-{5-{2-methyl-5-[(3-phenoxy-propanoyl)amino]-phenoxy} [1,3]-thiazolo[5,4-b]-pyridin-2-yl)cyclo-propanecarboxamide | 489 | 13.5 | 23 |
| 48 | 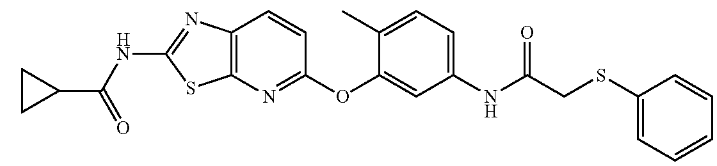 | N-[5-(2-methyl-5-{[(phenylsulfanyl)-acetyl]amino}-phenoxy) [1,3]-thiazolo[5,4-b]-pyridin-2-yl]cyclo-propanecarboxamide | 491 | 13.9 | 24 |
| 49 | 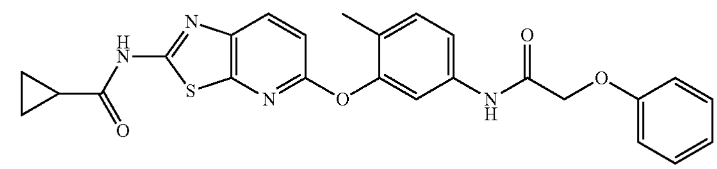 [SMILES: Cc1ccc(NC(=O)COc2ccccc2)cc1Oc1ccc2nc(NC(=O)C3CC3)sc2n1] | N-(5-{2-methyl-5-[(phenoxyacetyl)-amino]phenoxy} [1,3]-thiazolo[5,4-b]-pyridin-2-yl)cyclo-propanecarboxamide | 475 | 5 | 8.8 |
| 50 | 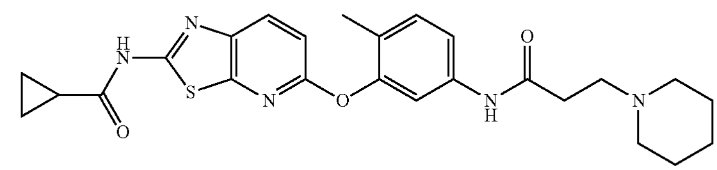 [SMILES: Cc1ccc(NC(=O)CCN2CCCCC2)cc1Oc1ccc2nc(NC(=O)C3CC3)sc2n1] | N-(5-{2-methyl-5-[(3-piperidin-1-yl-propanoyl)amino]-phenoxy} [1,3]-thiazolo[5,4-b]-pyridin-2-yl)cyclo-propanecarboxamide | 480 | 2.9 | 5.0 |
| 51 | 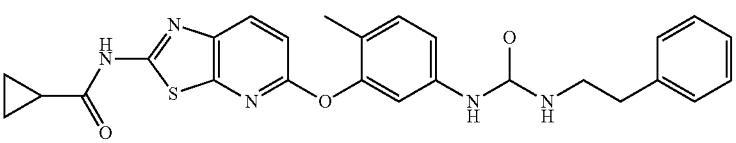 [SMILES: Cc1ccc(NC(O)NCCc2ccccc2)cc1Oc1ccc2nc(NC(=O)C3CC3)sc2n1] | N-[5-(2-methyl-5-{[(2-phenylethyl)-carbamoyl]amino}-phenoxy) [1,3]thia-zolo[5,4-b]pyridin-2-yl]cyclo-propanecarboxamide | 488 | 2.8 | 4.8 |
| 52 | 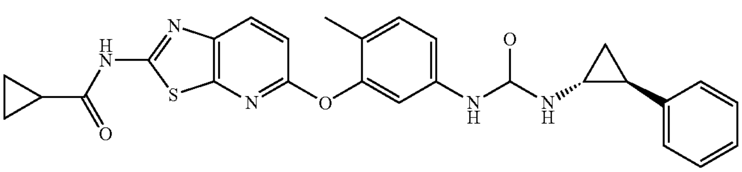 [SMILES: Cc1ccc(NC(O)N[C@@H]2C[C@H]2c2ccccc2)cc1Oc1ccc2nc(NC(=O)C3CC3)sc2n1] | N-{5-[2-methyl-5-({[(1R,2S)-2-phenyl-cyclopropyl]-carbamoyl}amino)-phenoxy] [1,3]thia-zolo[5,4-b]pyridin-2-yl}cyclo-propanecarboxamide | 500 | 3.9 | 6.5 |
| 53 | 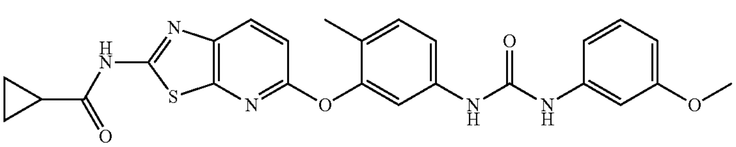 [SMILES: COc1cccc(NC(=O)Nc2ccc(C)c(Oc3ccc4nc(NC(=O)C5CC5)sc4n3)c2)c1] | N-[5-(5-{[(3-methoxyphenyl)-carbamoyl]amino}-2-methylphenoxy) [1,3]-thiazolo[5,4-b]-pyridin-2-yl]cyclo-propanecarboxamide | 490 | 9.5 | 16 |
| 54 | 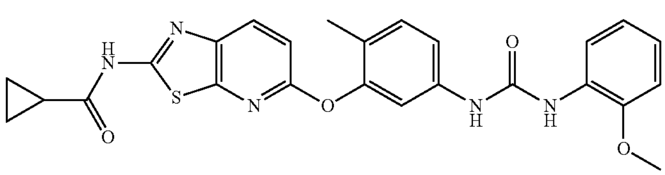 [SMILES: COc1ccccc1NC(=O)Nc1ccc(C)c(Oc2ccc3nc(NC(=O)C4CC4)sc3n2)c1] | N-[5-(5-{[(2-methoxyphenyl)carba-moyl]amino}-2-methylphenoxy) [1,3]-thiazolo[5,4-b]-pyridin-2-yl]cyclo-propanecarboxamide | 490 | 3.6 | 6.1 |

TABLE 1-continued

| Ex. | structure | name | LCMS m/z | yield (mg) | yield (%) |
|---|---|---|---|---|---|
| 55 | 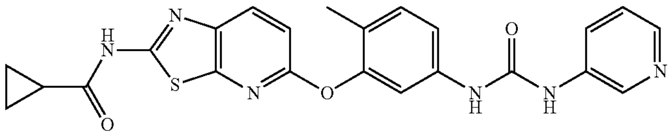 [SMILES: Cc1ccc(NC(=O)Nc2cccnc2)cc1Oc1ccc2nc(NC(=O)C3CC3)sc2n1] | N-(5-{2-methyl-5-[(pyridin-3-ylcarbamoyl)amino]phenoxy} [1,3]thiazolo[5,4-b]pyridin-2-yl)cyclopropanecarboxamide | 461 | 31.8 | 58 |
| 56 | 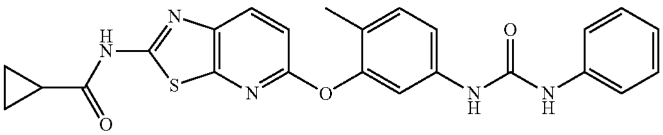 [SMILES: Cc1ccc(NC(=O)Nc2ccccc2)cc1Oc1ccc2nc(NC(=O)C3CC3)sc2n1] | N-(5-{2-methyl-5-[(phenylcarbamoyl)amino]phenoxy} [1,3]-thiazolo[5,4-b]-pyridin-2-yl)cyclopropanecarboxamide | 460 | 1.9 | 3.4 |
| 57 | 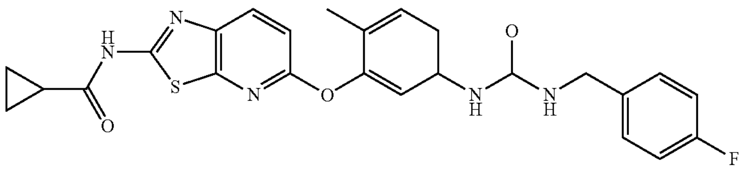 [SMILES: CC1=CCC(NC(O)NCc2ccc(F)cc2)C=C1Oc1ccc2nc(NC(=O)C3CC3)sc2n1] | N-[5-(5-{[(4-fluorobenzyl)carbamoyl]amino}-2-methylphenoxy) [1,3]-thiazolo[5,4-b]-pyridin-2-yl]cyclopropanecarboxamide | 492 | 2.3 | 3.9 |

Formulation Example 1

A medicament containing the compound of the present invention as an active ingredient can be produced, for example, according to the following formulation.

1. Capsule

| | | |
|---|---|---|
| (1) compound of Example 1 | 40 mg | |
| (2) lactose | 70 mg | |
| (3) microcrystalline cellulose | 9 mg | |
| (4) magnesium stearate | 1 mg | |
| 1 capsule | 120 mg | |

(1), (2), (3) and ½ of (4) are blended and granulated. The rest of (4) is added and the total amount is sealed in a gelatin capsule.

2. Tablet

| | | |
|---|---|---|
| (1) compound of Example 1 | 40 mg | |
| (2) lactose | 58 mg | |
| (3) cornstarch | 18 mg | |
| (4) microcrystalline cellulose | 3.5 mg | |
| (5) magnesium stearate | 0.5 mg | |
| 1 tablet | 120 mg | |

(1), (2), (3), ⅔ of (4) and ½ of (5) are blended and granulated. The rest of (4) and (5) is added to the granules and the mixture is compression formed into a tablet.

Formulation Example 2

The compound (50 mg) obtained in Example 1 is dissolved in the Japanese Pharmacopoeia distilled water for injection (50 mL), and the Japanese Pharmacopoeia distilled water for injection is added to make the total amount 100 mL. This solution is aseptically filtered. The solution (1 mL) is aseptically filled in a vial for injection, sealed and freeze-dried.

Experimental Example 1

Cloning of human BRAF gene and preparation of recombinant baculovirus

Human BRAF gene was cloned by PCR using human Testis cDNA library (Clontech) as a template. The primer used for PCR was prepared from base sequence (Genbank Accession No.: NM 004333) information of BRAF gene by adding a base sequence encoding Flag peptide and a recognition sequence of the restriction enzyme to area encoding the BRAF kinase domain region, so that the protein contains an N-terminal Flag. The primer base sequences are shown below.

BRAF-U:
(SEQ ID NO: 1)
5'-AAAGAATTCACCATGGACTACAAGGACGACGATGACAAGACCCCC
CCTGCCTCATTACCTGGCT-3'
and

BRAF-L:
(SEQ ID NO: 2)
5'-AAAAGTCGACTCAGTGGACAGGAAACGCACCATAT-3'

The PCR reaction was conducted using Pyrobest (Takara Shuzo Co., Ltd.). The obtained PCR product was electrophoresed on agarose gel (1%), the DNA fragment amplified by PCR was recovered from the gel, and then digested with restriction enzymes EcoRI and SalI. The DNA treated with the restriction enzymes was electrophoresed on agarose gel (1%), and the obtained DNA fragment was recovered. The recovered DNA fragment was ligated to plasmid pFAST-BAC1 (Invitrogen) digested with restriction enzymes EcoRI and SalI to give expression plasmid pFB-BRAF, and the base sequence of the insert fragment was confirmed. In addition, mutation was introduced into V600E using a Quick change Site Directed Mutagenesis kit (Stratagene). The base sequences of the primers used are shown in the following.

```
V600E-U:
                                          (SEQ ID NO: 3)
5'-GGTCTAGCTACAGAGAAATCTCGATGGAG-3'
and V600E-L:
                                          (SEQ ID NO: 4)
5'-CTCCATCGAGATTTCTCTGTAGCTAGACC-3'
```

The obtained plasmid was sequenced to confirm the introduction of mutation into V600E. The DNA was digested with restriction enzymes EcoRI and SalI, DNA treated with the restriction enzymes was electrophoresed on agarose gel (1%), and the obtained DNA fragment was recovered. The recovered DNA fragment was ligated to plasmid pFASTBAC1 (Invitrogen) digested with restriction enzymes EcoRI and SalI to give expression plasmid pFB-V600E.

Using BAC-TO-BAC Baculovirus Expression System (Invitrogen), virus stock BAC-V600E of recombinant baculovirus was prepared.

Experimental Example 2

Preparation of BRAF (V600E) Protein

SF-21 cells (Invitrogen) were seeded at $1 \times 10^6$ cells/mL to Sf-900II SFM medium (1 L, Invitrogen) containing 10% fetal bovine serum (Trace), 50 mg/L Gentamicin (Invitrogen) and 0.1% is Pluronic F-68 (Invitrogen), and shaking culture was performed using a 2 L volume Erlenmeyer flask at 27° C., 100 rpm. After culturing for 24 hrs, 13.4 mL of recombinant baculovirus BAC-V600E was added to the mixture, and the mixture was further cultured for 3 days. The culture medium was centrifuged at 2,000 rpm for 5 min, to give virus-infected cells. The infected cells were washed with a phosphate buffered saline (Invitrogen), centrifuged under the same conditions, and the cells were preserved at −80° C. The cryopreserved cells were thawed in ice, suspended in buffer A (50 mM Tris buffer (30 mL, pH 7.4) containing 20% glycerol, 0.15 M NaCl) supplemented with Complete Protease Inhibitor (Boehringer), and ruptured 3 times with Polytron homogenizer (Kinematica) at 20,000 rpm for 30 sec. The ruptured medium was clarified by centrifugation at 40,000 rpm for 30 min, and filtered with a 0.45 μm filter. The filtrate was passed through a column packed with Anti-FLAG M2 Affinity Gel (4 mL, Sigma) at a flow rate of about 0.5 mL/min. The column was washed with buffer A, and eluted with buffer A containing 100 μg/mL of FLAG peptide (Sigma). The buffer of this concentrate was exchanged using NAP25 column (Amersham Bioscience) equilibrated with buffer A and the fractions were cryopreserved at −80° C.

Experimental Example 3

Cloning of human GSTP1 gene and preparation of pGP1P expression plasmid Human GSTP1 gene was obtained by performing PCR using PCR-ready cDNA human universal library (Clontech) as a template. The primers used for PCR were

```
GSTP1UNHE:
                                          (SEQ ID NO: 5)
5'-ATATGCTAGCACCATGCCGCCCTACACCGTG-3'
and
```

```
GSTP1LHIN:
                                          (SEQ ID NO: 6)
5'-TATAAAGCTTCTGTTTCCCGTTGCCATTGATG-3'.
```

The PCR reaction was performed using Pyrobest (Takara Shuzo Co., Ltd.). The obtained PCR product was electrophoresed on agarose gel (1%), and the DNA fragment amplified by PCR was recovered from the gel, and digested with restriction enzymes NheI and HindIII. The DNA treated with the restriction enzyme was electrophoresed on agarose gel (1%), and the obtained DNA fragment was recovered.

The following synthesized DNA fragments were annealed to give a DNA fragment encoding PreScission protease recognition site.

```
PPINSU:
                                          (SEQ ID NO: 7)
5'-AGCTTGGAGGTGGACTGGAAGTTCTGTTCCAGGGGCCCCTGG-3'
and PPINSL:
                                          (SEQ ID NO: 8)
5'-GATCCCAGGGGCCCCTGGAACAGAACTTCCAGTCCACCTCCA-3'
```

The DNA fragment encoding hGSTP1 and PreScission protease recognition sites was ligated with pcDNA3.1 digested with restriction enzymes NheI and HindIII to give a pGP1p expression vector.

Experimental Example 4

Cloning of Human MEK1 (K96R) Gene and Preparation of GST1-MEK1 (K96R) Expression Plasmid Cloning of human MEK1 gene was performed by PCR using human lung cDNA library (Clontech) as a template. The primers used for PCR were prepared based on the information of the base sequence of MEK1 gene (Genbank Accession No.: NM_002755). The base sequences of the primers are shown below.

```
MEK1-U:
                                          (SEQ ID NO: 9)
5'-AAAAGTCGACATGCCCAAGAAGAAGCCGACGCCCATCC-3'
and MEK1-L:
                                          (SEQ ID NO: 10)
5'-TTTTGCGGCCGCAGGGGACTCGCTCTTTGTTGCTTCC-3'
```

The PCR reaction was performed using Pyrobest (Takara Shuzo Co., Ltd.). The obtained PCR product was electrophoresed on agarose gel (1%), and the DNA fragment amplified by PCR was recovered from the gel, and digested with restriction enzymes SalI and NotI. The DNA treated with the restriction enzymes was electrophoresed on agarose gel (1%), and the obtained DNA fragment was recovered. The recovered DNA fragment was ligated to plasmid pGEX6p-3 (GE Healthcare) digested with restriction enzymes SalI and NotI to give expression plasmid pGEX6p-MEK1, and the gene sequence of the insertion fragment was confirmed. To obtain a pGEX6p-MEK1 (K96R) expression gene, K96R gene mutation was introduced using Quick change Site Directed Mutagenesis kit (Stratagene).

pGEX6p-MEK1 (K96R) was digested with restriction enzymes BamHI and NotI. The DNA treated with the restriction enzymes was electrophoresed on agarose gel (1%), and a DNA fragment encoding MEK1 (K96R) was recovered. The recovered DNA fragment was ligated to plasmid pGFlp digested with restriction enzymes BamHI and NotI to give expression plasmid pGFlp-MEK1 (K96R).

Experimental Example 5

Preparation of GSTP1-MEK1 (K96R)

MEK1 (K96R) with GSTP1 tag was expressed using FreeStyle 293 Expression System (Invitrogen). FreeStyle 293-F cells were seeded at $1.1 \times 10^6$ cells/ml on FreeStyle 293 Expression Medium (1140 ml). 293 Fectin (1730 μl) was diluted with Opti-MEM medium (43 ml), and blended with pGFlp-MEK1 (K96R) expression plasmid (1300 μg) diluted with Opti-MEM I (43 ml). The mixture was left standing at room temperature for 20 min, and added to FreeStyle 293-F cells. After shaking at 37° C., 125 rpm in the presence of 8% $CO_2$ for 3 days, the cells were collected. A suspending buffer (80 ml, 50 mmol/L HEPES (pH 8), 100 mmol/L NaCl, 1 mmol/L EDTA, 1 mmol/L Sodium Orthovanadate, 10% (v/v) Glycerol Complete Protease Inhibitor (Roche)) was added, and the mixture was disrupted with Polytron homogenizer (Kinematica) at 20000 rpm for 20 sec. A solution after the disruption was centrifuged at 500×g for 10 min, and the supernatant was subjected to further centrifugation operation at 100,000×g for 60 min. The supernatant after the centrifugation operation was added to Glutathione Seoharose 4B column (GE Healthcare, 2 cm×5 cm, 15.7 ml). The column was washed with a solution containing 50 mmol/L HEPES (pH 7.5), 0.1 mol/L NaCl, 1 mmol/L DTT, 1 mM EDTA and 10% (v/v) Glycerol, and eluted with a solution containing 0.1 mmol/L Tris-HCl, 1 mmol/L DTT, 10% (v/v) Glycerol and 10 mmol/L glutathione. The eluate was concentrated with Vivaspin 20-10K (GE Healthcare) to 5 ml, and added to HiLoad 26/60 Superdex 200 pg column (GE Healthcare) equilibrated with a solution containing 50 mmol/L HEPES (pH 7.5), 0.1 mol/L NaCl, 1 mmol/L DTT, 10% (v/v) Glycerol. The fraction containing GSTP1-MEK1 (K96R) was concentrated with Vivaspin 20-10K. The protein concentration was measured with BCA protein assay kit (Pierce).

Test Example 1

Determination of BRAF (V600E) Kinase Inhibitory Activity

A test compound (2.5 μL) dissolved in dimethyl sulfoxide (DMSO) was added to 37.5 μL of a reaction solution (25 mM HEPES (pH 7.5), 10 mM magnesium acetate, 1 mM dithiothreitol) containing 30 ng of BRAF (V600E) enzyme and 250 ng of recombinant protein GSTP1-MEK1 (K96R) prepared using FreeStyle 293 expression system (Invitrogen), and the mixture was incubated at room temperature for 10 min. 10 μL of ATP solution (2.5 μM ATP, 0.1 μCi [γ-$^{32}$P]ATP) was added to the obtained mixture, and the mixture was reacted at room temperature for 20 min. The reaction was quenched by adding 50 μL of ice-cooled 20% trichloroacetic acid (Wako Pure Chemical Industries, Ltd.) to the reaction solution. The reaction solution was allowed to stand at 4° C. for 30 min., and the acid-precipitable fraction was transferred to GF/C filter plate (Millipore Corporation) using cell harvester (PerkinElmer). The plate was dried at 45° C. for 60 min., and 40 μL of MicroScinti 0 (PerkinElmer) was added thereto. The radioactivity was measured using TopCount (PerkinElmer). The kinase inhibitory rate (%) of the test compound was calculated by the following formula:

Inhibitory rate (%)=(1−(count of test compound−blank)÷(control−blank))×100

The count of the solution reacted without addition of the compound was used as a "control", and the count of the solution without the compound and enzyme was used as a "blank".

The obtained results are shown in Table 2. The results show that the compound of the present invention strongly inhibits an activity of BRAF (V600E) kinase.

TABLE 2

| Example No. | inhibitory rate (%) at 1.0 μm |
|---|---|
| 1 | 98 |
| 11 | 99 |
| 19 | 100 |
| 21 | 98 |

Test Example 2

Colorectal Cancer Cell HT-29 Intracellular MEK Phosphorylation Inhibitory Activity In Vitro 500 μL of a cell suspension of human colorectal cancer cell HT-29 (purchased from American Type Culture Collection (ATCC)) was plated in a 48-well plate (100,000 cells/well), and the cells were cultured overnight at 37° C. in the presence of 5% $CO_2$, treated with a test compound (250 μL/well) diluted in 3-fold dilution series and cultured for 2 hrs. After 2 hrs, the culture medium containing the test compound was removed, and the cells were lysed with SDS sample buffer (100 μL/well) and heated at 95° C. for 5 min. Thereafter, the cells lysed with SDS sample buffer were applied to SDS-PAGE, and the protein was transferred onto Sequi-Blot™ PVDF Membrane (Bio-Rad) by the Western blot method. The PDVF membrane was blocked with a Block-Ace solution (Snow Brand Milk Products Co., Ltd) dissolved in phosphate buffered saline (MP Biochemicals) to 5% W/V, and reacted overnight with anti-phosphorylated MEK1/2 (Ser217/221) (Cell signaling) diluted 1000-fold with phosphate buffered saline containing 0.4% Block-Ace. The membrane was washed with phosphate buffered saline containing 0.1% Tween 20 (Wako Pure Chemical Industries, Ltd.), and reacted at room temperature for 1 hr with HRP labeled rabbit IgG polyclonal antibody (Cell signaling) diluted 1000-fold with phosphate buffered saline containing 0.4% Block-Ace. The membrane was washed in the same manner as above, chemical luminescence of a phosphorylated MEK1/2 protein labeled with the antibody, which was caused by ECL-plus Detection Reagent (Amersham bioscience), was detected by Luminescent Image Analyzer LAS-1000 (FUJIFILM Corporation). Taking the luminescence of the control group free of the test compound as 100%, the concentration ($IC_{50}$ value) of the compound necessary for inhibiting the residual luminescence to 50% of the control group was calculated. The results are shown in Table 3-A. In addition, MEK1/2 protein phosphorylation inhibitory rate (%) of the test compound at compound concentration 0.5 μM was calculated by the following formula. The results are shown in Table 3-B.

Inhibitory rate (%)=(1−(luminescence of test compound−blank)÷(luminescence of control group−blank))×100

From these results, it has been clarified that the compound of the present invention strongly inhibits MEK phosphorylation.

TABLE 3-A

| Example No. | IC$_{50}$ (nM) |
|---|---|
| 3 | <300 |
| 13 | <300 |
| 23 | <300 |

TABLE 3-B

| Example No. | inhibitory rate (%) at 0.5 μM |
|---|---|
| 3 | 94 |
| 13 | 98 |
| 22 | 88 |
| 23 | 88 |

Test Example 3

Colorectal Cancer Cell HT-29 Growth Suppressive Activity in Vitro

100 μL of a cell suspension (3,000 cells/well) of human colorectal cancer cell HT-29 (purchased from ATCC) was plated in a 96-well plate, and the cells were cultured at 37° C. in a 5% CO$_2$ gas incubator. The next day, 100 μL of each test compound solution diluted in 2-fold serial dilution, diluted from maximum concentration 20 μM, was added, and the cells were cultured for 3 days. As for Example 44, 100 μl of each test compound solution (4-fold serially diluted, diluted from maximum concentration 20 μM) was added, and the cells were cultured for 3 days. The culture medium containing the test compound was removed, and the cells were washed with phosphate buffered saline (PBS). A 50% trichloroacetic acid solution was added to the final concentration of 10% (v/v), and the mixture was stood overnight at 4° C., whereby the cells were fixed to the plate. Then, a dye SRB 0.4% (w/v) solution (dissolved in 1% acetic acid) was added at 50 μl/well, whereby the cell protein was fixed and stained (Skehan et al., Journal Of National Cancer Institute, vol. 82, pp. 1107-1112, 1990). The cells were washed 3 times with 1% acetic acid solution (200 μL/well), and 100 μL of an extract (10 mM Tris buffer) was added to extract the dye. The absorbance at an absorption wavelength 550 nm was measured, and cell amount was measured as a protein amount. Taking the protein amount of the control group free of the test compound solution as 100%, the proportion of the residual protein amount of each treatment group was determined and the concentration of the compound necessary for suppressing the residual cell amount to 50% of the control (IC$_{50}$ value) was calculated. The results are shown in Table 4-A. In addition, cell proliferation inhibitory rate (%) of the test compound at compound concentration 5.0 μM was calculated by the following formula. The results are shown in Table 4-B.

Inhibitory rate (%)=(1−(absorbance of test compound−blank)÷(absorbance of control group−blank))×100

From these results, it has been clarified that the compound of the present invention strongly suppresses proliferation of colorectal cancer cells.

TABLE 4-A

| Example No. | IC$_{50}$ (nM) |
|---|---|
| 9 | <500 |
| 29 | <500 |
| 44 | <500 |

TABLE 4-B

| Example No. | inhibitory rate (%) at 5.0 μM |
|---|---|
| 9 | 100 |
| 29 | 74 |
| 44 | 98 |

INDUSTRIAL APPLICABILITY

The compound of the present invention show superior inhibitory activity on Raf. Therefore, a clinically useful drug for the prophylaxis or treatment of diseases related to Raf (e.g., cancer etc.) can be provided. Moreover, since the compound of the present invention are also superior in efficacy expression, pharmacokinetics, solubility, interaction with other pharmaceutical products, safety and stability, they are useful as medicaments.

This application is based on Japanese patent application No. 2008-306614, the contents of which are incorporated in full herein by this reference.

The invention claimed is:

1. A compound represented by the formula

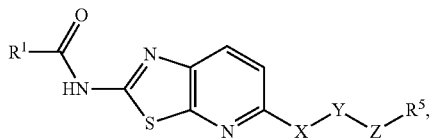

(I)

wherein
R$^1$ is cyclopropyl;
X is —O—, —NH—, or —N(CH$_3$)—;
Y is

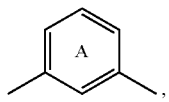

wherein ring A is a benzene ring optionally having 1 to 3 substituents selected from the group consisting of
(1) C$_{1-6}$ alkyl, and
(2) a halogen atom;
Z is
(1) —NHCO—W$^{1a}$—,
wherein W$^{1a}$ is
(i) a C$_{1-6}$ alkylene group optionally having 1 to 3 substituents selected from the group consisting of
(a) amino, and
(b) C$_{1-6}$ alkoxy,
(ii) a C$_{2-6}$ alkenylene group,
(iii) a C$_{2-6}$ alkynylene group, or
(iv) a C$_{3-6}$ cycloalkylene group,
(2) —NHCO—W$^{1b}$—O—,
wherein W$^{1b}$ is a C$_{1-6}$ alkylene group,
(3) —NHCO—W$^{1c}$—O—W$^{2c}$—,
wherein W$^{1c}$ is a C$_{1-6}$ alkylene group, and W$^{2c}$ is a C$_{1-6}$ alkylene group,
(4) —NHCO—W$^{1d}$—S—,
wherein W$^{1d}$ is a C$_{1-6}$ alkylene group,
(5) —NHCO—W$^{1e}$—NH—,
wherein W$^{1e}$ is a C$_{1-6}$ alkylene group,
(6) —NHCOO—W$^{1g}$—,
wherein W$^{1g}$ is a C$_{1-6}$ alkylene group,
(7) —NHCO—CO—,
(8) —NHCONH—,
(9) —NHCONH—W$^{1j}$—,
wherein W$^{1j}$ is
(i) a C$_{1-6}$ alkylene group, or
(ii) a C$_{3-6}$ cycloalkylene group, or
(10) —NHCONH—W$^{1k}$—O—,
wherein W$^{1k}$ is a C$_{1-6}$ alkylene group; and
R$^5$ is
(1) cyclohexyl, or
(2) phenyl optionally having 1 to 3 substituents selected from the group consisting of
(a) a halogen atom, and
(b) C$_{1-6}$ alkyl optionally having 1 to 3 halogen atoms,
or a salt thereof.

2. N-{5-[4-fluoro-3-({[2-(trifluoromethyl)phenyl]acetyl}-amino)phenoxy][1,3]thiazolo[5,4-b]pyridin-2-yl}cyclopropanecarboxamide, or a salt thereof.

3. N-{5-[4-fluoro-3-({[4-(trifluoromethyl)phenyl]acetyl}-amino)phenoxy][1,3]thiazolo[5,4-b]pyridin-2-yl}cyclopropanecarboxamide, or a salt thereof.

4. N-{5-[4-fluoro-3-({[4-(trifluoromethyl)phenyl]acetyl}-amino)phenoxy][1,3]thiazolo[5,4-b]pyridin-2-yl}cyclopropanecarboxamide, or a salt thereof.

5. N-{5-[4-fluoro-3-({[3-(trifluoromethyl)phenyl]carbamoyl}-amino)phenoxy][1,3]thiazolo[5,4-b]pyridin-2-yl}cyclopropanecarboxamide, or a salt thereof.

6. A medicament comprising the compound according to claim 1.

7. The compound according to claim 1, wherein
Z is —NHCO—$W^{1a}$—
   wherein $W^{1a}$ is
   (i) a $C_{1-6}$ alkylene group optionally having 1 to 3 substituents selected from the group consisting of
      (a) amino, and
      (b) $C_{1-6}$ alkoxy,
   (ii) a $C_{2-6}$ alkenylene group,
   (iii) a $C_{2-6}$ alkynylene group, or
   (iv) a $C_{3-6}$ cycloalkylene group,
or salt thereof.

* * * * *

UNITED STATES PATENT AND TRADEMARK OFFICE
CERTIFICATE OF CORRECTION

PATENT NO. : 8,697,874 B2  
APPLICATION NO. : 13/132253  
DATED : April 15, 2014  
INVENTOR(S) : Okaniwa et al.

Page 1 of 1

It is certified that error appears in the above-identified patent and that said Letters Patent is hereby corrected as shown below:

In the Claims:

Column 106, line 60: delete "N-{5-[4-fluoro-3-({[4-(trifluoroethyl)phenyl]" and insert --N-{5-[4-fluoro-3-({[3-(trifluoromethyl)phenyl]--.

Signed and Sealed this  
Sixteenth Day of September, 2014

Michelle K. Lee  
*Deputy Director of the United States Patent and Trademark Office*